(12) United States Patent
Fletcher et al.

(10) Patent No.: US 9,476,882 B2
(45) Date of Patent: Oct. 25, 2016

(54) METHODS AND COMPOSITIONS FOR DIAGNOSING AND TREATING CANCER

(71) Applicant: THE BRIGHAM AND WOMEN'S HOSPITAL CORPORATION, Boston, MA (US)

(72) Inventors: Jonathan A. Fletcher, Brookline, MA (US); Cheng-Han Lee, Vancouver (CA)

(73) Assignee: The Brigham and Women's Hospital, Inc., Boston, MA (US)

(*) Notice: Subject to any disclaimer, the term of this patent is extended or adjusted under 35 U.S.C. 154(b) by 310 days.

(21) Appl. No.: 14/366,973

(22) PCT Filed: Dec. 31, 2012

(86) PCT No.: PCT/US2012/072264
§ 371 (c)(1),
(2) Date: Jun. 19, 2014

(87) PCT Pub. No.: WO2013/102187
PCT Pub. Date: Jul. 4, 2013

(65) Prior Publication Data
US 2014/0357516 A1    Dec. 4, 2014

Related U.S. Application Data

(60) Provisional application No. 61/581,317, filed on Dec. 29, 2011.

(51) Int. Cl.
*C12Q 1/68*     (2006.01)
*G01N 33/574*   (2006.01)
*C07K 14/47*    (2006.01)

(52) U.S. Cl.
CPC ......... *G01N 33/57484* (2013.01); *C07K 14/47* (2013.01); *C07K 14/4702* (2013.01); *C12Q 1/68* (2013.01); *C12Q 1/6886* (2013.01); *G01N 33/57407* (2013.01); *C07K 2319/00* (2013.01); *C12Q 2600/106* (2013.01); *C12Q 2600/156* (2013.01); *G01N 2800/52* (2013.01)

(58) Field of Classification Search
None
See application file for complete search history.

(56) References Cited

FOREIGN PATENT DOCUMENTS

WO    2007/048074    4/2007

OTHER PUBLICATIONS

Leunen et al. "Endometrial stromal sarcoma presenting as postpartum hemorrhage: report of a case with a sole t (10;17)(q22;p13) translocation." Gynecologic Oncology, 2003, 91, pp. 265-271.
Lee et al. "The histologic features of endometrial stromal sarcomas characterized by YWHAE rearrangement—distinction from usual low-grade endometrial stromal sarcoma with JAZF1 rearrangement." Modern Pathology, Feb. 2011, 24(2), p. 255A, abstract 1081.
Luk et al. "Assignment of the human 14-3-3 epsilon isoform (YWHAE) to human chromosome 17p13 by in situ hybridization." Cytogenet Cell Genet, 1997, 78, pp. 105-106.
Matos et al. "Identification of the genomic breakpoints of a novel chromosome translocation in myelodysplastic syndrome." Dissertation for a Master's degree in Oncology. Porto, Dec. 15, 2011, pp. 29-48.
Micci et al. "Consistent rearrangement of chromosomal band 6p21 with generation of fusion genes JAZF1/PHF1 and EPC1/PHF1 in endometrial stromal sarcoma." Cancer Res., 2006, 66(1), pp. 107-112.
Lee et al. "14-3-3 fusion oncogenes in high-grade endometrial stromal sarcoma." PNAS, Jan. 17, 2012, vol. 109, No. 3, pp. 929-934.

*Primary Examiner* — Samuel Woolwine
*Assistant Examiner* — Valerie Toodle
(74) *Attorney, Agent, or Firm* — Nixon Peabody LLP

(57) ABSTRACT

The invention provides assays, methods, systems, compositions, and kits for diagnosing and treating cancer.

12 Claims, 10 Drawing Sheets

SEQUENCE LISTING

```
<160> NUMBER OF SEQ ID NOS: 87

<210> SEQ ID NO 1
<211> LENGTH: 2970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggatgatc gagaggatct ggtgtaccag gcgaagctgg ccgagcaggc tgagcgatac        60
gacgaaatgg tggagtcaat gaagaaagta gcagggatgg atgtggagct gacagttgaa       120 gaagaaacc tcctatctgt tgcatataag aatgtgattg gagctagaag agcctcctgg        180
agaataatca gcagcattga acagaaagaa gaaaacaagg gaggagaaga caagctaaaa       240
atgattcggg aatatcggca aatggttgag actgagctaa agttaatctg ttgtgacatt       300
ctggatgtac tggacaaaca cctcattcca gcagctaaca ctggcgagtc caaggttttc       360
tattataaaa tgaaagggga ctaccacagg tatctggcag aatttgccac aggaaacgac       420
aggaaggagg ctgcggagaa cagcctagtg gcttataaag ctgctagtga tattgcaatg       480
acagaacttc caccaacgca tcctattcgc ttaggtcttg ctctcaattt ttccgtattc       540
tactacgaaa ttcttaattc ccctgaccgt gcctgcaggt tggcaaaagc agcttttgat       600
gatgcaattg cagaactgga tacgctgagt gaagaaagct ataaggactc tacacttatc       660
atgcagttgt tacgtgataa tctgacacta tggacttcag acatgcaggg tgacgcatac       720
ccagcgctgg gaccgggcgt gaccgcgaac cctggcacct ccctgtctgt gttcacggct       780
ctgcccttca ccacacccgc tcccggccca gcacacgggc cgctccttgt gactgcaggg       840
gctcctccag gcggccctct ggtgctgtct accctccca gcacacctct ggtgacagaa       900
caggatggct gcggcccgag tggggccggg gcttccaacg tctttgtcca gatgaggaca       960
gaggtggggc ctgtgaaggc cgctcaggcg cagaccttgg tcctaactca ggcccccctc      1020
gtctggcagg ctccaggcgc cctctgcgga ggtgttgtgt gtccacctcc cctactcctg      1080
```

```
gcagctgctc ctgtggtgcc tgttatggct gcccaggtgg ttgggggcac ccaggcctgt    1140
gagggaggct ggtcccaggg ccttcctctt ccaccaccac caccaccggc tgcccagctg    1200 cccccattg tgtcccaagg gaatgctggg ccatggccac aaggggctca cggagagggc     1260
agcctggctt cctcccaggc caaggccccg ccagatgact cctgtaaccc caggagtgtc    1320
tatgagaact tccgactctg gcagcactac aagcccctgg cccggaggca ccttccccag    1380
agtcctgaca ccgaagcgct tcgtgcttc ctcatcccag ttctccgatc cctgccccgg     1440
cggaagccca ccatgaccct ggaggaggga ctgtggcggg ccatgcggga atggcagcac    1500
acgagcaact tgaccggat gatcttctac gagatggcgg aaaagttcct ggagtttgag     1560
gctgaggagg agatgcagat tcagaaatcg caatggatga aggggcccca gtgcctgcct    1620
cctccagcca caccgaggct tgaacctcga ggacccccgg cccctgaggt ggtcaagcag    1680
ccagtgtacc ttcccagcaa ggccggcccc aaggccccga ctgcctgcct gccaccaccc    1740
aggccccaga ggccagtgac caaggcccgc cggccaccac cccggcccca ccggcgagca    1800
gagaccaagg cccgcctgcc accacccagg ccccagagac cagcagagac caaggtccct    1860
gaggagatcc ccccagaagt ggtgcaggag tatgtggaca tcatggagga gctgctgggg    1920
ccttccctcg gggccacggg ggagcccgag aaacaacggg aagagggcga agtgaagcag    1980
ccacaggaag aggactggac gcccccagac ccgggcctcc tgagctacac tgacaagctg    2040
tgttcccaga aagacttcgt caccaaggtg gaggccgtca ttcatcccca attcctggaa    2100
gaattgcttt ccccagatcc acagatggat ttcttggccc taagccagga gctggagcag    2160
gaggaaggac tcacccttgc ccagctagtg gagaagcgcc tcctaccctt gaaggagaaa    2220
cagcatgcga gggcagcccc tagtcgtggc acagcccggt tggactcaag ttcttctaag    2280
tttgcagctg gccaaggagc agagagagac gtccctgtcc cccaacaagg ggttggcatg    2340
gaaacctgcc caccccagac gactgcccgg gactctcagg gacgaggcag agcacacact    2400
ggcatggcca ggtccaaaga ctctgttgtg cttttgggat gtcaggattc ccctgggctg    2460
agggctgccc ggccaacctc tcctccccag gaccacagac ccacctgccc tggcgtgggt    2520
accaaggatg ccttggatct ccctggaggg tctcctgtca gggagtcaca tgggctggct    2580 cagggtcaa gtgaggagga ggaactcccc agcctggcct tcctcttggg ttcccagcac     2640
aagcttctgc cctggtggct accccagagc cctgtccctg cctcgggcct tctcagccca    2700
gaaaagtggg gaccccaggg aactcatcag ttcccatctg ctgagagaag aggcctcaac    2760
ctagcacctt ctcctgccaa caaggccaag aagcgacctc tctttggaag cctgtcccct    2820
gctgaaaaga caccccaccc agggcctggg ctcagggtct ctggggagca atccctgact    2880
tgggggctgg gtggccctc acagtctcaa aagagaaagg gtgacccctt ggtctccagg     2940
aaggagaaga agcagcgttg tagccagtag                                    2970
```

<210> SEQ ID NO 2
<211> LENGTH: 2970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atggatgatc gagaggatct ggtgtaccag gcgaagctgg ccgagcaggc tgagcgatac     60
gacgaaatgg tggagtcaat gaagaaagta gcagggatgg atgtggagct gacagttgaa    120
```

```
gaaagaaacc tcctatctgt tgcatataag aatgtgattg gagctagaag agcctcctgg      180
agaataatca gcagcattga acagaaagaa gaaacaagg gaggagaaga caagctaaaa       240
atgattcggg aatatcggca aatggttgag actgagctaa agttaatctg ttgtgacatt      300
ctggatgtac tggacaaaca cctcattcca gcagctaaca ctggcgagtc caaggttttc      360
tattataaaa tgaaggggga ctaccacagg tatctggcag aatttgccac aggaaacgac      420
aggaaggagg ctgcggagaa cagcctagtg gcttataaag ctgctagtga tattgcaatg      480
acagaacttc caccaacgca tcctattcgc ttaggtcttg ctctcaattt ttccgtattc      540
tactacgaaa ttcttaattc ccctgaccgt gcctgcaggt tggcaaaagc agcttttgat      600
gatgcaattg cagaactgga tacgctgagt gaagaaagct ataaggactc tacacttatc      660
atgcagttgt tacgtgataa tctgacacta tggacttcag acatgcaggg tgacgcatac      720
ccagtgctgg gaccgggcgt gaccgcgaac cctggcacct cctgtctgt gttcacggct       780
ctgcccttca ccacacccgc tcccggccca gcacacgggc cgctccttgt gactgcaggg      840
gctcctccag gcggccctct ggtgctgtct accttcccca gcacacctct ggtgacagaa      900
caggatggct gcggcccgag tggggccggg gcttccaacg tctttgtcca gatgaggaca      960
gaggtggggc ctgtgaaggc cgctcaggcg cagaccttgg tcctaactca ggcccccctc     1020
gtctggcagg ctccaggcgc cctctgcgga ggtgttgtgt gtccacctcc cctactcctg     1080
gcagctgctc ctgtggtgcc tgttatggct gcccaggtgg ttgggggcac ccaggcctgt     1140
gagggaggct ggtcccaggg ccttcctctt ccaccaccac caccaccggc tgcccagctg     1200
cccccccattg tgtcccaagg gaatgctggg ccatggccac aagggctca tggagagagc     1260
agcctggctt cctcccaggc caaggccccg ccagatgact cctgtaaccc caggagtgtc     1320
tatgagaact tccgactctg gcagcactac aagcccctgg cccggaggca ccttccccag     1380
agtcctgaca ccgaagcgct ttcgtgcttc ctcatcccag ttctccgatc gctggcccgg     1440
cggaagccca ccatgaccct ggaggaggga ctgtggcggg ccatgcggga atggcagcac     1500
acgagcaact ttgaccggat gatcttctac gagatggcgg aaaagttcct ggagtttgag     1560
gctgaggagg agatgcagat tcagaaatcg caatggatga aggggcccca gtgcctgcct     1620
cctccagcca caccgaggct tgaacctcga ggaccccgg ccctgaggt ggtcaagcag       1680
ccagtgtacc ttcccagcaa ggccggcccc aaggccccga ctgcctgcct gccaccaccc     1740
aggcccagca ggccagtgac caaggcccgc cggccaccac cccggcccca ccggcgagca     1800
gagaccaagg cccgcctgcc accacccagg ccccagagac cagcagagac caaggtccct     1860
gaggagatcc ccccagaagt ggtgcaggag tatgtggaca tcatggagga gctgctgggg     1920
ccttccctcg gggccacggg ggagcccgag aaacaacggg aagagggcaa agtgaagcag     1980
ccacaggaag aggactggac gccccagac ccgggcctcc tgagctacat tgacaagctg      2040
tgttcccaga aagacttcgt caccaaggtg gaggccgtca ttcatcccca attcctggaa     2100
gaattgcttt ccccagatcc acagatggat ttcttggccc taagccagga cctggagcag     2160
gaggaaggac tcacccttgc ccagctagtg gagaagcgcc tcccaccctt gaaggagaaa     2220
cagcatgcga gggcagcccc tagtcgtggc acagcccggt tggactcaag ttcttctaag     2280
tttgcagctg gccaaggagc agagagagac gtccctgacc cccaacaagg ggttggcatg     2340
gaaacctgcc cacccagat gactgccgg gactctcagg gacgaggcag agcacacact      2400
ggcatggcca ggtccgaaga ctctgttgtg cttttgggat gtcaggattc ccctgggctg     2460
agggctgcct ggccaaccte tcctccccag gaccacagac ccacctgccc tggcgtgggt     2520
```

```
accaaggatg ccttggatct ccctggaggg tctcctgtca gggagtcaca tgggctggct    2580 cagggggtcaa gtgaggagga ggaactcccc agcctggcct tcctcttggg ttcccagcac   2640
aagcttctgc cctggtggct accccagagc cctgtccctg cctcgggcct tctcagccca    2700
gaaaagtggg gaccccaggg aactcatcag tccccatctg ctgagagaag aggcctcaac    2760
ctagcacctt ctcctgccaa caaggccaag aagcgacctc tctttggaag cctgtcccct    2820
gctgaaaaga caccctaccc agggcctggg ctcagggtct ctggggagca atccctgact    2880
tgggggctgg gtggcccctc acagtctcaa aagagaaagg gtgacccctt ggtctccagg    2940
aaggagaaga agcagcattg tagccagtag                                     2970
```

<210> SEQ ID NO 3
<211> LENGTH: 990
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Asp Asp Arg Glu Asp Leu Val Tyr Gln Ala Lys Leu Ala Glu Gln
1               5                   10                  15

Ala Glu Arg Tyr Asp Glu Met Val Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
                85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
    210                 215                 220

Arg Asp Asn Leu Thr Leu Trp Thr Ser Asp Met Gln Gly Asp Ala Tyr
225                 230                 235                 240

Pro Ala Leu Gly Pro Gly Val Thr Ala Asn Pro Gly Thr Ser Leu Ser
                245                 250                 255

Val Phe Thr Ala Leu Pro Phe Thr Thr Pro Ala Pro Gly Pro Ala His
            260                 265                 270
```

-continued

```
Gly Pro Leu Leu Val Thr Ala Gly Ala Pro Pro Gly Pro Leu Val
            275                 280                 285
Leu Ser Thr Leu Pro Ser Thr Pro Leu Val Thr Glu Gln Asp Gly Cys
290                 295                 300
Gly Pro Ser Gly Ala Gly Ala Ser Asn Val Phe Val Gln Met Arg Thr
305                 310                 315                 320
Glu Val Gly Pro Val Lys Ala Ala Gln Ala Gln Thr Leu Val Leu Thr
                325                 330                 335
Gln Ala Ala Pro Leu Val Trp Gln Ala Pro Gly Ala Leu Cys Gly Gly
            340                 345                 350
Val Val Cys Pro Pro Pro Leu Leu Ala Ala Ala Pro Val Val Pro
        355                 360                 365
Val Met Ala Ala Gln Val Val Gly Gly Thr Gln Ala Cys Glu Gly Gly
    370                 375                 380
Trp Ser Gln Gly Leu Pro Leu Pro Pro Pro Pro Pro Ala Ala Gln
385                 390                 395                 400
Leu Pro Pro Ile Val Ser Gln Gly Asn Ala Gly Pro Trp Pro Gln Gly
                405                 410                 415
Ala His Gly Glu Gly Ser Leu Ala Ser Ser Gln Ala Lys Ala Pro Pro
            420                 425                 430
Asp Asp Ser Cys Asn Pro Arg Ser Val Tyr Glu Asn Phe Arg Leu Trp
        435                 440                 445
Gln His Tyr Lys Pro Leu Ala Arg Arg His Leu Pro Gln Ser Pro Asp
    450                 455                 460
Thr Glu Ala Leu Ser Cys Phe Leu Ile Pro Val Leu Arg Ser Leu Ala
465                 470                 475                 480
Arg Arg Lys Pro Thr Met Thr Leu Glu Glu Gly Leu Trp Arg Ala Met
                485                 490                 495
Arg Glu Trp Gln His Thr Ser Asn Phe Asp Arg Met Ile Phe Tyr Glu
            500                 505                 510
Met Ala Glu Lys Phe Leu Glu Phe Glu Ala Glu Glu Met Gln Ile
        515                 520                 525
Gln Lys Ser Gln Trp Met Lys Gly Pro Gln Cys Leu Pro Pro Ala
    530                 535                 540
Thr Pro Arg Leu Glu Pro Arg Gly Pro Ala Pro Glu Val Val Lys
545                 550                 555                 560
Gln Pro Val Tyr Leu Pro Ser Lys Ala Gly Lys Ala Pro Thr Ala
                565                 570                 575
Cys Leu Pro Pro Pro Arg Pro Gln Arg Pro Val Thr Lys Ala Arg Arg
            580                 585                 590
Pro Pro Pro Arg Pro His Arg Arg Ala Glu Thr Lys Ala Arg Leu Pro
        595                 600                 605
Pro Pro Arg Pro Gln Arg Pro Ala Glu Thr Lys Val Pro Glu Glu Ile
    610                 615                 620
Pro Pro Glu Val Val Gln Glu Tyr Val Asp Ile Met Glu Glu Leu Leu
625                 630                 635                 640
Gly Pro Ser Leu Gly Ala Thr Gly Glu Pro Glu Lys Gln Arg Glu Glu
                645                 650                 655
Gly Glu Val Lys Gln Pro Gln Glu Glu Asp Trp Thr Pro Pro Asp Pro
            660                 665                 670
Gly Leu Leu Ser Tyr Thr Asp Lys Leu Cys Ser Gln Lys Asp Phe Val
        675                 680                 685
Thr Lys Val Glu Ala Val Ile His Pro Gln Phe Leu Glu Glu Leu Leu
```

```
            690                 695                 700
Ser Pro Asp Pro Gln Met Asp Phe Leu Ala Leu Ser Gln Glu Leu Glu
705                 710                 715                 720

Gln Glu Glu Gly Leu Thr Leu Ala Gln Leu Val Glu Lys Arg Leu Leu
            725                 730                 735

Pro Leu Lys Glu Lys Gln His Ala Arg Ala Ala Pro Ser Arg Gly Thr
            740                 745                 750

Ala Arg Leu Asp Ser Ser Ser Lys Phe Ala Ala Gly Gln Gly Ala
            755                 760                 765

Glu Arg Asp Val Pro Val Pro Gln Gln Gly Val Gly Met Glu Thr Cys
            770                 775                 780

Pro Pro Gln Thr Thr Ala Arg Asp Ser Gln Gly Arg Gly Arg Ala His
785                 790                 795                 800

Thr Gly Met Ala Arg Ser Lys Asp Ser Val Val Leu Leu Gly Cys Gln
            805                 810                 815

Asp Ser Pro Gly Leu Arg Ala Ala Arg Pro Thr Ser Pro Pro Gln Asp
            820                 825                 830

His Arg Pro Thr Cys Pro Gly Val Gly Thr Lys Asp Ala Leu Asp Leu
            835                 840                 845

Pro Gly Gly Ser Pro Val Arg Glu Ser His Gly Leu Ala Gln Gly Ser
            850                 855                 860

Ser Glu Glu Glu Leu Pro Ser Leu Ala Phe Leu Leu Gly Ser Gln
865                 870                 875                 880

His Lys Leu Leu Pro Trp Trp Leu Pro Gln Ser Pro Val Pro Ala Ser
            885                 890                 895

Gly Leu Leu Ser Pro Glu Lys Trp Gly Pro Gln Gly Thr His Gln Phe
            900                 905                 910

Pro Ser Ala Glu Arg Arg Gly Leu Asn Leu Ala Pro Ser Pro Ala Asn
            915                 920                 925

Lys Ala Lys Lys Arg Pro Leu Phe Gly Ser Leu Ser Pro Ala Glu Lys
            930                 935                 940

Thr Pro His Pro Gly Pro Gly Leu Arg Val Ser Gly Glu Gln Ser Leu
945                 950                 955                 960

Thr Trp Gly Leu Gly Gly Pro Ser Gln Ser Gln Lys Arg Lys Gly Asp
            965                 970                 975

Pro Leu Val Ser Arg Lys Glu Lys Gln Arg Cys Ser Gln
            980                 985                 990

<210> SEQ ID NO 4
<211> LENGTH: 989
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
        35                  40                  45

Tyr Lys Asn Val Ile Gly Ala Arg Arg Ala Ser Trp Arg Ile Ile Ser
    50                  55                  60
```

```
Ser Ile Glu Gln Lys Glu Asn Lys Gly Glu Asp Lys Leu Lys
 65                  70                  75                  80

Met Ile Arg Glu Tyr Arg Gln Met Val Glu Thr Glu Leu Lys Leu Ile
                 85                  90                  95

Cys Cys Asp Ile Leu Asp Val Leu Asp Lys His Leu Ile Pro Ala Ala
                100                 105                 110

Asn Thr Gly Glu Ser Lys Val Phe Tyr Tyr Lys Met Lys Gly Asp Tyr
                115                 120                 125

His Arg Tyr Leu Ala Glu Phe Ala Thr Gly Asn Asp Arg Lys Glu Ala
                130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
                195                 200                 205

Leu Ser Glu Glu Ser Tyr Lys Asp Ser Thr Leu Ile Met Gln Leu Leu
                210                 215                 220

Arg Asp Asn Leu Thr Leu Trp Thr Ser Asp Met Gln Gly Asp Ala Tyr
225                 230                 235                 240

Pro Val Leu Gly Pro Gly Val Thr Ala Asn Pro Gly Thr Ser Leu Ser
                245                 250                 255

Val Phe Thr Ala Leu Pro Phe Thr Thr Pro Ala Pro Gly Pro Ala His
                260                 265                 270

Gly Pro Leu Leu Val Thr Ala Gly Ala Pro Gly Gly Pro Leu Val
                275                 280                 285

Leu Ser Thr Phe Pro Ser Thr Pro Leu Val Thr Glu Gln Asp Gly Cys
                290                 295                 300

Gly Pro Ser Gly Ala Gly Ala Ser Asn Val Phe Val Gln Met Arg Thr
305                 310                 315                 320

Glu Val Gly Pro Val Lys Ala Ala Gln Ala Gln Thr Leu Val Leu Thr
                325                 330                 335

Gln Ala Pro Leu Val Trp Gln Ala Pro Gly Ala Leu Cys Gly Gly Val
                340                 345                 350

Val Cys Pro Pro Pro Leu Leu Leu Ala Ala Ala Pro Val Val Pro Val
                355                 360                 365

Met Ala Ala Gln Val Val Gly Gly Thr Gln Ala Cys Glu Gly Gly Trp
370                 375                 380

Ser Gln Gly Leu Pro Leu Pro Pro Pro Pro Ala Ala Gln Leu
385                 390                 395                 400

Pro Pro Ile Val Ser Gln Gly Asn Ala Gly Pro Trp Pro Gln Gly Ala
                405                 410                 415

His Gly Glu Ser Ser Leu Ala Ser Ser Gln Ala Lys Ala Pro Pro Asp
                420                 425                 430

Asp Ser Cys Asn Pro Arg Ser Val Tyr Glu Asn Phe Arg Leu Trp Gln
                435                 440                 445

His Tyr Lys Pro Leu Ala Arg Arg His Leu Pro Gln Ser Pro Asp Thr
                450                 455                 460

Glu Ala Leu Ser Cys Phe Leu Ile Pro Val Leu Arg Ser Leu Ala Arg
465                 470                 475                 480

Arg Lys Pro Thr Met Thr Leu Glu Glu Gly Leu Trp Arg Ala Met Arg
```

-continued

```
                485                 490                 495
Glu Trp Gln His Thr Ser Asn Phe Asp Arg Met Ile Phe Tyr Glu Met
            500                 505                 510
Ala Glu Lys Phe Leu Glu Phe Glu Ala Glu Glu Met Gln Ile Gln
        515                 520                 525
Lys Ser Gln Trp Met Lys Gly Pro Gln Cys Leu Pro Pro Ala Thr
    530                 535                 540
Pro Arg Leu Glu Pro Arg Gly Pro Ala Pro Glu Val Val Lys Gln
545                 550                 555                 560
Pro Val Tyr Leu Pro Ser Lys Ala Gly Pro Lys Ala Pro Thr Ala Cys
                565                 570                 575
Leu Pro Pro Pro Arg Pro Gln Arg Pro Val Thr Lys Ala Arg Arg Pro
            580                 585                 590
Pro Pro Arg Pro His Arg Arg Ala Glu Thr Lys Ala Arg Leu Pro Pro
        595                 600                 605
Pro Arg Pro Gln Arg Pro Ala Glu Thr Lys Val Pro Glu Glu Ile Pro
    610                 615                 620
Pro Glu Val Val Gln Glu Tyr Val Asp Ile Met Glu Glu Leu Leu Gly
625                 630                 635                 640
Pro Ser Leu Gly Ala Thr Gly Glu Pro Glu Lys Gln Arg Glu Glu Gly
                645                 650                 655
Lys Val Lys Gln Pro Gln Glu Glu Asp Trp Thr Pro Asp Pro Gly
            660                 665                 670
Leu Leu Ser Tyr Ile Asp Lys Leu Cys Ser Gln Lys Asp Phe Val Thr
        675                 680                 685
Lys Val Glu Ala Val Ile His Pro Gln Phe Leu Glu Glu Leu Leu Ser
    690                 695                 700
Pro Asp Pro Gln Met Asp Phe Leu Ala Leu Ser Gln Asp Leu Glu Gln
705                 710                 715                 720
Glu Glu Gly Leu Thr Leu Ala Gln Leu Val Glu Lys Arg Leu Pro Pro
                725                 730                 735
Leu Lys Glu Lys Gln His Ala Arg Ala Ala Pro Ser Arg Gly Thr Ala
            740                 745                 750
Arg Leu Asp Ser Ser Ser Lys Phe Ala Ala Gly Gln Gly Ala Glu
        755                 760                 765
Arg Asp Val Pro Asp Pro Gln Gln Gly Val Gly Met Glu Thr Cys Pro
    770                 775                 780
Pro Gln Met Thr Ala Arg Asp Ser Gln Gly Arg Gly Arg Ala His Thr
785                 790                 795                 800
Gly Met Ala Arg Ser Glu Asp Ser Val Val Leu Leu Gly Cys Gln Asp
                805                 810                 815
Ser Pro Gly Leu Arg Ala Ala Trp Pro Thr Ser Pro Gln Asp His
            820                 825                 830
Arg Pro Thr Cys Pro Gly Val Gly Thr Lys Asp Ala Leu Asp Leu Pro
        835                 840                 845
Gly Gly Ser Pro Val Arg Glu Ser His Gly Leu Ala Gln Gly Ser Ser
    850                 855                 860
Glu Glu Glu Glu Leu Pro Ser Leu Ala Phe Leu Leu Gly Ser Gln His
865                 870                 875                 880
Lys Leu Leu Pro Trp Trp Leu Pro Gln Ser Pro Val Pro Ala Ser Gly
                885                 890                 895
Leu Leu Ser Pro Glu Lys Trp Gly Pro Gln Gly Thr His Gln Ser Pro
            900                 905                 910
```

```
Ser Ala Glu Arg Arg Gly Leu Asn Leu Ala Pro Ser Pro Ala Asn Lys
        915                 920                 925

Ala Lys Lys Arg Pro Leu Phe Gly Ser Leu Ser Pro Ala Glu Lys Thr
    930                 935                 940

Pro Tyr Pro Gly Pro Gly Leu Arg Val Ser Gly Glu Gln Ser Leu Thr
945                 950                 955                 960

Trp Gly Leu Gly Gly Pro Ser Gln Ser Gln Lys Arg Lys Gly Asp Pro
                965                 970                 975

Leu Val Ser Arg Lys Glu Lys Lys Gln His Cys Ser Gln
            980                 985

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgttacgtga atctgaca ctatggactt cagacatgca gggtgacgca t              51

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgttacgtga atctgaca ctatggactt cagacatgca gggtgacgca t              51

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gttacgtgat aatctgacac tatggacttc agacatgcag ggtgacgcat a            51

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gttacgtgat aatctgacac tatggacttc agacatgcag ggtgacgcat a            51

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
```
gttacgtgat aatctgacac tatggacttc agacatgcag ggtgacgcat a       51

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttacgtgata atctgacact atggacttca gacatgcagg gtgacgcata c       51

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttacgtgata atctgacact atggacttca gacatgcagg gtgacgcata c       51

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tacgtgataa tctgacacta tggacttcag acatgcaggg tgacgcatac c       51

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tacgtgataa tctgacacta tggacttcag acatgcaggg tgacgcatac c       51

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acgtgataat ctgacactat ggacttcaga catgcagggt gacgcatacc c       51

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgtgataatc tgacactatg gacttcagac atgcaaggtg acgcataccc a       51

```
<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtgataatct gacactatgg acttcagaca tgcagggtga cgcatacccα g          51

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgataatct gacactatgg acttcagaca tgcagggtga cgcatacccα g          51

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtgataatct gacactatgg acttcagaca tgcagggtga cgcatacccα g          51

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgataatct gacactatgg acttcagaca tgcagggtga cgcatacccα g          51

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtgataatct gacactatgg acttcagaca tgcagggtga cgcatacccα g          51

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgataatct gacactatgg acttcagaca tgcagggtga cgcatacccα g          51
```

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtgataatct gacactatgg acttcagaca tgcagggtga cgcataccca g         51

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgataatctg acactatgga cttcagacat gcagggtgac gcatacccag c         51

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgataatctg acactatgga cttcagacat gcagggtgac gcatacccag c         51

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgataatctg acactatgga cttcagacat gcagggtgac gcatacccag c         51

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tgataatctg acactatgga cttcagacat gcagggtgac gcatacccag c         51

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgataatctg acactatgga cttcagacat gcagggtgac gcatacccag c         51

<210> SEQ ID NO 28
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
gataatctga cactatggac ttcagacatg cagggtgacg catacccagc g          51

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
gataatctga cactatggac ttcagacatg cagggtgacg catacccagc g          51

<210> SEQ ID NO 30
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
ataatctgac actatggact tcagacatgc agggtgacgc atacccagcg c          51

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
ataatctgac actatggact tcagacatgc agggtgacgc atacccagcg c          51

<210> SEQ ID NO 32
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
taatctgaca ctatggactt cagacatgca gggtgacgca tacccagcgc t          51

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
aatctgacac tatggacttc agacatgcag ggtgacgcat agccagcgct g          51

<210> SEQ ID NO 34

```
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aatctgacac tatggacttc agacatgcag ggtgacgcat acccagcgct g            51

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atctggcact atggacttca gacatgcagg gtgacgcata cccagcgctg g            51

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atctgacact atggacttca gacatgcagg gtgacgcata cccagcgctg g            51

<210> SEQ ID NO 37
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atctgacact atggacttca gacatgcagg gtgacgcata cccagcgctg g            51

<210> SEQ ID NO 38
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tctgacacta tggacttcag acatgcaggg tgacgcatac ccagcgctgg g            51

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gacactatgg acttcagaca tgcagggtga cgcataccca gcgctgggac c            51

<210> SEQ ID NO 40
<211> LENGTH: 51
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gacactatgg acttcagaca tgcagggtga cgcatacccca gcgctgggac c           51

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gacactatgg acttcagaca tgcagggtga cgcatacccca gcgctgggac c           51

<210> SEQ ID NO 42
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
acactatgga cttcagacat gcagggtgac gcatacccag cgctgggacc g            51

<210> SEQ ID NO 43
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cactatggac ttcagacatg cagggtgacg catacccagc gctgggaccg g            51

<210> SEQ ID NO 44
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cactatggac ttcagacatg cagggtgacg catacccagc gctgggaccg g            51

<210> SEQ ID NO 45
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
actatggact tcagacatgc agggtgacgc atacccagcg ctgggaccgg g            51

<210> SEQ ID NO 46
<211> LENGTH: 51
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 46
actatggact tcagacatgc agggtgacgc atacccagcg ctgggaccgg g         51

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
actatggact tcagacatgc agggtgacgc atacccagcg ctgggaccgg g         51

<210> SEQ ID NO 48
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
actatggact tcagacatgc agggtgacgc atacccagcg ctgggaccgg g         51

<210> SEQ ID NO 49
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ctatggactt cagacatgca gggtgacgca tacccagcgc tgggaccggg c         51

<210> SEQ ID NO 50
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctatggactt cagacatgca gggtgacgca tacccagcgc tgggaccggg c         51

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctatggactt cagacatgca gggtgacgca tacccagcgc tgggaccggg c         51

<210> SEQ ID NO 52
<211> LENGTH: 51
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 52
ctatggactt cagacatgca gggtgacgca tacccagcgc tgggaccggg c            51

<210> SEQ ID NO 53
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tatggacttc agacatgcag ggtgacgcat acccagcgct gggaccgggc g            51

<210> SEQ ID NO 54
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
atggacttca gacatgcagg gtgacgcata cccagcgctg gaccgggcg t             51

<210> SEQ ID NO 55
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tggacttcag acatgcaggg tgacgcatac ccagcgctgg gaccgggcgt g            51

<210> SEQ ID NO 56
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggacttcaga catgcagggt gacgcatacc cagcgctggg accgggcgtg a            51

<210> SEQ ID NO 57
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggacttcaga catgcagggt gacgcatacc cagcgctggg accgggcgtg a            51

<210> SEQ ID NO 58
<211> LENGTH: 51
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 58
acttcagaca tgcagggtga cgcataccca gcgctgggac cgggcgtgac c                    51

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
acttcagaca tgcagggtga cgcataccca gcgctgggac cgggcgtgac c                    51

<210> SEQ ID NO 60
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
acttcagaca tgcagggtga cgcataccca gcgctgggac cgggcgtgac c                    51

<210> SEQ ID NO 61
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cttcagacat gcacggtgac gcatacccag cgctgggacc gggcgtgacc g                    51

<210> SEQ ID NO 62
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cagacatgca gggtgacgca tacccagcgc tgggaccggg cgtgaccgcg a                    51

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cagacatgca gggtgacgca tacccagcgc tgggaccggg cgtgaccgcg a                    51

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic
```

```
oligonucleotide

<400> SEQUENCE: 64
agacatgcag ggtgacgcat acccagcgct gggaccgggc gtgaccgcga a            51

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
agacatgcag ggtgacgcat acccagcgct gggaccgggc gtgaccgcga a            51

<210> SEQ ID NO 66
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
agacatgcag ggtgacgcat acccagcgct gggaccgggc gtgaccgcga a            51

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gacatgcagg gtgacgcata cccagcgctg ggaccgggcg tgaccgcgaa c            51

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
atgcagggtg acgcataccc agcgctggga ccgggcgtga ccgcgaaccc t            51

<210> SEQ ID NO 69
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
atgcagggtg acgcataccc agcgctggga ccgggcgtga ccgcgaaccc t            51

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 70
atgcagggtg acgcataccc agcgctggga ccgggcgtga ccgcgaaccc t    51

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atgcagggtg acgcataccc agcgctggga ccgggcgtga ccgcgaaccc t    51

<210> SEQ ID NO 72
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgcagggtga cgcataccca gcgctgggac cgggcgtgac cgcgaaccct g    51

<210> SEQ ID NO 73
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tgcagggtga cgcataccca gcgctgggac cgggcgtgac cgcgaaccct g    51

<210> SEQ ID NO 74
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tgcagggtga cgcataccca gcgctgggac cgggcgtgac cgcgaaccct g    51

<210> SEQ ID NO 75
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cagggtgacg catacccagc gctgggaccg ggcgtgaccg cgaaccctgg c    51

<210> SEQ ID NO 76
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
agggtgacgc atacccagcg ctgggaccgg gcgtgaccgc gaaccctggc a          51

<210> SEQ ID NO 77
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
agggtgacgc atacccagcg ctgggaccgg gcgtgaccgc gaaccctggc a          51

<210> SEQ ID NO 78
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agggtgaccc atacccagcg ctgggaccgg gcgcgaccgc gaaccctggc a          51

<210> SEQ ID NO 79
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gggtgacgca tacccagcgc tgggaccggg cgtgaccgcg aaccctggca c          51

<210> SEQ ID NO 80
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gtgacgcata cccagcgctg gaccgggcg tgaccgcgaa ccctggcacc t           51

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agaggctgag agagtcggag acacta                                     26

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tatggatgat cgagaggatc tggtg                                       25

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cagaactgga tacgctgagt gaagaa                                      26

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ctcatagaca ctcctggggt tacagg                                      26

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tcttgctggg ccttagcttt g                                           21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tatgttccag gaacctgttt a                                           21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
aaguucaggu cgauaugugc a                                           21

METHODS AND COMPOSITIONS FOR DIAGNOSING AND TREATING CANCER

CROSS REFERENCE TO RELATED APPLICATIONS

This application is a 35 U.S.C. §371 National Phase Entry Application of International Application No. PCT/US2012/072264 filed Dec. 31, 2012, which designates the U.S., and which claims benefit under 35 U.S.C. §119(e) of the U.S. Provisional Application No. 61/581,317, filed Dec. 29, 2011, the content of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 10, 2013, is named 04321407.txt and is 45,023 bytes in size.

TECHNICAL FIELD

The present disclosure relates generally to assays, methods, systems and compositions for diagnosing and treating cancer in a subject.

BACKGROUND

The 14-3-3 protein family includes seven highly conserved dimeric isoforms (β, γ, ε, ζ, η, σ, and τ) that are expressed in all eukaryotic cells (1). Through interaction with phospho-serine or phospho-threonine motifs, 14-3-3 can regulate diverse cellular functions, including signal transduction, cytoskeletal configuration, metabolism, differentiation, survival, and transcription (2). 14-3-3 proteins are implicated in tumorigenesis (3, 4), as a tumor suppressor in the case of 14-3-3σ (SFN), and as a putative oncoprotein in the case of 14-3-3ζ (YWHAZ). 14-3-3σ expression is inhibited in premalignant and malignant cells (5), and loss of 14-3-3σ results in polyploidy and failure to maintain G2/M cell-cycle arrest after DNA damage through cytoplasmic sequestration of CDC2/cyclin B1 (6, 7). 14-3-3ζ expression is up-regulated in various cancers (8), and it induces epithelial-mesenchymal transition by activation of TGF-β/Smads and inhibits apoptosis in anoikic cells, thereby potentiating tumor invasion and metastasis (9, 10).

Endometrial stromal sarcoma (ESS) is a type of uterine sarcoma that, in its low-grade form, contains JAM fusions with various polycomb complex proteins (SUZ12, PHF1, and EPC1) (11, 12). In contrast, some ESS are histologically high grade, and these tumors typically lack JAZF1 rearrangement. The genetic basis for high-grade ESS is undefined.

SUMMARY

The present invention is based, in part, on inventors' discovery of a transforming 14-3-3 oncoprotein. 14-3-3 proteins are ubiquitously expressed regulators of various cellular functions, including proliferation, metabolism, and differentiation, and altered 14-3-3 expression is associated with development and progression of cancer. The inventors used a combination of cytogenetics and next-generation sequencing to identify YWHAE-FAM22A/B genetic fusion as a frequent genetic event that is specific for high-grade ESS. The inventors further demonstrated the transforming properties of the fusion protein and characterized the clinicopathologic significance of YWHAE-FAM22A/B genetic fusion. The discovery of this unique oncogenic mechanism has biologic, diagnostic, and therapeutic implications.

Accordingly, in one aspect provided herein is a method of identifying a subject suitable for endometrial stromal sarcoma (ESS) treatment. Generally, the method comprises detecting the presence of a YWHAE-FAM22 fusion protein or a nucleic acid encoding the same in a biological sample taken from the subject. Presence of the fusion protein or the nucleic acid encoding the fusion protein indicating that the individual should undergo anti-cancer treatment, e.g., treatment for endometrial stromal sarcoma.

After a subject is identified as needing anti-cancer treatment, the subject can be treated with an anti-cancer treatment. Thus, in another aspect provided herein is method of treating endometrial stromal sarcoma in subject in need thereof, the method comprising administering an anti-cancer therapy to the subject, wherein the subject expresses a YWHAE-FAM22 fusion protein or a nucleic acid encoding the same. In some embodiments, the method comprising: assaying a biological sample from a subject for presence of the YWHAE-FAM22 fusion protein or a nucleic acid encoding the same and administering an anti-cancer therapy to the subject if the YWHAE-FAM22 fusion protein or a nucleic acid encoding the same is detected in the sample.

Also provided herein is an isolated sample from a subject, wherein the sample comprises a YWHAE-FAM22 fusion protein or a nucleic acid encoding the same. In some embodiments, the sample further comprises a first reagent that can bind with the fusion protein or the nucleic acid.

The invention also provides an isolated nucleic acid encoding the YWHAE-FAM22 fusion protein described herein. Additionally, the invention also provides an isolated YWHAE-FAM22 fusion protein. In some embodiments, the YWHAE-FAM22 fusion protein or the nucleic acid encoding the same is from a biological sample taken from a subject.

Further provided herein is a composition, comprising: (i) a YWHAE-FAM22 fusion protein or a nucleic acid encoding the same; and (ii) a reagent that binds with the fusion protein or the nucleic acids. In some embodiments, the reagent is adapted to produce a signal so as to detect presence of the fusion protein or the nucleic acid in the sample.

Without limitations, the FAM22 protein portion of the fusion protein can be any FAm22 family member, such as FAM22A, FAM22B, FAM22C, FAM22D or FAM22E. In embodiments of the various aspects described herein, the YWHAE-FAM22 fusion protein can be a YWHAE-FAM22A or YWHAE-FAM22B fusion protein, or can be a YWHAE-FAM22 fusion involving other FAM22 family members, including FAM22C, FAM22D and FAM22E.

In embodiments of the various aspects described herein, the nucleic acid encoding the YWHAE-FAM22 fusion protein comprises the nucleotide sequence SEQ ID NO:1 or SEQ ID No: 2.

In embodiments of the various aspects described herein, the YWHAE-FAM22 fusion protein comprises the amino acid sequence SEQ ID NO: 3 or SEQ ID NO: 4.

In some embodiments, the biological sample comprises endometrial cells.

Also provided herein is a detection assay, the assay comprising detecting presence of a YWHAE-FAM22 fusion protein or a nucleic acid encoding the same in a biological sample taken from a subject. In some embodiments, the subject is suspected of having a cancer.

The assays, methods, systems, compositions, and kits described herein can be used for classifying endometrial cancer in a subject. As discussed herein, subjects expressing the YWHAE-FAM22 fusion protein have uterine sarcomas that are genetically, histologically, and clinically distinct from other forms of uterine sarcomas.

BRIEF DESCRIPTION OF THE DRAWINGS

FIG. 1A, high-grade ESS G-banded partial karyotype showing a balanced translocation, t(10;17). Arrows indicate the translocation breakpoints. FIG. 1B, split-apart view of YWHAE-flanking BACs, RP11-220I2 (red) and RP11-100F18 (green), demonstrates YWHAE rearrangement in an ESS1 cell. FIG. 1C, deFuse analysis of ESS1 whole-transcriptome paired-end sequencing (Illumina) identifies split-read transcript sequences in which YWHAE exon 5 is fused to FAM22A exon 2. The conserved 14-3-3 protein-binding domains are encoded by exons 2 and 4 of YWHAE (denoted by the lines on exons 2 and 4 of YWHAE). Split-read nucleotide sequences are SEQ ID NO: 5 to SEQ ID NO: 80 in order of appearance (from top to bottom).

FIG. 1E, RT-PCR using YWHAE exon 1 (lanes 1 and 2) and exon 5 (lane 3) forward primers with FAM22A/B/E exon 2 reverse primer in two t(10;17)-bearing ESS. Sequence analyses showed YWHAE-FAM22A and YWHAE-FAM22B, respectively, in ESS1 and ESS3. The top, middle, and bottom arrows indicate 1,650-, 1,000-, and 650-Kb markers, respectively. FIG. 1E, schematic of YWHAE on chromosome 17 (Chr 17) and the two alternative fusion partners, FAM22A and FAM22B on chromosome 10 (Chr 10), with the direction of transcription indicated by arrows.

FIG. 2A, 3T3 cells transfected (Lipofectamine) with YWHAE-FAM22A pcDNA3 had increased cell viability (CellTiter Glo luminescence assay) at various plating densities compared with 3T3 cells transfected with YWHAE pcDNA3. Error bars indicate SEs. FIGS. 2B and 2C, 3T3 cells transfected (Lipofectamine) with YWHAE-FAM22A pcDNA3 migrated more rapidly than 3T3 cells transfected with YWHAE pcDNA3, as shown by assays for quantitative cell migration (FIG. 2B) and wound healing (FIG. 2C). Error bars indicate SEs. FIG. 2D, structural modeling of YWHAE-FAM22A (including the protein sequences encoded by exons 1 to ~5 of YWHAE and FAM22A exon 2) based on the X-ray crystal structure of 14-3-3. Heterodimer of YWHAE-FAM22 bound to native YWHAE is depicted in stick representation. The green and cyan chains indicate YWHAE (14-3-3ε) sequences with the purple helix representing the first part of FAM22A. This model shows that YWHAE fusion to FAM22 is unlikely to interfere with YWHAE dimerization or phosphopeptide binding.

FIGS. 3A and 3B show that oncogenic fusion to FAM22 enables aberrant nuclear localization of YWHAE. FIG. 3A, endogenous YWHAE-FAM22A is predominantly nuclear, whereas native YWHAE is predominantly cytoplasmic. FOXO3A and poly(ADP-ribose) polymerase (PARP) are nuclear localization controls, whereas GAPDH is a cytoplasmic control. FIG. 3B, induced YWHAE-FAM22A expression is nuclear in 293T cells, as shown by FLAG immunoprecipitation (Upper) and YWHAE immunohistochemistry (Lower) after transient expression of FLAG-tagged YWHAE-FAM22A pcDNA3 construct. In contrast to the predominantly cytoplasmic staining (and absent nuclear staining) seen in nontransfected 293T cells (representing wild-type YWHAE), YWHAE immunostaining in YWHAE-FAM22A-expressing 293T cells showed the presence of nuclear staining, indicating nuclear localization of the fusion protein.

FIG. 4A, YWHAE-FAM22 ESS, in contrast to JAZF1-SUZ12 ESS, has high-grade histology, with larger and more irregular nuclei and increased mitotic activity. FIG. 4B, 3' sequencing gene-expression profiling with unsupervised hierarchical clustering demonstrates distinct gene-expression signatures between YWHAE-FAM22 ESS (YWHAE ESS), JAZF1-rearranged ESS (JAZF1 ESS), and uterine leiomyosarcoma (LMS). FIG. 4C, patients with YWHAE-FAM22 ESS present with higher International Federation of Gynecology and Obstetrics (FIGO) stage disease compared with patients with JAZF1-rearranged ESS. FIG. 4D, YWHAE-FAM22 ESS (average follow-up period of 3.5 y) more frequently recurs compared with JAZF1-rearranged ESS (average follow-up period of 10 y). NED, no evidence of disease; AWD, alive with disease; DOD, died of disease.

FIG. 5A, FISH studies using BAC probes flanking the breakpoint region in 10q23.2 in ESS1 and 10q22.3 in ESS12. The 10q breakpoints were mapped to a 725-Kb region (flanked by BACs RP11-1005L9 and RP11-210E13) in 10q23.2 and a 600-Kb region (flanked by BACs RP11-715A21 and RP11-668E21) in 10q22.3. FIG. 5B (upper), whole-genome sequencing (20× coverage, blue trace) of a normal human DNA, demonstrating that the FISH-mapped ESS 10q22.3 and 10q23.2 translocation breakpoints (red arrows) are in localized regions of extremely poor sequence mappability. FIG. 5B (lower), depicts higher-resolution view of the 10q23.2 breakpoint region showing locations of the FAM22A and FAM22D genes. A similar organization also applies to the FAM22B and FAM22E genes in the 10q22.3 breakpoint region.

Figure 1:
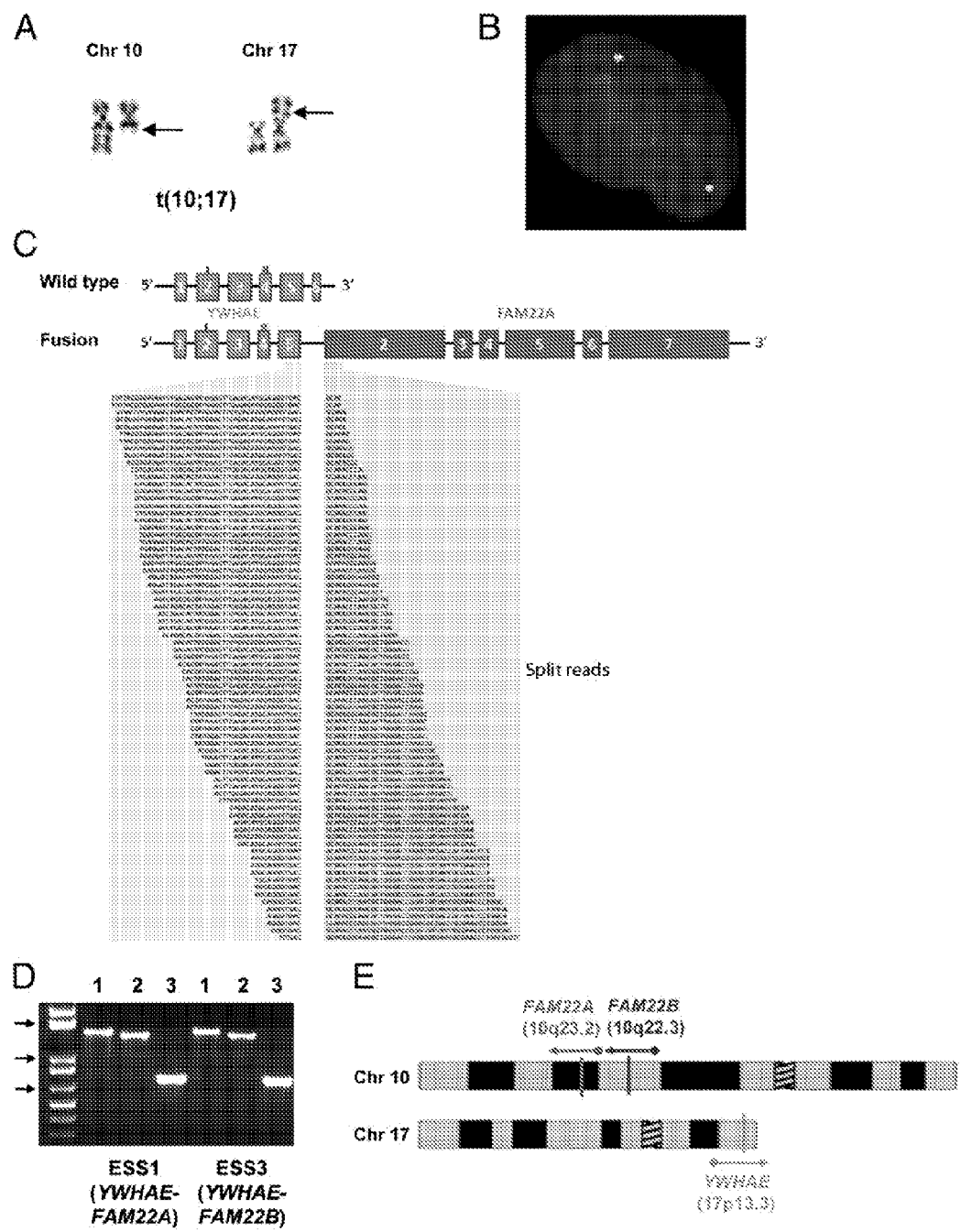
FIGS. 1A-1E show the genomic mechanisms for the 14-3-3 fusion oncogene in endometrial cancer.

DETAILED DESCRIPTION 14-3-3 proteins are ubiquitously expressed regulators of various cellular functions, including proliferation, metabolism, and differentiation, and altered 14-3-3 expression is associated with development and progression of cancer. The inventors have now discovered a transforming 14-3-3 oncoprotein. The inventors discovered the transforming 14-3-3 oncoprotein through cytogenetics and whole-transcriptome sequencing analysis as a highly recurrent genetic mechanism in a clinically aggressive form of uterine sarcoma: high-grade endometrial stromal sarcoma (ESS). As described herein, the 14-3-3 oncoprotein results from a t(10;17) genomic rearrangement, leading to fusion between 14-3-3ε (YWHAE) and either of two nearly identical FAM22 family members (FAM22A or FAM22B). Expression of YWHAE-FAM22 fusion oncoproteins was demonstrated by immunoblot in t(10;17)-bearing frozen tumor and cell line samples. YWHAE-FAM22 fusion gene knockdowns were performed with shRNAs and siRNAs targeting various FAM22A exons in an t(10;17)-bearing ESS cell line (ESS1): Fusion protein expression was inhibited; with corresponding reduction in cell growth and migration. YWHAE-FAM22 maintains a structurally and functionally intact 14-3-3e (YWHAE) protein-binding domain, which is directed to the nucleus by a FAM22 nuclear localization sequence. In contrast to classic ESS, harboring JAZF1 genetic fusions, YWHAE-FAM22 ESS display high-grade histologic features, a distinct gene-expression profile, and a more aggressive clinical course. Fluorescence in situ hybridization analysis demonstrated absolute specificity of YWHAE-FAM22A/B genetic rearrangement for high-grade ESS, with no fusions detected in other uterine and nonuterine mesenchymal tumors (55 tumor types, n=827). These discoveries reveal diagnostically and therapeutically relevant models for characterizing aberrant 14-3-3 oncogenic functions. Based on the inventors' discovery of the transforming 14-3-3 oncoprotein, provided here are methods and compositions for diagnosing and treating cancer, e.g., high-grade endometrial stromal sarcoma.

Accordingly, in one aspect, the invention relates to a method of assessing endometrial stromal sarcoma status in a subject which involves the step of assaying a biological sample derived from the individual for the presence of fusion protein or a nucleic acid encoding the fusion protein. In particular, the invention relates to a method of assisting in clinical decision making during screening of a subject (e.g., a patient) for identifying subjects suitable for endometrial stromal sarcoma treatment, which involves the step of assaying a biological sample derived from the individual for the presence of a fusion protein or a nucleic acid encoding the fusion protein. Presence of the fusion protein or the nucleic acid encoding the fusion protein indicating that the individual should undergo anti-cancer treatment, e.g., treatment for endometrial stromal sarcoma. Without limitations, a fusion protein or the nucleic acid can be detected in a sample directly, by assaying for the fusion protein or the nucleic acid, or indirectly by assaying for a reagent that binds with the fusion protein or the nucleic acid. Exemplary such methods are described herein below.

As used herein, the term "fusion protein" or grammatical equivalents thereof is meant a protein composed of a plurality of polypeptide components, that while typically unjoined in their native state, are joined by their respective amino and carboxyl termini through a peptide linkage to form a single continuous polypeptide. Fusion proteins can be a combination of two, three or even four or more different proteins.

In some embodiments, the fusion protein comprises a portion of YWHAE protein and a portion of a FAM22 protein. Without limitations the FAM22 protein can be any member of the FAM22 family. For example, the FAM22 protein can be, but is not limited to, FAM22A, FAM22B, FAM22C, FAM22D, or FAM22E. In some embodiments, the FAM22 protein is FAM22A or FAM22B protein. In other embodiments, based on very high sequence conservation among the FAM22 family members, the FAM22 protein is FAM22C, FAM22D, or FAM22E.

In some embodiments, the N-terminal of the fusion protein comprises a portion of the YWHAE protein and the C-terminal of the fusion protein comprises a portion of the FAM22 protein.

In some embodiments, the nucleic acid encoding the fusion protein comprises exon 5 of the gene encoding the YWHAE protein.

In some embodiments, the nucleic acid encoding the fusion protein comprises exon 2 of the gene encoding a FAM22 (e.g., FAM22A or FAM22B) protein.

In some embodiments, in the nucleic acid encoding the fusion protein, exon 5 of the gene encoding the full length YWHAE protein is linked to exon 2 of the gene encoding the FAM22 protein.

In some embodiments, the nucleic acid encoding the YWHAE-FAM22 fusion protein comprises the nucleotide sequence of SEQ ID NO: 1 or SEQ ID NO: 2.

In some embodiments, the fusion protein comprises the amino acid sequence of SEQ ID NO: 3 or SEQ ID NO: 4.

Accordingly, in one aspect provided herein is a method of identifying a subject suitable for endometrial stromal sarcoma treatment. The method comprises detecting the presence of a YWHAE-FAM22 fusion protein or a nucleic acid encoding the same in a biological sample taken from the subject. Presence of the fusion protein or the nucleic acid encoding the fusion protein indicating that the individual should undergo anti-cancer treatment, e.g., treatment for endometrial stromal sarcoma.

As used herein, the term "biological sample" refers to a sample obtained from an organism or from components (e.g., cells) of an organism. The sample can be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological sample can be a respiratory sample, bone marrow aspirations, cerebrospinal fluid, urine or blood fluid. Blood fluid means blood, serum or plasma. Biological samples can also include sections of tissues such as frozen sections taken for histological purposes. The term "biological sample" also includes untreated or pre-treated (or pre-processed) biological samples.

In some embodiments, the biological sample can be a biological fluid, including, but not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In other embodiments, the biological sample can include cell lysate and fractions thereof. For example, cells (such as red blood cells, platelets, white blood cells and any cells circulating in the biological fluid described herein) can be harvested and lysed to obtain a cell lysate. In some embodiments, a biological sample is a blood sample. In some embodiments, a biological sample is a plasma sample. In some embodiments, a biological sample is a saliva sample. In some embodiments, a biological sample is a buccal sample. In some embodiments, a biological sample is a urine sample.

In some embodiments, the sample is from a resection, biopsy, or core needle biopsy. In addition, fine needle aspirate samples can be used.

In some embodiments, the biological sample comprises endometrial cells. The sample can be obtained by removing a sample of cells from a subject, but can also be accomplished by using previously isolated cells (e.g. isolated by another person). In addition, the biological sample can be freshly collected or a previously collected sample.

Samples can also be either paraffin-embedded or frozen tissue. Accordingly, in some embodiments, the biological sample can be a frozen biological sample, e.g., a frozen tissue or fluid sample such as urine, blood, serum or plasma. The frozen sample can be thawed before employing the methods, assays and systems described herein. After thawing, a frozen sample can be centrifuged before being subjected to methods, assays and systems described herein.

In some embodiments, the test sample or the biological sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample. The skilled artisan is well aware of methods and processes for collecting and/or preprocessing of different types of biological samples.

Methods for assaying a biological sample for the presence a protein, e.g. a fusion protein are well known to those skilled in the art. Such methods include, but are not limited to, immunoassays that include, but are not limited to, immunoprecipitation assays, ELISA-based assays, radioimmunoassay, "sandwich" immunoassays, immunodiffusion assays, agglutination assays, and western blot assays. Similarly, methods for assaying a biological sample for the presence of a nucleic acid are also well known in those skilled in the art. Such methods include, but are not limited to, restriction enzyme digestion, probe hybridization, primer extension, sequence specific amplification, sequencing, 5' nuclease digestion, molecular beacon assays, oligonucleotide ligation assays, and Northern Blot. Exemplary methods for detecting the fusion protein or the nucleic acid encoding the same are described in detail below.

Without limitations, substantially any method of detecting a nucleic acid can be used in assaying a sample for presence of the nucleic acid encoding the fusion protein. Such methods, include, but are not limited to, restriction enzyme digestion, probe hybridization, primer extension, sequence specific amplification, sequencing, 5' nuclease digestion, molecular beacon assays, and oligonucleotide ligation assays.

In some embodiments, detection of the nucleic acid in the sample is by DNA sequencing. Exemplary DNA sequencing methods include, but are not limited to, Maxam-Gilbert sequencing; Chain-termination methods; advanced methods and de novo sequencing, such as shotgun sequencing, bridge PCR, and the like), Next-generation methods, such as Massively Parallel Signature Sequencing (MPSS), Polony sequencing, 454 pyrosequencing, Illumina (Solexa) sequencing, SOLiD sequencing, Ion semiconductor sequencing, DNA nanoball sequencing, Heliscope single molecule sequencing, Single molecule real time (SMRT) sequencing), and methods such as Nanopore DNA sequencing, Sequencing by hybridization, Sequencing with mass spectrometry, Microfluidic Sanger sequencing, Microscopy-based techniques, RNAP sequencing, in vitro virus high-throughput sequencing, and the like.

Methods for detecting nucleic acids can include the use of distinct oligonucleotide probes, for example oligonucleotides complementary to a portion of the nucleotide sequence of the nucleic acid of interest, e.g., a nucleic acid encoding the fusion protein. The probe is preferably a DNA oligonucleotide having a length in the range from about 20 to about 40 nucleotide residues, preferably from about 20 to about 30 nucleotide residues, and more preferably having a length of about 25 nucleotide residues.

In some embodiments, the probe is rendered incapable of extension by a PCR-catalyzing enzyme such as Taq polymerase, for example by having a fluorescent probe attached at one or both ends thereof. Although non-labeled oligonucleotide probes can be used in the kits and methods described herein, the probes are preferably detectably labeled. Exemplary labels include radionuclides, light-absorbing chemical moieties (e.g. dyes), fluorescent moieties, and the like. Preferably, the label is a fluorescent moiety, such as 6-carboxyfluorescein (FAM), 6-carboxy-4,7,2',7'-tetrachlorofluoroscein (TET), rhodamine, JOE (2,7-dimethoxy-4,5-dichloro-6-carboxyfluorescein), HEX (hexachloro-6-carboxyfluorescein), or VIC.

In some embodiments, the probe can comprise both a fluorescent label and a fluorescence-quenching moiety such as 6-carboxy-N,N,N',N'-tetramethylrhodamine (TAMRA), or 4-(4'-dimethlyaminophenylazo)benzoic acid (DABCYL). When the fluorescent label and the fluorescence-quenching moiety are attached to the same oligonucleotide and separated by no more than about 40 nucleotide residues, and preferably by no more than about 30 nucleotide residues, the fluorescent intensity of the fluorescent label is diminished. When one or both of the fluorescent label and the fluorescence-quenching moiety are separated from the oligonucleotide, the intensity of the fluorescent label is no longer diminished. Preferably, the probe for use in the assays, methods, systems and kits described herein can have a fluorescent label attached at or near (i.e. within about 10 nucleotide residues of) one end of the probe and a fluorescence-quenching moiety attached at or near the other end.

Degradation of the probe by a PCR-catalyzing enzyme releases at least one of the fluorescent label and the fluorescence-quenching moiety from the probe, thereby discontinuing fluorescence quenching and increasing the detectable intensity of the fluorescent labels. Thus, cleavage of the probe (which, as discussed above, is correlated with complete complementarity of the probe with the target portion) can be detected as an increase in fluorescence of the assay mixture.

If detectably different labels are used, more than one labeled probe can be used. For example, the assay mixture can contain a first probe which is complementary to a portion of the nucleic acid that encodes the YWHAE portion of the fusion protein and to which a first label is attached, and a second probe which is complementary to a portion of the nucleic acid that encodes the FAM22 portion of the fusion protein. When two probes are used, the probes are detectably different from each other, having, for example, detectably different size, absorbance, excitation, or emission spectra, radiative emission properties, or the like. For example, a first probe can have FAM and TAMRA attached at or near opposite ends thereof. The first probe can be used in the methods, assays, systems and kits described herein together with a second probe which has TET and TAMRA attached at or near opposite ends thereof. Fluorescent enhancement of FAM (i.e. effected by cessation of fluorescence quenching upon degradation of the first probe by Taq polymerase) can be detected at one wavelength (e.g. 518 nanometers), and fluorescent enhancement of TET (i.e. effected by cessation of fluorescence quenching upon degradation of the second probe by Taq polymerase) can be detected at a different wavelength (e.g. 582 nanometers).

In some embodiments, the nucleic acid detection can comprise amplifying the target nucleic acid. This can be accomplished using a pair of amplification primers for amplifying a reference region of the nucleic acid encoding the fusion protein. In some embodiments, the reference region comprises the a portion of the nucleic acid encoding the YWHAE portion of the fusion protein and a portion of the nucleic acid encoding the FAM22 portion of the fusion protein. Thus, in some embodiments, a first amplification primer is complementary or homologous to a portion of the nucleic acid that encodes the YWHAE portion of the fusion protein and is complementary or homologous to a portion of the nucleic acid that encodes the FAM22 portion of the fusion protein.

In some embodiments, the primer extension reaction and analysis is performed using PYROSEQUENCING™ (Uppsala, Sweden) which essentially is sequencing by synthesis. A sequencing primer is first hybridized to a single stranded, PCR amplified DNA template from the individual, and incubated with the enzymes, DNA polymerase, ATP sulfurylase, luciferase and apyrase, and the substrates, adenosine 5' phosphosulfate (APS) and luciferin. One of four deoxynucleotide triphosphates (dNTP), for example, corresponding to the nucleotide present in the mutation or polymorphism, is then added to the reaction. DNA polymerase catalyzes the incorporation of the dNTP into the standard DNA strand. Each incorporation event is accompanied by release of pyrophosphate (PPi) in a quantity equimolar to the amount of incorporated nucleotide. Consequently, ATP sulfurylase converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a PYROGRAM™. Each light signal is proportional to the number of nucleotides incorporated and allows a clear determination of the presence or absence of, for example, the mutation or polymorphism. Thereafter, apyrase, a nucleotide degrading enzyme, continuously degrades unincorporated dNTPs and excess ATP. When degradation is complete, another dNTP is added which corresponds to the dNTP present in for example the selected SNP. Addition of dNTPs is performed one at a time. Deoxyadenosine alfa-thio triphosphate (dATPS) is used as a substitute for the natural deoxyadenosine triphosphate (dATP) since it is efficiently used by the DNA polymerase, but not recognized by the luciferase. For detailed information about reaction conditions for the PYROSEQUENCING, see, e.g. U.S. Pat. No. 6,210,891, content of which is incorporated herein by reference in its entirety.

Alternatively, an INVADER® assay can be used (Third Wave Technologies, Inc (Madison, Wis.)). This assay is generally based upon a structure-specific nuclease activity of a variety of enzymes, which are used to cleave a target-dependent cleavage structure, thereby indicating the presence of specific nucleic acid sequences or specific variations thereof in a sample (see, e.g. U.S. Pat. No. 6,458,535). For example, an INVADER® operating system (OS), provides a method for detecting and quantifying DNA and RNA. The INVADER® OS is based on a "perfect match" enzyme-substrate reaction. The INVADER® OS uses proprietary CLEAVASE® enzymes (Third Wave Technologies, Inc (Madison, Wis.)), which recognize and cut only the specific structure formed during the INVADER® process. Unlike the PCR-based methods, the INVADER® OS relies on linear amplification of the signal generated by the INVADER® process, rather than on exponential amplification of the target.

In the INVADER® process, two short DNA probes hybridize to the target to form a structure recognized by the CLEAVASE® enzyme. The enzyme then cuts one of the probes to release a short DNA "flap." Each released flap binds to a fluorescently-labeled probe and forms another cleavage structure. When the CLEAVASE® enzyme cuts the labeled probe, the probe emits a detectable fluorescence signal.

Another method to determine sequence of a nucleic acid is using "gene chips". The use of microarrays comprising a multiplicity of sequences is becoming increasingly common in the art. Accordingly, a microarray having at least one oligonucleotide probe, as described above, appended thereon, can be used for interrogating the presence of a specific nucleic acid sequence in a sample. Probes can be affixed to surfaces for use as "gene chips." Such gene chips can be used to detect presence of a nucleic acid in a sample by a number of techniques known to one of skill in the art. In one technique, oligonucleotides are arrayed on a gene chip for determining the nucleotide sequence by the sequencing by hybridization approach, such as that outlined in U.S. Pat. Nos. 6,025,136 and 6,018,041. The probes can also be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayyem et al. U.S. Pat. No. 5,952,172 and by Kelley, S. O. et al. (1999) Nucleic Acids Res. 27:4830-4837.

In some embodiments, presence of the nucleic acid in the sample can be done using Real-Time PCR. Real time PCR is an amplification technique that can be used to determine expression levels of mRNA corresponding to a protein of interest. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA can be extracted from a biological sample, e.g. a blood sample (such as white blood cells and/or platelets) and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes can be obtained commercially from, for example, Perkin Elmer/Applied Biosystems (Foster City, Calif.). To quantitate the amount of the specific nucleic acid of interest in a sample, a standard curve is generated using a control. Standard curves can be generated using the Ct values determined in the real-time PCR, which are related to the initial concentration of the nucleic acid of interest used in the assay. Standard dilutions ranging from $10^1$-$10^6$ copies of the gene of interest are generally sufficient. In addition, a standard curve is generated for the control sequence. This permits standardization of initial content of the nucleic acid of interest in a test sample to the amount of control for comparison purposes.

Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

The TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, Perkin-Elmer).

In another embodiment, detection of RNA transcripts can be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

Detection of RNA transcripts can further be accomplished using known amplification methods. For example, mRNA can be reverse-transcribed into cDNA followed by polymerase chain reaction (RT-PCR); or use a single enzyme for both steps as described in U.S. Pat. No. 5,322,770, or reverse transcribe mRNA into cDNA followed by symmetric gap lipase chain reaction (RT-AGLCR) as described by R. L. Marshall, et al., PCR Methods and Applications 4: 80-84 (1994). One suitable method for detecting enzyme mRNA transcripts is described in reference Pabic et. al. Hepatology, 37(5): 1056-1066, 2003, content of which is herein incorporated by reference.

In situ hybridization visualization can also be employed, wherein a radioactively labeled antisense RNA probe is hybridized with nucleic acid encoding the fusion protein in a test sample, washed, cleaved with RNase and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used.

Alternatively, mRNA expression can be detected on a DNA array, chip or a microarray. Oligonucleotides corresponding to enzyme are immobilized on a chip which is then hybridized with labeled nucleic acids of a test sample obtained from a patient. Positive hybridization signal is obtained with the sample containing biomarker transcripts. Methods of preparing DNA arrays and their use are well known in the art. (See, for example U.S. Pat. Nos: 6,618, 6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference). Serial Analysis of Gene Expression (SAGE) can also be performed (See for example U.S. Patent Application 20030215858).

In some embodiments, the assay for detection of the nucleic acid comprises a step of amplifying the nucleic acid before the detection step. This can be accomplished for example using a pair of primers that amplify a portion of the nucleic acid comprising a portion that encodes at least a part of the YWHAE portion of the fusion protein and at least a part of the FAM22 portion of the FAM22. For example, the pair of primers can be chosen as to amplify a region of the nucleic acid comprising at least nucleotides 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714 or 715 to 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 768, 769, 760, 761, 762, 763, 764, or 765 of SEQ ID NO: 1 or SEQ ID NO: 2.

In some embodiments, first primer in the primer pair is selected from SEQ ID NO: 81 (5'-AGAGGCTGAGA-GAGTC GGAGACA CTA-3'), SEQ ID NO: 82 (5'-TATG-GATGATCGAGAGGATCTGGTG-3'); and SEQ ID NO: 83 (5'-CAGAAC TGGATACGC TGAGT GAAGAA-3') and the second primer in the primer pair is SEQ ID NO: 84 (5'-CTCATAGACACT CCTGG GGTTACAGG-3').

After amplification, the amplified nucleic acid can be subjected to DNA sequencing analysis. Exemplary DNA sequencing methods available to the skilled artisan and amenable to the assays, methods, systems and compositions described herein are described elsewhere herein. In some embodiments, sequencing is using the BigDye Terminator Ready Reaction Cycle Sequencing (Applied Biosystems).

By way of example only, presence of the fusion protein in the sample can be determined by contacting the test sample with an antibody-based binding moiety that specifically binds to the fusion protein or to a fragment thereof. Formation of the antibody-protein complex can then be detected by a variety of methods known in the art.

As used herein, the term "antibody-based binding moiety" or "antibody" can include immunoglobulin molecules and immunologically active determinants of immunoglobulin molecules, e.g., molecules that contain an antigen binding site which specifically binds to the fusion protein. The term "antibody-based binding moiety" is intended to include whole antibodies, e.g., of any isotype (IgG, IgA, IgM, IgE, etc), and includes fragments thereof which are also specifically bind with the fusion protein or a fragment thereof. Antibodies can be fragmented using conventional techniques. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-based binding moiety" includes polyclonal, monoclonal, or other purified preparations of antibodies and recombinant antibodies. The term "antibody-based binding moiety" is further intended to include humanized antibodies, bispecific antibodies, and chimeric molecules having at least one antigen binding determinant derived from an antibody molecule. In some embodiments, the antibody-based binding moiety can be detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of the fusion protein in test samples correlate to the intensity of the signal emitted from the detectably labeled antibody.

In some embodiments, the antibody-based binding moiety can be detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies against the fusion protein can include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by autoradiography. Isotopes which are particularly useful for the purpose of detection are $^3$H, $^{131}$I, $^{35}$S, $^{14}$C, and $^{125}$I.

It is also possible to label an antibody with a fluorescent compound. When the fluorescently labeled antibody is exposed to light of the proper wavelength, its presence can then be detected due to fluorescence. Examples of the most commonly used fluorescent labeling compounds include, but not limited to, CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of chemiluminescent labeling compounds can include, but not limited to, luminol, luciferin, isoluminol, theromatic acridinium ester, imidazole, acridinium salt and oxalate ester.

Without limitations, presence of fusion protein in the biological sample can be detected by immunoassays, such as enzyme linked immunoabsorbant assay (ELISA), radioimmunoassay (RIA), Immunoradiometric assay (IRMA), Western blotting, immunocytochemistry or immunohistochemistry, each of which are described in more detail below. In some embodiments, immunoassays such as ELISA or RIA can be used for determining presence of the fusion protein in the sample. Antibody arrays or protein chips can also be employed, see for example U.S. Patent Application Nos: 2003/0013208A1; 2002/0155493A1; 2003/0017515 and U.S. Pat. Nos. 6,329,209; 6,365,418, which are herein incorporated by reference. Commercially available antibodies and/or immunoassays (such as ELISA) for detecting YWHAE or FAM22 proteins, e.g., from Cell BioLabs, Abcam, Novus Biologicals, and Thermo Scientific Pierce Antibodies, can be used in the assays and/or methods described herein.

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-enzyme) is linked to a solid phase (i.e. a microtiter plate) and exposed to a biological sample containing antigen (e.g. enzyme). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e. enzyme). The antigen-antibody mixture is then contacted with a solid phase (e.g. a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a test sample is tested for specific proteins by exposing the test sample to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, for example, by light microscopy of a sample stained with a stain that is detected in the visible spectrum, using any of a variety of such staining methods and reagents known to those skilled in the art.

Alternatively, "Radioimmunoassays" can be employed. A radioimmunoassay is a technique for detecting and measuring the concentration of an antigen using a labeled (e.g. radioactively or fluorescently labeled) form of the antigen. Examples of radioactive labels for antigens include $^3$H, $^{14}$C, and $^{125}$I. The concentration of antigen enzyme in a test sample or a biological sample can be measured by having the antigen in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

In some embodiments, Western blotting (Towbin et at., Proc. Nat. Acad. Sci. 76:4350 (1979)) can be used to presence of the fusion protein in the sample, wherein a suitably treated sample is run on an SDS-PAGE gel before being transferred to a solid support, such as a nitrocellulose filter. Detectably labeled anti-enzyme antibodies can then be used to assess enzyme levels, where the intensity of the signal from the detectable label corresponds to the amount of enzyme present. Levels can be quantified, for example by densitometry.

In addition to immunoassays, the presence of the fusion protein in the sample can also be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, content of all of which is incorporated herein by reference in their entirety. Mass spectrometry methods are well known in the art and have been used to quantify and/or identify molecules (see, e.g., Li et al. (2000) Tibtech 18:151-160; Rowley et al. (2000) Methods 20: 383-397; and Kuster and Mann (1998) Curr. Opin. Structural Biol. 8: 393-400).

In some embodiments, a gas phase ion spectrophotometer can be used. In other embodiments, laser-desorption/ionization mass spectrometry can be used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 and No. 5,045,694, content of both of which is incorporated herein by reference in their entirety.

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361, content of both of which is incorporated herein by reference in their entirety. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4$^{th}$ ed. Vol. 15 (John Wiley & Sons, New York 1995), pp. 1071-1094. Software programs such as the Biomarker Wizard program (Ciphergen Biosystems, Inc., Fremont, Calif.) can be used to aid in analyzing mass spectra, e.g., comparing the signal strength of peak values from spectra of a test subject sample and a control sample (e.g., a normal healthy person). The mass spectrometers and their techniques are well known to those of skill in the art.

In some embodiments, the assays, methods, and systems described herein comprise contacting the biological sample with a reagent that binds with the fusion protein or the nucleic acid. In some embodiments, the contacting is under conditions that permit binding of the reagent to the fusion protein or the nucleic acid encoding the same.

In some embodiments, the reagent can be an antibody, or a fragment thereof which retains binding to the fusion protein.

In some embodiments, the method further comprises contacting the sample with a second reagent. The second reagent can be chosen so that it binds with the fusion protein, the nucleic acid encoding the same, the first reagent, a complex between the fusion protein and the first reagent, or a complex between the nucleic acid and the first reagent.

Without wishing to be bound by a theory, use of two or more different reagents can be useful in "sandwich-type" detection assays. For example, the first regent can be used to capture an analyte (e.g., the fusion protein or the nucleic acid) and the second reagent used for detecting the first reagent—analyte complex.

Without limitation a reagent can be selected from the group consisting of nucleic acids, antibodies, antibody fragments, small molecules, polypeptides, peptides, peptidomimetics, lipids, saccharides, and the like. In some embodiments, the reagent is an antibody, an antibody fragment, or a nucleic acid. The reagent can be adapted to bind to the fusion protein, the nucleic acid encoding the same, or another reagent. The reagent can also be adapted for detecting the presence of the fusion protein or the nucleic acid encoding the same in the sample.

In some embodiments, the reagent is a synthetic molecule or an isolated molecule.

In some embodiments, the reagent is an antibody that binds to an epitope defined by amino acids 1-70 of the full length YWHAE. In some embodiments, the reagent is an antibody, or fragment thereof, that binds to an epitope defined by amino acids 1-70 of SEQ ID NO: 3 or SEQ ID NO: 4

In some embodiments, the reagent is an antibody that binds to an epitope defined by amino acids 1-70 of the full length YWHAE. In some embodiments, the reagent is an antibody, or fragment thereof, that binds to an epitope defined by amino acids 1-70 of SEQ ID NO: 3 or SEQ ID NO: 4.

In some embodiments, the antibody is a rabbit antibody. In some embodiments, the antibody is antibody HPA008445 (Sigma).

In some embodiments, the reagent is an antibody that binds a portion of SEQ ID No: 3 or SEQ ID NO: 4 but does not bind the full length YWHAE and the FAM22 proteins. Methods for raising antibodies against a protein are well known in the art and can be used to obtain antibodies that are specific for the fusion-protein and do not bind to the full length YWHAE and the FAM22 proteins. For example, antibodies can be raised against the fusion protein and assayed for binding to the full length YWHAE or the FAM22 proteins. Antibodies that do not bind to the full length YWHAE and the FAM22 proteins can be selected for the assays, methods, systems, kits, and compositions described herein.

In some embodiments, the detection method comprises: (i) contacting the biological sample with: (a) a first reagent, e.g., antibody or fragment thereof that binds with a full length YWHAE or FAM22 protein and the fusion protein; and (b) a second reagent, e.g., antibody or fragment that binds with the full length YWHAE or FAM22 protein but does not bind the fusion protein; and (ii) detecting of binding of the first reagent and the second reagent in the sample, wherein binding of the first reagent but not the second reagent indicating that a YWHAE-FAM22 fusion protein is present in the sample. In some embodiments, the first antibody can be antibody HPA008445 (Sigma) and the second antibody can be BML-SA475R (Enzo Life Sciences).

In some embodiments, the reagent can be adapted to produce a signal when bound to the fusion protein or the nucleic acid.

In some embodiments, the reagent comprises a label. As used herein, the term "label" refers to any molecule that has a detectable property or is capable of producing a detectable signal. The term "detectable property" means a physical or chemical property of a molecule that is capable of independent detection or monitoring by an analytical technique after being conjugated with an affinity molecule, i.e., the property is capable of being detected in the presence of a sample under analysis. The property can be light emission after excitation, quenching of a known emission sites, electron spin, radio activity (electron emission, positron emission, alpha particle emission, etc.), nuclear spin, color, absorbance, near IR absorbance, UV absorbance, far UV absorbance, etc. As such, a label is any composition detectable by spectroscopic, photochemical, biochemical, immunochemical, electrical, optical or chemical means needed for the methods and devices described herein.

Suitable label moieties include fluorescent molecules, luminescent molecules and nanoparticles, radioisotopes, chromophores, nucleotide chromophores, enzymes, substrates, chemiluminescent moieties, bioluminescent moieties, magnetic microbeads, magnetic nanoparticles, plasmonic nanoparticles, upconverting nanoparticles, bioluminescent moieties, nanoparticles comprising fluorescent molecules, nanoparticles comprising fluorophores, and the like. Means of detecting such labels are well known to those of skill in the art. For example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label. As such, a label moiety is any moiety detectable by spectroscopic, photochemical, biochemical, immunochemical, electrical, optical or chemical means. Any method known in the art for detecting the particular label moiety can be used for detection.

The term "analytical technique" means an analytical chemical or physical approach or instrument for detecting and/or monitoring the property. Such instruments can be based on spectroscopic analytical methods such as UV and visible light spectrometry, far IR, IR and near IR spectrometry, X-ray spectrometry, electron spin resonance spectrometry, nuclear magnetic resonance (NMR) spectrometry, etc.

In some embodiments, the label moiety is a luminescent nanoparticle.

In some embodiments, the label moiety can be a magnetic nanoparticle, a plasmonic nanoparticle, or an upconverting nanoparticle. As used herein, the term "plasmonic nanoparticle" refers to a nanoparticle that has very strong absorption (and scattering) spectrum that is tunable by changing the shape, the composition or the medium around their surfaces. It will be appreciated that the term includes all plasmonic nanoparticles of various shapes and surface surrounding which gives them surface plasmon absorption and scattering spectrum in the visible-near infra-red region of the spectrum. As used herein, an "upconverting nanoparticle" means a nanoparticle which is a combination of an absorber which is excited by infrared (IR) light and an emitter ion in a crystal lattice, which converts IR light into visible radiation.

In some embodiments, the label moiety is a fluorophore or fluorescent molecule or dye. A wide variety of fluorescent molecules are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAGTm CBQCA; ATTO-TAGTm FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP-Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); DIDS; Dihydrorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodaminelsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent molecules are available and can be used.

Other exemplary label moieties include radiolabels (e.g., $^{3}H$, $^{125}I$, $^{35}S$, $^{14}C$, or $^{32}P$), enzymes (e.g., galactosidases, glucorinidases, phosphatases (e g, alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such label moieties include U.S. Pat. Nos. 3,817,837, 3,850,752, 3,939,350, 3,996,345, 4,277,437, 4,275,149, and 4,366,241, content of each of which is incorporated herein by reference in its entirety.

In some embodiments, the label is a fluorescent, luminescent, or radioactive label.

In some embodiments, the reagent can be immobilized to support. For example, the reagent can be covalently or non-covalently linked to a solid support or the reagent can be immobilized within a matrix material. Methods for immobilizing a reagent to solid support are well known in the art and available to one of skill in the art.

After a subject is identified as needing anti-cancer treatment, the subject can be treated with an anti-cancer treatment. Thus, in another aspect provided herein is method of treating cancer in a subject in need thereof, the method comprising administering an anti-cancer therapy or treatment to the subject, wherein the subject expresses a YWHAE-FAM22 fusion protein or a nucleic acid encoding the same. In some embodiments, the method comprising: assaying a biological sample from a subject for presence of the YWHAE-FAM22 fusion protein or a nucleic acid encoding the same and administering an anti-cancer therapy or treatment to the subject if the YWHAE-FAM22 fusion protein or a nucleic acid encoding the same is detected in the sample.

As used herein, an anti-cancer treatment aims to reduce, prevent or eliminate cancer cells or the spread of cancer cells or the symptoms of cancer in the local, regional or systemic circulation. Anti-cancer treatment also means the direct treatment of tumors, for example by reducing or stabilizing their number or their size (curative effect), but also by preventing the in situ progression of tumor cells or their diffusion, or the establishment of tumors; this also includes the treatment of deleterious effects linked to the presence of such tumors, in particular the attenuation of symptoms observed in a patient or an improvement in quality of life. By "reduced" in the context of cancer is meant reduction of at least 10% in the growth rate of a tumor or the size of a tumor or cancer cell burden. Exemplary anti-cancer therapies include, but are not limited to, radiation, drug, surgery to remove tumors, and the like. Many anti-cancer therapies are known to one of skill in the art and can be used with the treatment method described herein.

In some embodiments, the anti-cancer therapy comprises administering an effective amount of an anti-cancer agent to the subject.

As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

In yet another aspect provided herein is an assay for selecting a treatment regime for a subject with cancer. The assay comprising: detecting the presence of YWHAE-FAM22 fusion protein or a nucleic acid encoding the same in a biological sample taken from the subject; and if at least one of the fusion protein or the nucleic acid is detected, then selecting, and optionally administering, a treatment regimen comprising an anti-cancer therapy to the subject.

Also provided herein is an isolated sample from a subject, wherein the sample comprises a YWHAE-FAM22 fusion protein or a nucleic acid encoding the same. In some embodiments, the sample further comprises a first reagent that can bind with the fusion protein or the nucleic acid.

The invention also provides a composition comprising: (i) a YWHAE-FAM22 fusion protein or a nucleic acid encoding the YWHAE-FAM22 fusion protein, wherein the YWHAE-FAM22 fusion protein or the nucleic acid is at least partially isolated from a biological sample obtained from a subject; and (ii) a reagent that binds with the fusion protein or the nucleic acid. In some embodiments, the YWHAE-FAM22 fusion protein or the nucleic acid is in a biological sample obtained from a subject.

Reagents that can bind with the fusion protein or the nucleic acids are described in detail herein. In some embodiments, the reagent is adapted to produce a signal so as to detect presence of the fusion protein or the nucleic acid in the sample.

In another aspect provided herein is an isolated fusion protein, comprising a portion of a YWHAE protein and a portion of a FAM-22 protein. In some embodiments, the fusion protein consists of amino acid sequence of SEQ ID NO: 3 or SEQ ID NO: 4.

Peptide modifications are well known in the art. Thus, a fusion protein described herein can comprise one or more peptide modifications known in the art. Exemplary peptide modifications for modifying the fusion protein described herein include, but are not limited to, D amino acids, α amino acids, β amino acids, non-amide or modified amide linkages, chemically modified amino acids, naturally occurring non-proteogenic amino acids, rare amino acids, chemically synthesized compounds that have properties known in the art to be characteristic of an amino acid, and the like.

An isolated nucleic acid encoding the fusion protein is also provided herein. In some embodiments, the nucleic acid comprises a 5'-hydroxyl group and/or a 3'-hydroxyl group. In some embodiments, the nucleic acid encoding the fusion protein consists of the nucleotide sequence of SEQ ID NO: 1 or SEQ ID NO: 2.

Modified nucleic acids are well known in the art. Thus, a nucleic acid described herein can comprise one or more nucleic acid modifications known in the art. For example, In the nucleic acid can comprise one or more nucleic acid modifications selected from the group consisting of internucleotide linkage modifications (intersugar linkage modifications), sugar modifications, nucleobase modifications, backbone modifications/replacements, and any combinations thereof. Exemplary internucleotide linkage modifications include, but are not limited to, phosphorothioate, phosphorodithioate, phosphotriester (e.g. alkyl phosphotriester), aminoalkylphosphotriester, alkyl-phosphonate (e.g., methyl-phosphonate), selenophosphate, phosphoramidate (e.g., N-alkylphosphoramidate), boranophosphonate, and the like. Exemplary sugar modifications include, but are not limited to, 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH$_2$CH$_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), arabinose sugar, and the like. Exemplary nucleobase modifications include, but are not limited to, inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; 3-deazaadenin; universal base; and any combinations thereof. Exemplary backbone modifications include, but are not limited to, morpholino, cyclobutyl, pyrrolidine, peptide nucleic acid (PNA), aminoethylglycyl PNA (aegPNA), backnone-extended pyrrolidine PNA (bepPNA), and the like.

In another aspect provided herein are systems (and computer readable media for causing computer systems) for use in the assays and methods described herein. For example for use in an assay or method for identifying a subject suitable for cancer treatment based on presence of the fusion protein or the nucleic acid encoding the same in a biological sample taken from the subject.

Generally the system comprises: (i) a determination module configured to receive at least one test sample (e.g., biological sample) and perform at least one analysis on the at least one test sample to determine presence of the fusion protein or a nucleic acid encoding the same; (ii) a storage device configured to store output data from the determination module; (iii) a computing module, e.g., a non-human machine, comprising specifically-programmed instructions to determine from the output data the presence of the fusion protein or the nucleic acid encoding the same; and (iv) a display module for displaying a content based in part on the data output from the computing module, wherein the content comprises a signal indicative of the presence of the fusion protein or the nucleic acid.

In some embodiments, the system comprises a biological sample taken from a subject and a reagent that binds with the YWHAE-FAM22 fusion protein or a nucleic acid encoding the same.

In some embodiments, the determination module can be configured to perform DNA sequencing to determine the presence of the nucleic acid encoding the fusion protein.

In some embodiments, the determination module can be configured to capture the fusion protein or the nucleic acid encoding the same.

In some embodiments, the determination module can further comprise a comparison module adapted to compare the data output from the determination module with reference data stored on the storage device. In some embodiments, the reference data can include, but not limited to, at least a part of the amino acid sequence for the fusion protein, at least a part of the nucleic acid sequence for the nucleic acid encoding the fusion protein, length of the fusion protein or the nucleic acid, molecular weight of the fusion protein or the nucleic acid, and any combinations thereof.

In some embodiments, the display module can also comprise instructions for displaying a content based in part on the data output from the comparison module. In some embodiments, the content displayed on the display module can further comprise a signal indicative of the subject recommended to receive a treatment regimen for ESS.

In some embodiments, the storage device of the computer system can be further configured to store information of at least one subject to be tested. Examples of the information can include, but is not limited to, medical history, family history, physical parameter, gender, and the like.

A tangible and non-transitory (e.g., not transitory forms of signal transmission) computer readable medium having computer readable instructions recorded thereon to define software modules for implementing a method on a computer is also provided herein. In one embodiment, the computer readable storage medium comprises: (i) instructions for comparing the data stored on a storage device with reference data to provide a comparison result, wherein the comparison identifies the presence or absence of the fusion protein or the nucleic acid encoding the same; and (ii) instructions for displaying a content based in part on the data output from the determination module, wherein the content comprises a signal indicative of the presence of the fusion protein or the nucleic acid, and optionally the absence of the fusion protein or the nucleic acid. In some embodiments, the content can comprise a signal indicative of the subject needing treatment for ESS.

In some embodiments, the instructions can be specifically programmed to perform a comparison to identify the presence of a nucleic acid comprising a nucleotide sequence homologous to the nucleic acid sequence of the nucleic acid encoding the fusion protein.

In some embodiments, the instructions can be specifically programmed to perform an analysis of binding of a reagent to the fusion protein or the nucleic acid encoding the same.

In some embodiments, the computer readable medium can further comprise instructions to identify the presence or absence of the fusion protein or the nucleic acid encoding the same.

The computer readable media can be any available tangible media that can be accessed by a computer. Computer readable media includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

In some embodiments, the computer readable storage media 700 can include the "cloud" system, in which a user can store data on a remote server, and later access the data or perform further analysis of the data from the remote server.

Figure 9:
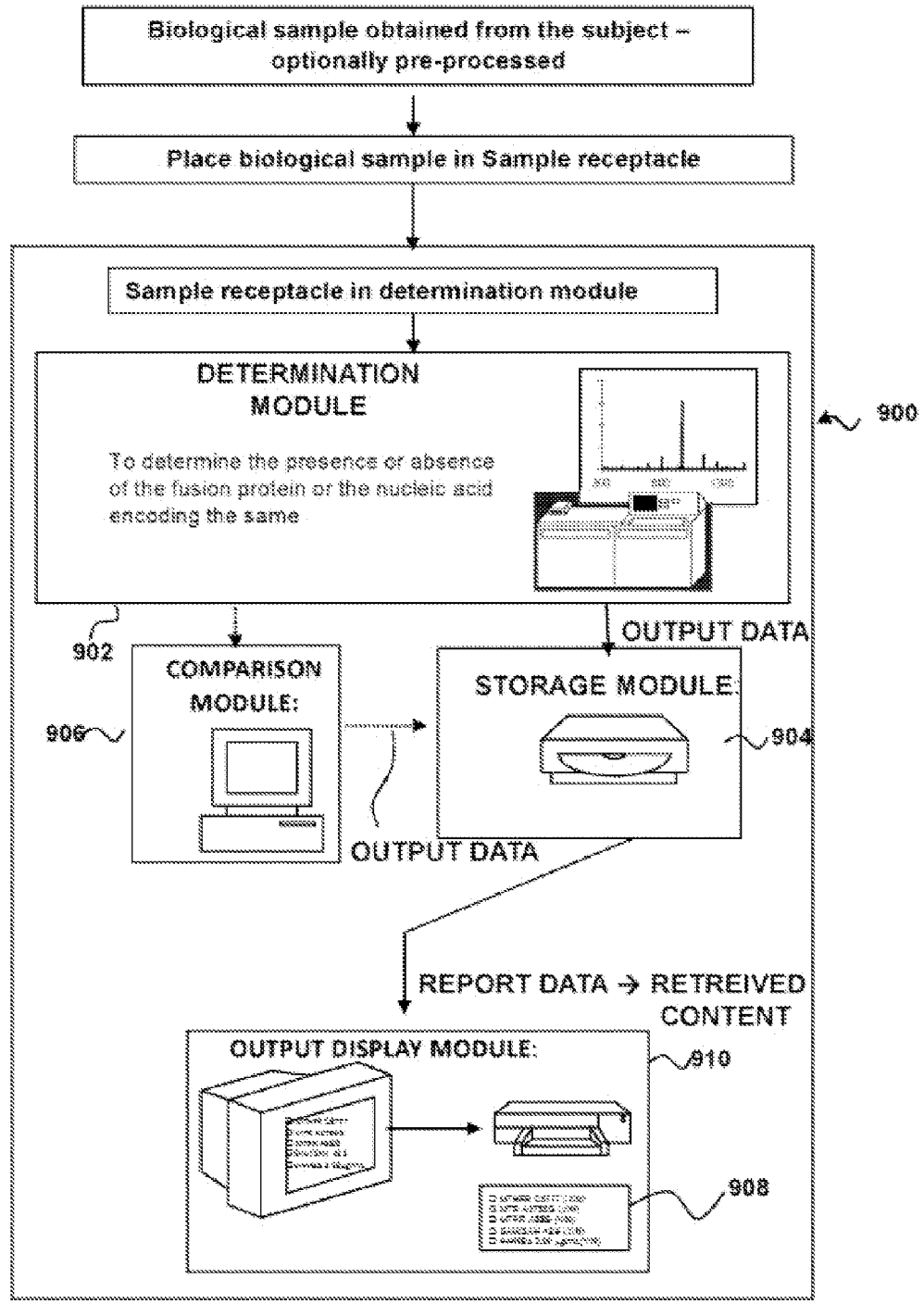
FIG. 9 is a block diagram showing an exemplary system for use in the methods described here, e.g., for selecting subject for treatment for ESS.
Figure 10:
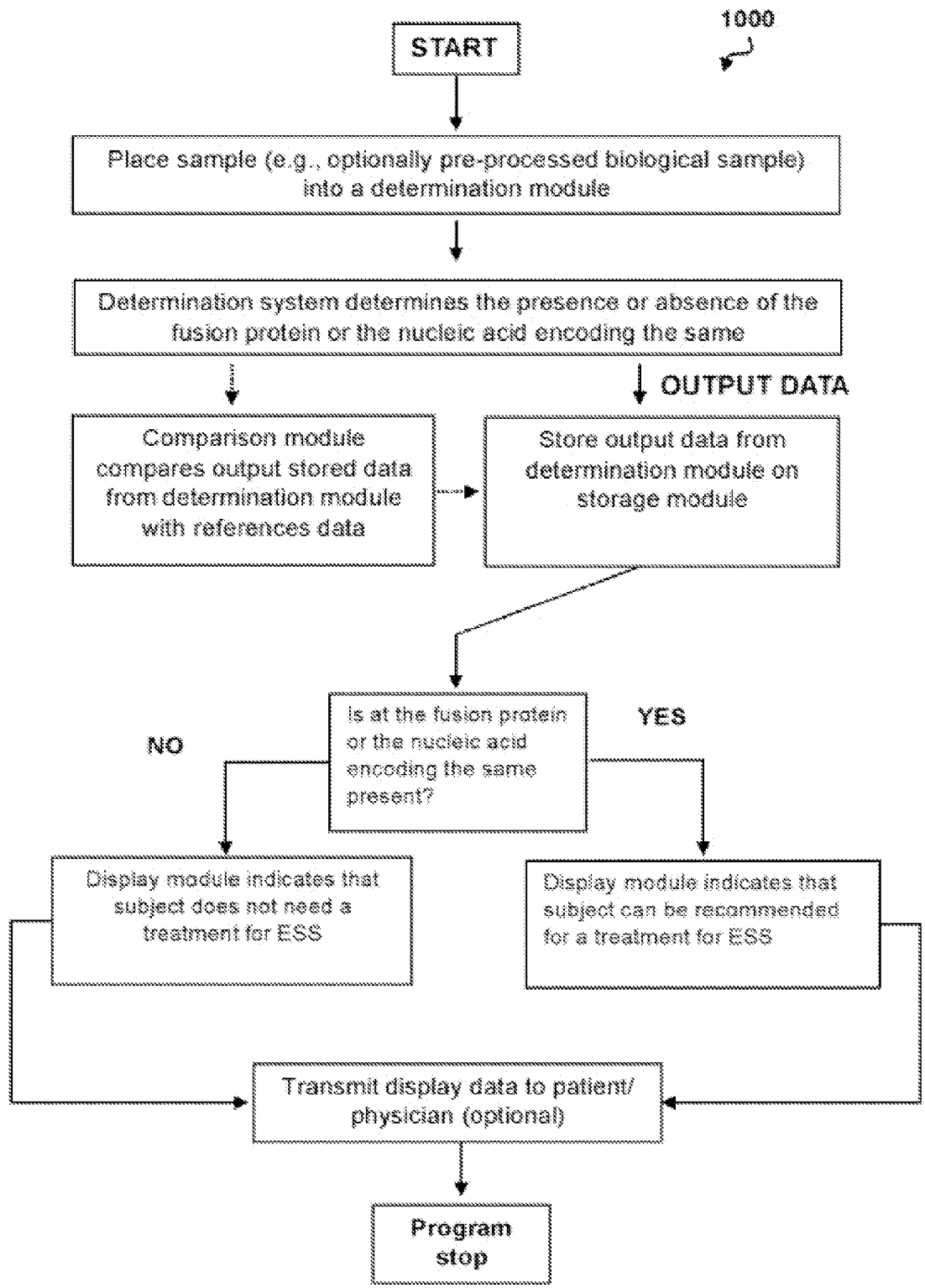
FIG. 10 is an exemplary set of instructions on a computer readable storage medium for use with the systems described herein.

An embodiment of the computer system can be illustrated with reference to FIGS. 9 and 10. Computer-readable data embodied on one or more computer-readable media, or computer readable medium 1000, can define instructions, for example, as part of one or more programs, that, as a result of being executed by a computer, instruct the computer to perform one or more of the functions described herein (e.g., in relation to system 900, or computer readable medium 1000), and/or various embodiments, variations and combinations thereof. Such instructions can be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied can reside on one or more of the components of either of system 900, or computer readable medium 1000 described herein, may be distributed across one or more of such components, and may be in transition there between.

The computer-readable media can be transportable such that the instructions stored thereon can be loaded onto any computer resource to implement the assays and/or methods described herein. In addition, it should be appreciated that the instructions stored on the computer readable media, or computer-readable medium 1000, described above, are not limited to instructions embodied as part of an application program running on a host computer. Rather, the instructions may be embodied as any type of computer code (e.g., software or microcode) that can be employed to program a computer to implement the assays and/or methods described herein. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the system described herein can include a determination module, a storage device, and a display module. In some embodiments, the system can further include a comparison module. The functional modules can be executed on one, or multiple, computers, or by using one, or multiple, computer networks. The determination module 902 has computer executable instructions to provide sequence information in computer readable form. As used herein, "sequence information" refers to any nucleotide and/or amino acid sequence, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample (e.g., amino acid sequence expression levels, or nucleotide (RNA or DNA) expression levels), and the like. The term "sequence information" is intended to include the presence or absence of post-translational modifications (e.g. phosphorylation, glycosylation, summylation, farnesylation, and the like).

As an example, determination modules 902 for determining sequence information may include known systems for automated sequence analysis including but not limited to Hitachi FMBIO® and Hitachi FMBIO® II Fluorescent Scanners (available from Hitachi Genetic Systems, Alameda, Calif.); Spectrumedix® SCE 9610 Fully Automated 96-Capillary Electrophoresis Genetic Analysis Systems (available from SpectruMedix LLC, State College, Pa.); ABI PRISM® 377 DNA Sequencer, ABI® 373 DNA Sequencer, ABI PRISM® 310 Genetic Analyzer, ABI PRISM® 3100 Genetic Analyzer, and ABI PRISM® 3700 DNA Analyzer (available from Applied Biosystems, Foster City, Calif.); Molecular Dynamics FluorImager™ 575, SI Fluorescent Scanners, and Molecular Dynamics FluorImager™ 595 Fluorescent Scanners (available from Amersham Biosciences UK Limited, Little Chalfont, Buckinghamshire, England); GenomyxSC™ DNA Sequencing System (available from Genomyx Corporation (Foster City, Calif.); and Pharmacia ALF™ DNA Sequencer and Pharmacia ALFexpress™ (available from Amersham Biosciences UK Limited, Little Chalfont, Buckinghamshire, England).

Alternative methods for determining sequence information, i.e. determination modules 902, include systems for protein and DNA analysis. For example, mass spectrometry systems including Matrix Assisted Laser Desorption Ionization—Time of Flight (MALDI-TOF) systems and SELDI-TOF-MS ProteinChip array profiling systems; systems for analyzing gene expression data (see, for example, published U.S. Patent Application, Pub. No. U.S. 2003/0194711); systems for array based expression analysis: e.g., HT array systems and cartridge array systems such as GeneChip® AutoLoader, Complete GeneChip® Instrument System, GeneChip® Fluidics Station 450, GeneChip® Hybridization Oven 645, GeneChip® QC Toolbox Software Kit, GeneChip® Scanner 3000 7G plus Targeted Genotyping System, GeneChip® Scanner 3000 7G Whole-Genome Association System, GeneTitan™ Instrument, and GeneChip® Array Station (each available from Affymetrix, Santa Clara, Calif.); automated ELISA systems (e.g., DSX® or DS2® (available from Dynax, Chantilly, Va.) or the Triturus® (available from Grifols USA, Los Angeles, Calif.), The Mago® Plus (available from Diamedix Corporation, Miami, Fla.); Densitometers (e.g. X-Rite-508-Spectro Densitometer® (available from RP Imaging™, Tucson, Ariz.), The HYRYS™ 2 HIT densitometer (available from Sebia Electrophoresis, Norcross, Ga.); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, (available from Becton Dickinson, Franklin Lakes, N.J.); and radio isotope analyzers (e.g. scintillation counters).

The sequence information and/or expression level information determined in the determination module can be read by the storage device 904. As used herein the "storage device" 904 is intended to include any suitable computing or processing apparatus or other device configured or adapted for storing data or information. Examples of electronic apparatus suitable for use with the system described herein can include stand-alone computing apparatus, data telecommunications networks, including local area networks (LAN), wide area networks (WAN), Internet, Intranet, and Extranet, and local and distributed computer processing systems. Storage devices 604 also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device 604 is adapted or configured for having recorded thereon sequence information or expression level information. Such information may be provided in digital form that can be transmitted and read electronically, e.g., via the Internet, on diskette, via USB (universal serial bus) or via any other suitable mode of communication, e.g., the "cloud".

As used herein, "expression level information" refers to any nucleotide and/or amino acid expression level information, including but not limited to full-length nucleotide and/or amino acid sequences, partial nucleotide and/or amino acid sequences, or mutated sequences. Moreover, information "related to" the expression level information includes detection of the presence or absence of a sequence (e.g., presence or absence of an amino acid sequence, nucleotide sequence, or post translational modification), determination of the concentration of a sequence in the sample (e.g., amino acid sequence levels, or nucleotide (RNA or DNA) expression levels, or level of post translational modification), and the like. In some embodiments, the expression level information also includes arithmetic manipulation of expression levels.

As used herein, "stored" refers to a process for encoding information on the storage device 904. Those skilled in the art can readily adopt any of the presently known methods for recording information on known media to generate manufactures comprising the sequence information or expression level information.

A variety of software programs and formats can be used to store the sequence information or expression level information on the storage device. Any number of data processor structuring formats (e.g., text file or database) can be employed to obtain or create a medium having recorded thereon the sequence information or expression level information.

By providing sequence information and/or expression level information in computer-readable form, one can use the sequence information and/or expression level information in readable form in the comparison module 906 to compare a specific sequence or expression profile with the reference data within the storage device 904. For example, search programs can be used to identify fragments or regions of the sequences that match a particular sequence (reference data, e.g., sequence information of major or rare alleles corresponding to the SNPs described herein) or direct comparison of the determined expression level can be compared to the reference data expression level (e.g., median expression level information obtained from a population of subjects). The comparison made in computer-readable form provides a computer readable comparison result which can be processed by a variety of means. Content 908 based on the comparison result can be retrieved from the determination module 902 or the comparison module 906 to indicate the presence or absence of the fusion protein or the nucleic acid encoding the same.

In one embodiment the reference data stored in the storage device 904 to be read by the determination module 902 or the comparison module 906 is sequence information data obtained from a control biological sample of the same type as the biological sample to be tested. Alternatively, the reference data are a database, e.g., a part of the entire genome sequence of an organism, or a protein family of sequences, or an expression level profile (RNA, protein or peptide). In one embodiment, the reference data are sequence information and/or expression level profiles that are used to facilitate determining whether a subject should be recommended for a treatment regimen for ESS.

In some embodiments, the reference data are one or more reference polynucleotide, or polypeptide sequences. In some embodiments, the reference polynucleotide sequences can be derived from nucleotide sequences selected SEQ ID NO: 1 or SEQ ID NO: 2. In some embodiments, the reference polypeptide sequences can be derived from amino acid sequences of SEQ ID NO: 3 or SEQ ID NO: 4.

In one embodiment, the reference data are electronically or digitally recorded and annotated from databases including, but not limited to GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting information can be stored in a relational data base that may be employed to determine homologies between the reference data or genes or proteins within and among genomes.

The "comparison module" 906 can use a variety of available software programs and formats for the comparison operative to compare sequence information determined in the determination module 902 to reference data. In one embodiment, the comparison module 906 is configured to use pattern recognition techniques to compare sequence information from one or more entries to one or more reference data patterns. The comparison module 906 can be configured using existing commercially-available or freely-available software for comparing patterns, and may be optimized for particular data comparisons that are conducted. The comparison module 906 provides computer readable information related to the sequence information that can include, for example, detection of the presence or absence of a sequence (e.g., detection of a mutation or deletion (protein or DNA), information regarding distinct alleles, detection of post-translational modification, or omission or repetition of sequences); determination of the concentration of a sequence in the sample (e.g., amino acid sequence/protein expression levels, or nucleotide (RNA or DNA) expression levels, or levels of post-translational modification), or determination of an expression profile.

In one embodiment, the comparison module 906 permits the prediction of protein sequences from polynucleotide sequences, permits prediction of open reading frames (ORF), or permits prediction of homologous sequence information in comparison to reference data, i.e., homologous protein domains, homologous DNA or RNA sequences, or homologous exons and/or introns.

In one embodiment, the comparison module 906 uses sequence information alignment programs such as BLAST (Basic Local Alignment Search Tool) or FAST (using the Smith-Waterman algorithm) may be employed individually or in combination. These algorithms determine the alignment between similar regions of sequences and a percent identity between sequences. For example, alignment may be calculated by matching, bases-by-base or amino acid-by amino-acid.

The comparison module 906, or any other module of the system described herein, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular embodiment, users can directly access data (via Hypertext links for example) residing on Internet databases using a HTML interface provided by Web browsers and Web servers. In another embodiment, users can directly access data residing on the "cloud" provided by the cloud computing service providers.

In one embodiment, the comparison module 906 performs comparisons with mass-spectrometry spectra, for example comparisons of peptide fragment sequence information can be carried out using spectra processed in MATLAB with script called "Qcealign" (see for example WO2007/022248, herein incorporated by reference) and "Qpeaks" (Spectrum Square Associates, Ithaca, N.Y.), or Ciphergen Peaks 2.1™ software. The processed spectra can then be aligned using alignment algorithms that align sample data to the control data using minimum entropy algorithm by taking baseline corrected data (see for example WIPO Publication WO2007/022248, herein incorporated by reference). The comparison result can be further processed by calculating ratios. Protein expression profiles can be discerned.

In one embodiment, computational algorithms are used in the comparison module 906 such as expectation-maximization (EM), subtraction and PHASE are used in methods for statistical estimation of haplotypes (see, e.g., Clark, A. G. Mol Biol Evol 7:111-22 (1990); Stephens, M., Smith, N. J. & Donnelly, P. Am J Hum Genet 68:978-89 (2001); Templeton, A. R., Sing, C. F., Kessling, A. & Humphries, Genetics 120:1145-54 (1988)).

Various algorithms are available which are useful for comparing data and identifying the predictive gene signatures. For example, algorithms such as those identified in Xu et al., Physiol. Genomics 11:11-20 (2002). There are numerous software available for detection of SNPs and polymorphisms that can be used in the comparison module, including, but not limited to: HaploSNPer, a web-based program for detecting SNPs and alleles in user-specified input sequences from both diploid and polyploid species (available on the world-wide web at bioinformatics.nl/tools/haplosnper/; see also Tang et al., BMC Genetics 9:23 (2008)); Polybayes, a tool for SNP discovery in redundant DNA sequences (March, G T., et al., Nature Genetics 23(4):452-6 (1999); SSAHA-SNP, a polymorphism detection tool that uses the SSAHA alignment algorithm (available from Wellcome Trust Sanger Institute, Cambridge, United Kingdom, see also Ning Z., et al., Genome Research 11(10):1725-9 (2001)); Polyphred, A SNP discovery package built on phred, phrap, and consed tools (available on the world-wide web, see Nickerson, D A et al., Nucleic Acids Research 25(14):2745-51 (1997)); NovoSNP, a graphical Java-based program (PC/Mac/Linux) to identify SNPs and indels (available on the world-wide web, see Weckx, S. et al., Genome Research 15(3):436-442 (2005)); SNPdetector™, for automated identification of SNPs and mutations in fluorescence-based resequencing reads (available from Affymetrix, Santa Clara, Calif.), see also Thang et al. PLoS Comput Biol (5):e53 (2005). SNPdetector runs on Unix/Linux platform and is available publicly; Affymetrix (Santa Clara, Calif.) has multiple data analysis software that can be used, for example Genotyping Console™ Software, GeneChip® Sequence Analysis Software (GSEQ), GeneChip® Targeted Genotyping Analysis Software (GTGS) and Expression Console™ Software.

In one embodiment, the comparison module 906 compares gene expression profiles. For example, detection of gene expression profiles can be determined using Affymetrix Microarray Suite software version 5.0 (MAS 5.0) (available from Affymetrix, Santa Clara, Calif.) to analyze the relative abundance of a gene or genes on the basis of the intensity of the signal from probe sets, and the MAS 5.0 data files can be transferred into a database and analyzed with Microsoft Excel and GeneSpring 6.0 software (available from Agilent Technologies, Santa Clara, Calif.). The detection algorithm of MAS 5.0 software can be used to obtain a comprehensive overview of how many transcripts are detected in given samples and allow a comparative analysis of two or more microarray data sets.

In one embodiment, the comparison module 906 compares protein expression profiles. Any available comparison software can be used, including but not limited to, the Ciphergen Express (CE) and Biomarker Patterns Software (BPS) package (available from Ciphergen Biosystems, Inc., Freemont, Calif.). Comparative analysis can be done with protein chip system software (e.g., The Proteinchip Suite (available from Bio-Rad Laboratories, Hercules, Calif.). Algorithms for identifying expression profiles can include the use of optimization algorithms such as the mean variance algorithm (e.g. JMP Genomics algorithm available from JMP Software Cary, N.C.).

In one embodiment, pattern comparison software can be used to determine whether patterns of expression or mutations are indicative of the presence or the absence of the conditions detected in a test sample of a subject.

The comparison module 906 provides computer readable comparison result that can be processed in computer readable form by predefined criteria, or criteria defined by a user, to provide content based in part on the comparison result that may be stored and output as requested by a user using a display module 910. The display module 910 enables display of a content 908 based in part on the comparison result for the user, wherein the content 908 is a signal indicative of the presence or absence of the fusion protein or the nucleic acid encoding the same. Such signal can be, for example, a display of content 908 can be on a computer monitor, a printed page, or a light or sound indicative of indicative of the presence or absence of the fusion protein or the nucleic acid encoding the same.

In various embodiments of the computer system described herein, the comparison module 906 can be integrated into the determination module 902.

The content 908 based on the comparison result can also include an expression profile of the fusion protein. In one embodiment, the content 908 based on the comparison includes a sequence of a particular gene or protein. In one embodiment, the content 908 based on the comparison result is merely a signal indicative of the presence or absence of the fusion protein or the nucleic acid encoding the same. In some embodiments, the content 908 can be a signal indicative of the subject recommended to receive a treatment regimen for treating ESS.

In one embodiment, the content 908 based on the comparison result is displayed a on a computer monitor. In one embodiment, the content 908 based on the comparison result is displayed through printable media. The display module 910 can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content 908 based on the comparison result. It should be understood that other modules of the system described herein can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to the sequence information, e.g., display of an indication of the presence or absence of mutation or deletion (DNA or protein); display of expression levels of an amino acid sequence (protein); display of nucleotide (RNA or DNA) expression levels; display of expression, SNP, or mutation profiles, or haplotypes, or display of information based thereon. In one embodiment, the sequence information of the reference sample data is also displayed.

In any embodiments, the comparison module can be executed by computer implemented software as discussed earlier. In such embodiments, a result from the comparison module can be displayed on an electronic display. The result can be displayed by graphs, numbers, characters or words. In additional embodiments, the results from the comparison module can be transmitted from one location to at least one other location. For example, the comparison results can be transmitted via any electronic media, e.g., internet, fax, phone, a "cloud" system, and any combinations thereof. Using the "cloud" system, users can store and access personal files and data or perform further analysis on a remote server rather than physically carrying around a storage medium such as a DVD or thumb drive.

The system 900 and computer readable medium 1000 are merely illustrative embodiments for performing assays for identifying a subject for treatment for ESS, based on presence of the fusion protein or the nucleic acid encoding the same in sample taken from the subject, and is not intended to limit the scope of the inventions described herein. Variations of system 900 and computer readable medium 1000 are possible and are intended to fall within the scope of the inventions described herein.

The modules of the machine, or used in the computer readable medium, can assume numerous configurations. For example, function can be provided on a single machine or distributed over multiple machines.

Kits

In yet another aspect provided herein are kits for use in the assay, methods, systems and compositions described herein. Accordingly, provided herein include kits for identifying a subject for endometrial stromal sarcoma or assessing the endometrial stromal sarcoma status in a subject. The kits can include at least one reagent adapted for detecting for the presence or absence of the fusion protein or the nucleic acid encoding the same. The kits can also include instructions for determining that the subject is recommended for a treatment regimen for treatment of ESS.

In some embodiments, the kit can comprise a solid substrate support affixed with at least one reagent that can bind (e.g., specifically bind) to the fusion protein or the nucleic acid encoding the same. Exemplary solid substrate support can include, but not limited to, a microtiter plate for ELISA, a dipstick, a magnetic bead, or any combinations thereof. Different solid substrate supports can be selected based on various types of assays, e.g., but not limited to, Western blot, enzyme linked absorbance assay, mass spectrometry, immunoassay, flow cytometry, immunohistochemical analysis, and any combinations thereof.

In some embodiments, the kit comprises at least one reagent adapted for detecting presence of a YWHAE-FAM22 fusion protein or a nucleic acid encoding the same.

In some embodiments, the kit comprises at least one reagent that specifically binds the fusion protein or the nucleic acid.

In some embodiments, the kit comprises a first reagent and a second reagent, wherein each can bind to the fusion protein or the nucleic acid. In some embodiments, the first reagent binds the YWHAE portion of the fusion protein or the nucleic acid encoding the same and the second reagent binds the FAM-22 portion of the fusion protein or the nucleic acid encoding the same. By way of an example only, the first reagent can be an antibody that binds with a YWHAE protein and the second reagent can be an antibody that binds with a FAM-22 protein. In another example, the first and second reagents can be nucleic acid primers, wherein the first reagent (i.e., primer) is complementary or homologous to a portion of the nucleic acid encoding the YWHAE portion of the fusion protein and a second reagent (i.e., primer) is complementary or homologous to a portion of the nucleic acid encoding the FAM-22 portion of the fusion protein In some embodiments, the kit can comprise an oligonucleotide array affixed with a plurality of oligonucleotide probes that interrogate a sample for the presence of a nucleic acid encoding the fusion protein, and an optional container containing a detectable label (e.g., comprising a fluorescent molecule) to be conjugated to a nucleotide molecule derived from the sample.

Examples of reagents additional reagents that can be included the kit can include, but are not limited to, buffers, reagents for detection, and the like.

In some embodiments, the kit comprises a fusion protein or a nucleic acid encoding the same.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Other than in the operating examples, or where otherwise indicated, all numbers expressing quantities of ingredients or reaction conditions used herein should be understood as modified in all instances by the term "about." The term "about" when used to described the present invention, in connection with percentages means±1%, ±1.5%, ±2%, ±2.5%, ±3%, ±3.5%, ±4%, ±4.5%, or ±5%. The term "about" when used in connection with percentages may mean±1%, ±1.5%, ±2%, ±2.5%, ±3%, ±3.5%, ±4%, ±4.5%, or ±5% of the value being referred to.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G" a thymine "T" or a cytosine "C") or RNA (e.g. an A, a G. an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

The term "nucleic acid sequence" refers to a single or double-stranded polymer of deoxyribonucleotide or ribonucleotide bases read from the 5' to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length.

The term "oligonucleotide," as used herein refers to primers and probes described herein, and is defined as a nucleic acid molecule comprised of at least two or more ribo- or deoxyribonucleotides. The exact size of the oligonucleotide will depend on various factors and on the particular application and use of the oligonucleotide. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe can be either single-stranded or double-stranded. The exact length of the probe will depend upon many factors, including temperature, source of probe and the method used. For example, for diagnostic applications, depending on the complexity of the target sequence, an oligonucleotide probe typically contains 15-25 or more nucleotides, although it may contain fewer nucleotides. The probes as disclosed herein are selected to be substantially complementary to different strands of a particular target nucleic acid sequence. This means that the probes must be sufficiently complementary so as to be able to "specifically hybridize" or anneal with their respective target strands. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarily with the sequence of the target nucleic acid to anneal therewith specifically.

In the context of some embodiments of various aspects described herein, the term "probe" refers to a molecule which can detectably distinguish between target molecules differing in structure (e.g. nucleic acid or protein sequence). Detection can be accomplished in a variety of different ways depending on the type of probe used and the type of target molecule. Thus, for example, detection may be based on discrimination on detection of specific binding. Examples of such specific binding include antibody binding and nucleic acid, antibody binding to protein, nucleic acid binding to nucleic acid, or aptamer binding to protein or nucleic acid. Thus, for example, probes can include enzyme substrates, antibodies and antibody fragments, and preferably nucleic acid hybridization probes.

The term "specifically hybridize" refers to the association between two single-stranded nucleic acid molecules of sufficient complementary sequence to permit such hybridization under pre-determined conditions generally used in the art (sometimes the sequences are referred to as "substantially complementary"). In particular, the term specifically hybridize also refers to hybridization of an oligonucleotide with a substantially complementary sequence as compared to non-complementary sequence.

The term "specifically" as used herein with reference to a probe which is used to specifically detect a sequence difference, refers to a probe that identifies a particular sequence difference based on exclusive hybridization to the sequence difference under stringent hybridization conditions and/or on exclusive amplification or replication of the sequence difference.

In its broadest sense, the term "substantially" as used herein in respect to "substantially complementary", or when used herein with respect to a nucleotide sequence in relation to a reference or target nucleotide sequence, means a nucleotide sequence having a percentage of identity between the substantially complementary nucleotide sequence and the exact complementary sequence of the reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to the reference sequence (if not specified otherwise below). Sequence comparisons can be carried out using default GAP analysis with the University of Wisconsin GCG, SEQWEB application of GAP, based on the algorithm of Needleman and Wunsch (Needleman and Wunsch (1970) J MoI. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions.

In its broadest sense, the term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to the reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J MoI. Biol. 48: 443-453; as defined above). A nucleotide sequence "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions. The term "substantially identical", when used herein with respect to a polypeptide, means a protein corresponding to a reference polypeptide, wherein the polypeptide has substantially the same structure and function as the reference protein, e.g. where only changes in amino acids sequence not affecting the polypeptide function occur. When used for a polypeptide or an amino acid sequence, the percentage of identity between the substantially similar and the reference polypeptide or amino acid sequence is at least 24%, at least 30%, at least 45%, at least 60%, at least 75%, at least 90%, at least 95%, at least 99%, using default GAP analysis parameters as described above. Homologues are amino acid sequences that are at least 24% identical, more preferably at least 35% identical, yet more preferably at least 50% identical, yet more preferably at least 65% identical to the reference polypeptide or amino acid sequence, as measured using the parameters described above, wherein the amino acid sequence encoded by the homolog has the same biological activity as the reference polypeptide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "complementary" or "complement" as used herein refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil. Similarly, it is known that a cytosine residue of a first nucleic acid strand is capable of base pairing with a residue of a second nucleic acid strand which is anti-parallel to the first strand if the residue is guanine. A first region of a nucleic acid is complementary to a second region of the same or a different nucleic acid if, when the two regions are arranged in an anti-parallel fashion, at least one nucleotide residue of the first region is capable of base pairing with a residue of the second region. Preferably, the first region comprises a first portion and the second region comprises a second portion, whereby, when the first and second portions are arranged in an anti-parallel fashion, such that at least about 50%, and preferably at least about 75%, at least about 90%, or at least about 95% or at least 100% of the nucleotide residues of the first portion are capable of base pairing with nucleotide residues in the second portion. More preferably, all nucleotide residues of the first portion are capable of base pairing with nucleotide residues in the second portion.

As used herein, the term "epitope" means that portion of protein that is recognized by a particular antibody. As such, the term "epitope" designates a specific amino acid sequence, modified amino acid sequence, or protein secondary or tertiary structure which is recognized by an antibody.

As used herein, the term "anti-cancer activity" or "anti-cancer properties" refers to the inhibition (in part or in whole) or prevention of unregulated cell growth and/or the inhibition (in part or in whole) or prevention of a cancer as defined herein. Anticancer activity includes, e.g., the ability to reduce, prevent, or repair genetic damage, modulate undesired cell proliferation, modulate misregulated cell death, or modulate mechanisms of metastasis (e.g., ability to migrate).

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In some embodiments, one or more symptoms of a disease or disorder are alleviated by at least 5%, at least 10%, at least 20%, at least 30%, at least 40%, or at least 50%.

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. A metastasis a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. As used herein, the term cancer, includes, but is not limited to the following types of cancer, breast cancer, biliary tract cancer, bladder cancer, brain cancer including Glioblastomas and medulloblastomas; cervical cancer; choriocarcinoma; colon cancer; endometrial cancer; esophageal cancer, gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma, Wilms tumor. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, Glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Other cancers will be known to the artisan.

In some embodiments, cancer is an endometrial sarcoma. Without limitations, the endometrial cancer can be any subtypes, for example, serous, mucinous, and endometrioid histological subtypes.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary nonpolyposis colon cancer syndrome (HNPCC), Barrett's esophagus, bladder dysplasia, precancerous cervical conditions, and cervical dysplasia.

As used herein, a "subject" means a human or animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female. A subject can be one who has not been previously diagnosed with cancer, e.g. endometrial stromal sarcoma.

Preferably, the subject is a mammal. The mammal can be a human, non-human primate, mouse, rat, dog, cat, horse, or cow, but are not limited to these examples. Mammals other than humans can be advantageously used as subjects that represent animal models of cancer. In addition, the methods and compositions described herein can be used to treat domesticated animals and/or pets.

A subject can be one who has been previously diagnosed with cancer. Without wishing to be bound by a theory, the assays, methods, systems, kits and compositions described herein can be used to diagnose and/or classify endometrial cancer in the subject. The assays, methods, systems, kits and compositions described herein can further comprise selecting a subject who has cancer. The method can also comprise the step of diagnosing a subject for cancer before onset of administration or treatment regime.

The phrase "therapeutically-effective amount" as used herein means that amount of a compound, material, or composition which is effective for producing some desired therapeutic effect in at least a sub-population of cells in an animal at a reasonable benefit/risk ratio applicable to any medical treatment.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma canbe measured, for example, by high performance liquid chromatography. The effects of any particular dosage can be monitored by a suitable bioassay.

The data obtained from the cell culture assays and animal studies can be used in formulating a range of dosage for use in humans. The dosage of such compounds lies preferably within a range of circulating concentrations that include the $ED_{50}$ with little or no toxicity. The dosage canvary within this range depending upon the dosage form employed and the route of administration utilized.

The dosage can be determined by a physician and adjusted, as necessary, to suit observed effects of the treatment. Generally, the anti-cancer agents are administered at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the conjugates described herein. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period oft week, 2 weeks, 3 weeks, 4 weeks, 1 month, 2 months, 3 months, 4 months, 5 months, or 6 months or more.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

An anti-cancer agent can be administered by any appropriate route known in the art including, but not limited to, oral or parenteral routes, including intravenous, intramuscular, subcutaneous, transdermal, airway (aerosol), pulmonary, nasal, rectal, vaginal, and topical (including on the skin, and body cavities, such as buccal, vaginal, rectal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and infrasternal injection and infusion. In some embodiments of the aspects described herein, the compositions are administered by intravenous infusion or injection. In some embodiments, administration is oral.

As used herein, the term "isolated" or "purified" means that the material in question has been removed from its host, and associated impurities reduced or eliminated. Essentially, it means an object species is the predominant species present (i.e., on a molar basis it is more abundant than any other individual species in the composition), and preferably a substantially purified fraction is a composition wherein the object species comprises at least about 30 percent (on a molar basis) of all other species present. Generally, a substantially pure composition will comprise more than about 80 to 90 percent of all species present in the composition. Most preferably, the object species is purified to essential homogeneity (contaminant species cannot be detected in the composition by conventional detection methods) wherein the composition consists essentially of a single macromolecular species. With reference to nucleic acid molecules, the term "isolated nucleic acid" refers to a nucleic acid molecule that is manipulated or modified by hand-of-man to remove at least one component with which it is generally found in its natural environment. Thus, the term "isolated nucleic acid" refers to a nucleic acid sequence that is separated from sequences with which it is immediately contiguous (in the 5' and 3' directions) in the naturally occurring genome of the organism from which it was derived. With reference to proteins, the term "isolated protein" refers to a protein that is manipulated or modified by hand-of-man to remove at least one component with which it is generally found in its natural environment. Generally, isolating a compound from its natural environment entails at least some manipulation of the target component such that the isolated target component can be said to have been manipulated by hand-of-man and thus in some aspect different from as it occurred in nature. In other words, an isolated compound can be considered as a compound that is does not occur in nature.

Embodiments of the various aspects described herein can also be described by any one of the following paragraphs.

1. A method of identifying a subject suitable for endometrial stromal sarcoma (ESS) treatment, the method comprising a step of detecting in a biological sample taken from the subject presenting a symptom of ESS the presence of a YWHAE-FAM22 fusion protein or a nucleic acid encoding the same, wherein detection of the fusion protein or the nucleic acid in the biological sample indicates that the individual should undergo ESS treatment.
2. The method of paragraph 1, wherein the nucleic acid comprises the nucleotide sequence of SEQ ID NO: 1 or SEQ ID NO: 2.
3. The method of any of paragraphs 1 or 2, wherein the fusion protein comprises the amino acid sequence of SEQ ID NO: 3 or SEQ ID NO: 4.
4. The method of any of paragraphs 1-3, wherein the sample is selected from the group consisting of blood, urine, plasma, tissue, cell, and any combinations thereof.
5. The method of any of paragraphs 1-4, wherein the subject is a mammal.
6. The method of any of paragraphs 1-5, wherein the subject is human.
7. The method of any of paragraphs 1-6, wherein method comprises contacting the sample with a first reagent that binds with the fusion gene or the fusion protein.
8. The method of paragraph 7, wherein the first reagent is selected from the group consisting of a nucleic acid, an antibody, a small molecule, a polypeptide, a peptide, a lipid, and any combinations thereof.
9. The method of paragraph 7 or 8, wherein the first reagent further comprises a label to produce a signal so as to detect presence of the fusion gene or the fusion protein in the sample.
10. The method of paragraph 9, wherein the label is selected from the group consisting of a radiolabel, a chromophore, a fluorophore, an enzyme, and any combinations thereof.
11. The method of any of paragraphs 7-10, wherein the first reagent is covalently or non-covalently linked to a solid support.
12. The method of paragraph 11, wherein the solid support is selected from the group consisting of a chip, a microarray, a gel, a test strip, and any combinations thereof.
13. The method of any of paragraphs 7-12, wherein the sample comprises a second reagent, wherein the second reagent binds with the first reagent, the fusion gene, or the fusion protein.
14. The method of paragraph 13, wherein the second reagent is selected from the group consisting of a nucleic acid, an antibody, a small molecule, a polypeptide, a peptide, a lipid, and any combinations thereof.
15. The method of paragraph 13 or 14, wherein the second reagent further comprises a label to produce a signal so as to detect presence of the first reagent bound to the fusion gene or the fusion protein in the isolated sample.
16. The method of paragraph 15, wherein the label is selected from the group consisting of fluorophores, enzymes, and any combinations thereof.

17. The method of any of paragraphs 13-16, wherein the second reagent is covalently or non-covalently linked to a solid support.
18. The method of paragraph 17, wherein the solid support is selected from the group consisting of a chip, a microarray, a gel, a test strip, and any combinations thereof.
19. An assay for selecting a treatment regimen for a subject with endometrial stromal sarcoma, the assay comprising subjecting a biological sample from the subject to:
    (i) at least one protein detection assay adapted to determine the presence of a YWHAE-FAM22 fusion protein; or
    (ii) at least one nucleic acid sequence detection assay adapted to determine the presence of a nucleic acid encoding the YWHAE-FAM22 fusion protein, if at least one of the fusion protein or the nucleic acid is detected, then selecting, and optionally administering, a treatment regimen comprising an effective amount of an anti-cancer agent.
20. The assay of paragraph 19, wherein the nucleic acid comprises the nucleotide sequence of SEQ ID NO: 1 or SEQ ID NO: 2.
21. The assay of paragraph 19 or 20, wherein the fusion protein comprises the amino acid sequence of SEQ ID NO: 3 or SEQ ID NO: 4.
22. A method of treating endometrial stromal sarcoma in a subject in need thereof, the method comprising:
    (i) providing a composition comprising a drug to treat endometrial stromal sarcoma; and
    (ii) administering an effective amount of the drug to the subject so as to treat endometrial stromal sarcoma, wherein the subject expresses a nucleic acid encoding a YWHAE-FAM22 fusion protein.
23. The method of paragraph 40, wherein the nucleic acid comprises the nucleotide sequence of SEQ ID NO: 1 or SEQ ID NO: 2.
24. An isolated sample obtained from a subject, wherein the sample comprises a YWHAE-FAM22 fusion protein or a nucleic acid encoding the fusion protein, and a or a fusion and a first reagent that binds with the fusion protein or the nucleic acid, and wherein the reagent is adapted to produce a signal so as to detect presence of the fusion protein or the nucleic acid in the isolated sample.
25. The isolated sample of paragraph 24, wherein the sample is selected from the group consisting of blood, urine, plasma, tissue, cell, saliva, and any combinations thereof.
26. The isolated sample of paragraph 24 or 25, wherein the subject is a mammal.
27. The isolated sample of any of paragraphs 24-26, wherein the subject is a human.
28. The isolated sample of any of paragraphs 24-27, wherein the first reagent is selected from the group consisting of a nucleic acid, an antibody, a small molecule, a polypeptide, a peptide, a lipid, an oligo- or poly-saccharide, and any combinations thereof.
29. The isolated sample of any of paragraphs 24-28, wherein the first reagent further comprises a label to produce a signal so as to detect presence of the fusion gene or the fusion protein in the isolated sample.
30. The isolated sample of paragraph 29, wherein the label is selected from the group consisting of a radiolabel, a chromophore, a fluorophore, an enzyme, and any combinations thereof.
31. The isolated sample of any of paragraphs 24-30, wherein the first reagent is covalently or non-covalently linked to a solid support.
32. The isolated sample of paragraph 31, wherein the solid support is selected from the group consisting of a chip, a microarray, a gel, a test strip, and any combinations thereof.
33. The isolated sample of any of paragraphs 24-32, wherein the sample comprises a second reagent, wherein the second reagent binds with the first reagent, the fusion protein or the nucleic acid.
34. The isolated sample of paragraph 33, wherein the second reagent further comprises a label to produce a signal so as to detect presence of the first reagent bound to the fusion protein or the nucleic acid in the isolated sample.
35. The isolated sample of paragraph 34, wherein the label is selected from the group consisting of a radiolabel, a chromophore, a fluorophore, an enzyme, and any combinations thereof.
36. The isolated sample of any of paragraphs 33-35, wherein the second reagent is covalently or non-covalently linked to a solid support.
37. The isolated sample of paragraph 36, wherein the solid support is selected from the group consisting of a chip, a microarray, a gel, a test strip, and any combinations thereof.
38. The isolated sample of any of paragraphs 24-37, wherein the nucleic acid comprises the nucleotide sequence of SEQ ID NO: 1 or SEQ ID NO: 2.
39. The isolated sample of any of paragraphs 24-38, wherein the fusion protein comprises the nucleotide sequence of SEQ ID NO: 3 or SEQ ID NO: 4.
40. A composition comprising:
    (i) a YWHAE-FAM22 fusion protein or a nucleic acid encoding the YWHAE-FAM22 fusion protein, wherein the YWHAE-FAM22 fusion protein or the nucleic acid is at least partially isolated from a biological sample obtained from a subject; and
    (ii) a reagent that binds with the fusion protein or the nucleic acid, wherein the reagent is adapted to produce a signal so as to detect presence of the fusion protein or the nucleic acid in the composition, and wherein the YWHAE-FAM22 fusion protein or the nucleic acid is in a biological sample obtained from a subject.
41. A system comprising:
    (i) a biological sample obtained from a subject; and
    (ii) a reagent that binds with a YWHAE-FAM22 fusion protein or a nucleic acid encoding the YWHAE-FAM 22 fusion protein, wherein the reagent is adapted to produce a signal so as to detect presence of the fusion protein or the nucleic acid in the biological sample obtained from the subject.
42. A computer system comprising for obtaining data from at least one test sample obtained from at least one subject, the system comprising:
    (i) at least one determination module configured to receive said at least one test sample and perform at least one analysis on said at least one test sample to determine the presence or absence of a YWHAE-FAM22 fusion protein or a nucleic acid encoding the same;
    (ii) at least one storage device configured to store data output from said determination module; and
    (iii) at least one display module for displaying a content based in part on the data output from said determination module, wherein the content comprises a signal indicative of the presence of the fusion gene or the fusion protein.
43. An isolated nucleic acid encoding a YWHAE-FAM22 fusion protein.

44. The isolated nucleic acid of paragraph 43, wherein the isolated nucleic acid comprises the nucleotide sequence of SEQ ID NO: for SEQ ID NO: 2.
45. The isolated nucleic acid of paragraph 43 or 44, wherein the YWHAE-FAM22 fusion protein comprises the amino acid sequence of SEQ ID NO: 3 or SEQ ID NO: 4.
46. An isolated fusion protein, wherein the fusion protein is encoded by a YWHAE-FAM22 fusion gene.
47. The isolated fusion protein of paragraph 46, wherein the fusion protein comprises the amino acid sequence of SEQ ID NO: 3 or SEQ ID NO: 4.
48. A kit for assessing endometrial stromal sarcoma status in a subject, the kit comprising at least one reagent adapted for detecting the presence of a YWHAE-FAM22 fusion gene or a fusion protein encoded by the fusion gene.
49. The kit of paragraph 48, wherein the at least one reagent is anchored on a solid support.
50. A method of treating endometrial stromal sarcoma in a subject in need thereof, the method comprising:
   (i) assaying a biological sample from the patient for presence of a YWHAE-FAM22 fusion protein or a nucleic acid encoding thereof; and
   (ii) if the fusion protein or the nucleic acid is detected in the sample, administering an anti-cancer therapy to the subject.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1

14-3-3 Fusion Oncogenes in High-Grade Endometrial Stromal Sarcoma

Study Samples:

The study samples include frozen and formalin-fixed paraffin-embedded tissues retrieved from tumor banks and pathology archives at Brigham and Women's Hospital, Catholic University of Leuven, Vancouver General Hospital, and Stanford University Medical Center with the approval of the respective institutional research boards. Cell lines, including ESS1, ESS-JAZFE gastrointestinal stromal tumor (GIST430), and leiomyosarcoma (LMS03), were developed at Brigham and Women's Hospital.

Cytogenetic Analysis and FISH:

Cytogenetic analysis was performed on Giemsa-banded metaphase spreads per standard protocol (21). FISH analyses were performed on 4-μm tissue sections that were prebaked for 2 h at 60° C. The sections were deparaffinized in xylene three times for 15 min each and dehydrated twice in 100% ethanol for 2 min. The slides were immersed in Tris-EDTA [100 mM Tris base and 50 mM EDTA (pH 7.0)] for 45 min at 95-99° C. and rinsed in 1×PBS for 5 min. Proteolytic digestion of the sections was performed using Digest-ALL 3 (Invitrogen) at 37° C. for 20 min, twice. The sections were then sequentially dehydrated in alcohol (70%, 85%, 95%, and 100%) for 2 min each and air-dried. The YWHAE break-apart probe was composed of two sets of overlapping BAC clones (Children's Hospital Oakland Research Institute), telomeric (RP11-143L7 and RP11-22G12, biotin-labeled) and centromeric (RP11-100F18 and RP11-60C18, digoxigenin-labeled), detected with streptavidin Alexa Fluor 594 conjugate (Invitrogen) and FITC anti-digoxigenin (Roche Diagnostics). The 10q23.2 (FAM22A region) breakpoint flanking probes were RP11-1005L9 (biotin-labeled) and RP11-210E13 (digoxigenin-labeled), and the 10q22.3 (FAM22B-region) breakpoint flanking probes were RP11-715A21 (biotin-labeled) and RP11-668E21 (digoxigenin-labeled). One hundred nuclei per case were evaluated. Paired signals were defined as an orange and green signal less than two signal diameters apart or a single yellow (overlapping) signal, whereas unpaired signals were those separated by greater than or equal to two signal diameters. Only cases with clearly visible probe signals observed in at least 100 nuclei were considered interpretable. A case was considered to be positive for rearrangement if unpaired signals were seen in >20% of nuclei.

Paired-End RNA (Transcriptome) Sequencing and deFuse Analysis:

RNA extraction and sequencing were performed as previously described (22-24). Double-stranded cDNA was synthesized from polyadenylated RNA, and the resulting cDNA was sheared. The 190- to 210-bp DNA fraction was isolated and PCR-amplified to generate the sequencing library, as per the Illumina Genome Analyzer paired-end library protocol (Illumina). The resulting libraries were sequenced on an Illumina GA II. Short read sequences obtained from the Illumina GA II were mapped to the reference human genome (NCBI build 36.1, hg18) plus a database of known exon junctions 2 by using MAQ 3 in paired-end mode. Gene fusions were predicted with deFuse (13), which predicts gene fusions by searching paired-end RNA-sequencing data for reads that harbor fusion boundaries. Spanning reads harbor a fusion boundary in the unsequenced region in the middle of the read, whereas split reads harbor a fusion boundary in the sequence of one end. deFuse searched for spanning reads with read ends that align to different genes. Approximate fusion boundaries implied by spanning reads were then resolved to nucleotide level by using dynamic programming-based alignment of candidate split reads.

RT-PCR and Sequencing:

RNAs from frozen tumor and cell line samples were extracted with a mirVana miRNA Isolation Kit (Ambion) according to the manufacturer's protocol. Reverse transcription was subsequently performed with an iScript cDNA Synthesis Kit to generate cDNA with 1 μg of RNA sample. Forward primers specific for YWHAE (exon 1A: 5'-AGAG-GCTGAGAGAGTC GGAGACA CTA-3' (SEQ ID NO: 81); exon 1B: 5'-TATGGATGATCGAGAGGATCTGGTG-3' (SEQ ID NO: 82); and exon 5: 5'-CAGAAC TGGA-TACGC TGAGT GAAGAA-3' (SEQ ID NO: 83)) and a reverse primer specific for FAM22A/B (exon 2: 5'-CT-CATAGACACT CCTGG GGTTACAGG-3' (SEQ ID NO: 84)) were used. PCR was performed with PCR SuperMix (11306; Invitrogen) according to the manufacturer's protocol with the following cycling conditions: 1 cycle at 94° C. for 2 min followed by 30 cycles of 94° C. for 0.5 min, 55° C. for 0.5 min, 68° C. for 2 min, and a final extension of 68° C. for 5 min. PCR products were evaluated on a 1% agarose gel alongside 1 Kb Plus DNA Ladder (Invitrogen) visualized with ethidium bromide staining. The PCR amplicon bands were excised from the gel, purified with a Qiagen Gel Purification Kit, and sequenced with BigDye Terminator v3.0 Ready Reaction Cycle Sequencing (Applied Biosystems) on an ABI PRISM 310.

Fusion Construct and Cloning:

YWHAE-FAM22A-FLAG fusion cDNA containing BamHI (YWHAE end) and EcoRI (FLAG end) restriction sites was synthesized (GenScript) based on the sequences of the fusion transcript present in ESS1 and cloned in pUC57 vector. The fusion gene sequence was validated by sequencing. It was further subcloned in pCDNA3(+) by EcoRI and BamHI (GenScript). The construct integrity was verified by sequencing. The fusion construct was expressed in 293T cells by a Lipofectamine-based transfection method according to the manufacturer's instructions (Invitrogen Life Technologies).

Cell Lysate Preparation:

Whole-cell lysates were prepared in lysis buffer [1% Nonidet P-40, 50 mM Tris.HCl (pH 8.0), 100 mM sodium fluoride, 30 mM sodium pyrophosphate, 2 mM sodium molybdate, 5 mM EDTA, and 2 mM sodium orthovanadate] containing protease inhibitors (10 µg/mL aprotinin, 10 µg/mL leupeptin, and 1 mM phenylmethylsulfonyl fluoride). Nuclear and cytoplasmic fraction lysates were prepared by using a Qproteome Cell Compartment Kit (Qiagen) according to the manufacturer's protocol. Protein concentrations were determined by using the Bio-Rad Protein Assay.

Western Blotting and Immunoprecipitation Studies:

Electrophoresis and Western blotting were performed as described previously (25). In short, 30 µg of protein was loaded on a 4-12% Bis-Tris gel (NuPAGE; Invitrogen) and blotted onto a nylon membrane. Immunoprecipitations were performed by incubating 1 mg of precleared cell lysate with anti-FLAG (mouse monoclonal, F1804; Sigma) for 2 h at 4° C., followed by addition of 20 µL of protein A Sepharose (Zymed Laboratories) for overnight incubation at 4° C. The immunoprecipitates were then washed three times with lysis buffer and one time with 750 µL of 10 mM Tris (pH 7.4) buffer for 10 mM each at 4° C., before being resuspended in SDS/PAGE loading buffer containing 7.5% β-mercaptoethanol, heated at 95° C. for 5 min, resolved on 4-12% SDS/polyacrylamide gradient gels (NuPAGE; Invitrogen), and transferred to nylon membranes. Adequate protein transfer was demonstrated by staining the membranes with Ponceau S (Sigma Chemical).

The following primary antibodies were used for staining: antibodies raised against N-terminal (amino acids 1-70) YWHAE (rabbit polyclonal, HPA008445; Sigma) and against C-terminal (amino acids 239-255) YWHAE (rabbit polyclonal, BML-SA475R; Enzo Life Sciences), anti-FLAG (mouse monoclonal, F1804; Sigma), anti-FOXO3A (rabbit polyclonal, 9467; Cell Signaling), anti-poly(ADP-ribose) polymerase (PARP, mouse monoclonal, 33-3100; Zymed), and anti-GADPH (mouse monoclonal, G8795; Sigma). Detection was by ECL (Amersham Pharmacia Biotechnology) with a Fuji LAS1000 Plus chemiluminescence imaging system.

Preparation of Lentiviral FAM22A shRNA Constructs and Lentiviral Infections:

FAM22A shRNAs were from Broad Institute RNAi Consortium: FAM22A shRNA1 (NM_001099338.1-3119s21c1), 5'-TCTTGCTGGGCCTTAGCTTTG-3' (SEQ ID NO: 85); and FAM22A shRNA2 (NM_001099338.1-598s21c1), 5'-TATGTTCCAGGAACCTGTTTA-3' (SEQ ID NO: 86). Lentiviral preparations were produced by cotransfecting empty vector pLKO.1 puro with FAM22A shRNA and helper virus packaging plasmids pCMVΔR8.a91 and vsv-g (at a 10:10:1 ratio) into 293T cells. Transfections were carried out with Lipofectamine and PLUS reagent. Lentiviruses were harvested at 24, 36, 48, and 60 h posttransfection. Viruses were frozen at −80° C. in aliquots at appropriate amounts for infection. ESS1 cells were seeded in 6-well plates. Infections were carried out in the presence of 8 µg/mL polybrene. After transduction, ESS1 were selected with 2 µg/mL puromycin for 15 d, then lysed for Western blot analysis. Cell culture images were obtained by using a Spot RT Slider Camera and Spot software (Version 4.6 for Windows) and a Nikon Eclipse TE2000-S inverted microscope.

In Vitro Wound-Healing Assays:

Cell-wounding studies were carried out via standard methods (26). A slash was created in confluent cell cultures, using the tip of a P-100 Pipetman, at 8 d after shRNA transduction with puromycin selection. The plates were photographed at 0, 72, and 96 h with Spot software (Version 4.6 for Windows) and a Nikon Eclipse TE2000-S inverted microscope.

3' End Sequencing Gene-Expression Analysis:

We prepared 3' sequence libraries as previously described (27). Total RNA was purified from formalin-fixed paraffin-embedded sections after deparaffination with a xylene incubation, ethanol wash, and protease/DNase digestion (RecoverAll Total Nucleic Acid Isolation Kit; Ambion) per the manufacturer's protocol. Isolation of the mRNA 3' ends was achieved by oligo(dT) selection on 20 µg of total RNA with the Oligotex mRNA Mini Kit (Qiagen). Insufficiently fragmented RNA was heat-sheared to ~100-200 bp. The poly (A)-selected RNA was then subjected to first- and second-strand cDNA synthesis and Illumina library synthesis. To obtain 36-base single-end sequence reads, 3'-end sequencing for expression quantification (3SEQ) libraries were sequenced with Illumina GA IIx machines. Reads were mapped first to the transcriptome (refMrna, downloaded from the UCSC genome browser at www.genome.ucsc.edu) by using SOAP2, allowing at most two mismatches (28). Unmapped and nonuniquely mapping reads were then mapped against the human genome (hg19), also using SOAP2, and reads mapping to RefSeq exons (same strand) were determined. Total sequence reads for each gene symbol from the transcriptome mapping and genome mapping were summed to create the gene-expression profile matrix. The data were then normalized by expressing the number of reads as transcripts per million reads (TPM) and filtered to select genes with a value of ≥1 TPM in at least two samples and an absolute difference of ≥2 TPM across the series. From these genes, those with an SD≥200 as determined by Cluster 3 software were log-transformed, centered by gene using Cluster 3 software, subjected to unsupervised hierarchical clustering by Centroid linkage, and visualized with Java TreeView. Significance analysis of microarrays (SAM; www-stat.stanford.edu/~tibs/SAM/) was used to identify genes expressed differentially between the tumor groups.

siRNA Study and Cell Viability Assay.

According to the manufacturer's instructions, transfections were carried out with Lipofectamine and PLUS reagent (Invitrogen Life Technologies). Briefly, scrambled control (5'-AAGUUCAGGUCGAUAUGUGCA-3' (SEQ ID NO: 87); Invitrogen Life Technologies) or FAM22 siRNAs (s198355 and s195919; Invitrogen Life Technologies) incubated with PLUS in serum-free medium for 15 min at room temperature, then mixed in diluted Lipofectamine in equal volume with scrambled control or siR-NAs-PLUS mixtures and incubated for another 15 min at room temperature. Finally, siRNA-PLUS-Lipofectamine complexes were added into 60% confluent ESS1 cells under serum-free medium conditions in 6- or 96-well plates. DNA-PLUS-Lipofectamine complexes in serum-free medium were completely replaced with serum-containing regular medium after a 3-h incubation. Cells were lysed for Western blot analysis at 96 h posttransfection, and cell viability was determined after 96 h posttransfection with the CellTiter-Glo luminescent assay from Promega. The viability data were normalized to the scrambled control group. All assays were performed in quadruplicate wells and averaged from two independent transfections in ESS1 cells.

Quantitative Cell Migration Assay.

Transfections of NIH 3T3 cells were carried out with Lipofectamine and PLUS reagent(Invitrogen Life Technologies) according to the manufacturer's protocol. At 24 h posttransfection, 0.5 mL of serum-free media containing 5×10⁴ NIH 3T3 cells was plated per BD BioCoat8.0-μm PET Membrane 24-well Cell Culture Insert (no. 354578; BD Biosciences). Next, the wells were fed with 0.75 mL of Iscove's modified Dulbecco's medium containing 15% FBS and incubated in a humidified incubator at 37° C., 5% $CO_2$ for 60 h. The media from the inside of the insert was aspirated, and the interiors of the inserts were gently swabbed to remove nonmigratory cells. Inserts were transferred to new wells containing 400 μL, of Cell Stain Solution (no. 11002; Cell Biolabs) and incubated for 10 min at room temperature, then rinsed two times in a beaker of water. Then the inserts were air-dried, imaged with a scanner, and quantified with a micro-plate reader.

Results and Discussion

Figure 5:
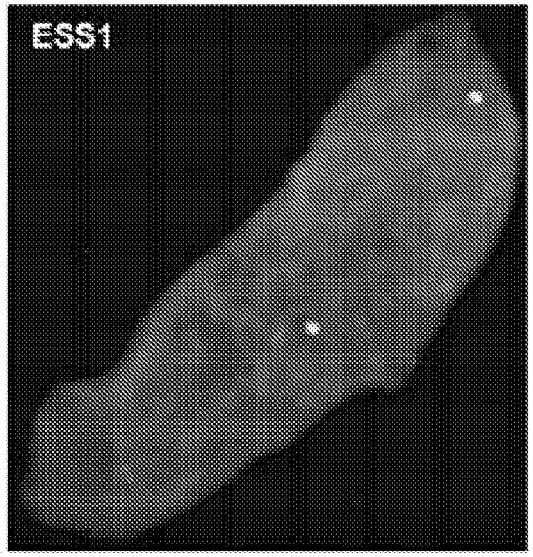
FIGS. 5A and 5B show results of FISH studies.
Figure 5:
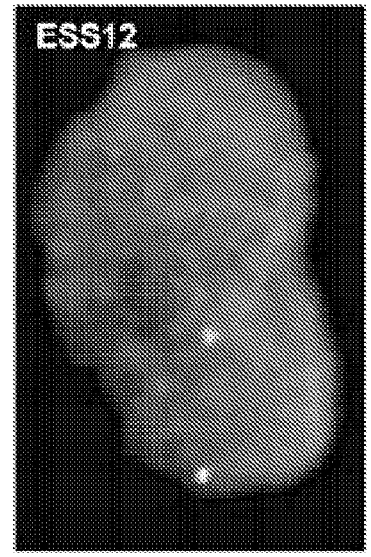
Figure 5:
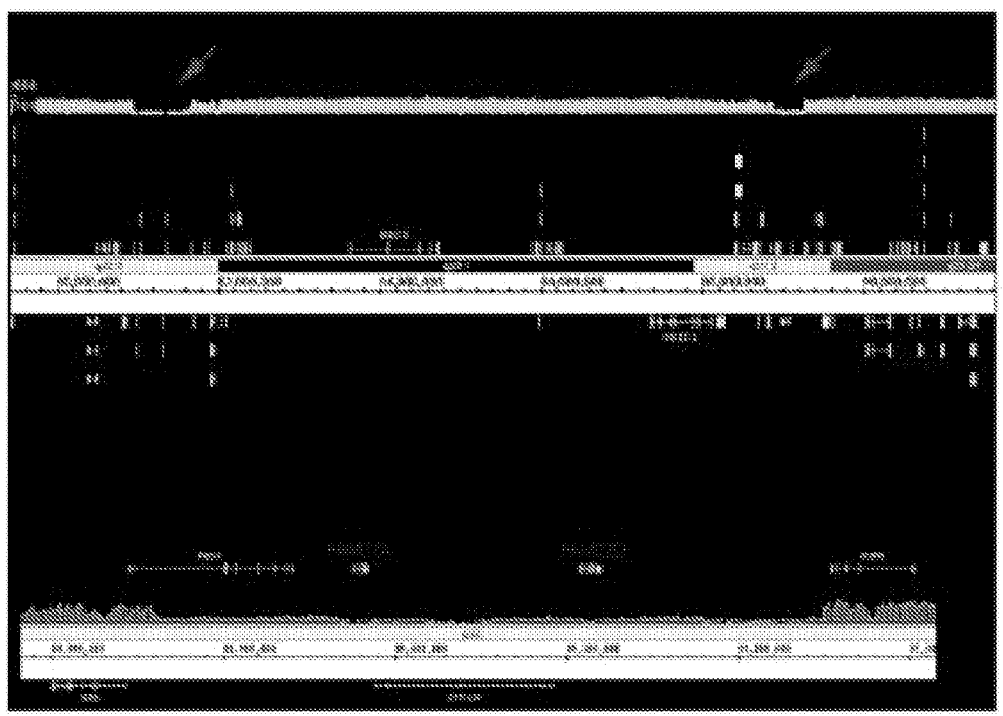

Cytogenetics and Whoe-Transcriptome Sequencing Identifies YWHAE-FAM22A/B Fusion as a Frequent Recurrent Genetic Event in High-Grade ESS To characterize the genetic basis of high-grade ESS, we performed prospective cytogenetic G-banding analyses, which identified a translocation, t(10;17)(q22;p13), as a recurrent and predominant aberration in 7 of 12 cases (FIG. 1A and Table 1). A spontaneously immortal cell line, ESS1, was established from one of these t(10;17)-bearing ESS. Fluorescence in situ hybridization (FISH) localized the ESS 17p13 translocation breakpoint to the YWHAE (14-3-3c) gene (FIG. 1B). In contrast to the tumor cells, the adjacent normal myometrial tissues uniformly lacked YWHAE rearrangement by FISH, confirming the somatic nature of the rearrangement. One ESS had an unbalanced t(10;17), associated with deletion of the rearranged YWHAE 3' end, thereby implicating the YWHAE 5' end in a putative t(10; 17)-associated fusion oncogene. FISH localizations mapped the 10q translocation breakpoint, in each t(10;17) ESS, to one of two regions (10q22.3 and 10q23.2) separated by 7.8 megabases (FIG. 5): notably, these regions had gnomic and organizational similarities, each containing two members of the FAM22 family. FISH mapping within these regions was hampered by the repetitive nature of the genomic sequences (FIG. 5). Because of the abundant expression of wild-type YWHAE, 3' RACE analysis was unsuccessful.

TABLE 1

Karyotypes of 12 histologically high grade endometrial stromal sarcomas

| Case number | Karyotype |
|---|---|
| 1 | 46, XX, t(10; 17)(q22; p13) |
| 2 | 46, XX, t(10; 17)(q22; p13) |
| 3 | 43, XX, der(5)t(5; 21)(q35; q11), |

TABLE 1-continued

Karyotypes of 12 histologically high grade endometrial stromal sarcomas

| Case number | Karyotype |
|---|---|
|  | der(9; 11)(q10; q10), −10, t(10; 17)(q22; p13), −21 |
| 4 | 55-58, XX, del(X)(p11.2), +1, i(1)(q10), +2, +3, +4, +6, del(6)(q21), +7, −9, +12, del(12)(q21), +15, +17, +22, add(22)(q12) × 2, +2r |
| 5 | 44, XX, t(10; 17)(q22; p13), del(11)(q1?2), −19, −22 |
| 6 | 46, XX, inv(6)(p21q13)[10] |
| 7 | 46, XX, del(X)(p22.1), +1, ?dup(1)(q42), i(1)(q10), +2, +3, +4, t(4; 7)(q21; p22), +7, −9, +12, +17, der(17)t(5; 17)(p11; p11), +22, add(22)(q13) × 2, +2-4mar |
| 8 | 46, X, der(X)t(X; 1)(p22; q24), dup(1)(q12q32) |
| 9 | 45, X, −X, t(10; 17; 12)(q22; p11.2; q13), add(19)(p13.3) |
| 10 | 47, XX, der(9)del(9)(p11)del(9)(q12), del(10)(q22), der(11)t(9; 11)(q12; q12), der(17)t(10; 17)(q22; p13), +19 |
| 11 | 47, XX, +i(1)(q10), t(9; 9)(p24; q11), add17(p13), −16, +mar |
| 12 | 46, XX, t(10; 17)(q22; p13) |

To demonstrate a putative YWHAE fusion oncogene in these genomically repetitive 10q regions, we used whole-transcriptome sequencing as an unbiased method. Sequencing was performed against the t(10;17)-containing, ESS1, and sequence reads were analyzed by using a custom-written defuse algorithm designed to identify fusion transcripts in RNA sequencing datasets (13), including those involving members of highly homologous gene families. deFuse analysis identified in-frame YWHAE-FAM22A fusions of YWHAE exon 5 to FAM22A exon 2 (FIG. 1C and Table 2). FAM22A is located within the 10q23.2 breakpoint region, whereas the alternate breakpoint region, 10q22.3, contains F4M22B (encoding a protein with 99% amino acid identity to FAM22A) and FAM22L RT-PCR with YWHAE forward primers and consensus reverse primers for FAM22A/B/E identified YWHAE-FAM22B fusion transcripts in each t(10; 17) ESS that lacked YWHAE-FAM22A (FIG. 1D). Therefore, FAM22A and FAM22B are alternative YWHAE gene fusion partners (FIG. 1E). In all cases, the genetic rearrangements in transcribed YWHAE-FAM22 involved fusion of YWHAE exon 5 to FAM22A or FAM22B exon 2, creating a fusion coding sequence consistent with genomic breakpoints in YWHAE intron 5 and FAM22A/B intron 1. FAM22A and FAM22B have sequence homology with NUT, an oncogene fused to BRD4 and BRD3 bromodomain genes in NUT midline carcinoma (14, 15). The YWHAE-FAM22A fusion transcript is 2,970 bp in length, and the corresponding protein product contains 989 aa, with a predicted molecular mass of 108 kDa (SEQ ID Nos: 1-4 and GenBank accession nos. JN999698 and JN999699)

TABLE 2

Summary of the result of deFuse analysis in ESS1 (including only fusion transcripts with >0.9 prediction probability and sorted by transcript count).

| Gene_name 1 | Gene_name 2 | Split transcript count | breakpoint homology | Coding 1 | Coding 2 | deletion | eversion | Exonic 1 | Exonic 2 | Expression 1 | Expression 2 |
|---|---|---|---|---|---|---|---|---|---|---|---|
| FAM22A | YWHAE | 76 | 1 | Y | Y | N | N | Y | Y | 340 | 9303 |
| BIRC1 | AC139834.2 | 63 | 1 | Y | N | N | N | Y | N | 8850 | 88 |
| KIAA1267 | ARL17 | 49 | 4 | Y | Y | N | Y | Y | Y | 3871 | 1792 |
| ARL17P1 | KIAA1267 | 47 | 4 | Y | Y | N | Y | Y | Y | 1863 | 3871 |

TABLE 2-continued

Summary of the result of deFuse analysis in ESS1 (including only fusion transcripts with >0.9 prediction probability and sorted by transcript count).

| Gene_name 1 | Gene_name 2 | Split transcript count | breakpoint homology | Coding 1 | Coding 2 | deletion | eversion | Exonic 1 | Exonic 2 | Expression 1 | Expression 2 |
|---|---|---|---|---|---|---|---|---|---|---|---|
| IGLV5-52 | BMS1 | 34 | 4 | Y | Y | N | N | Y | Y | 29 | 1976 |
| KIAA1267 | ARL17P1 | 34 | 4 | Y | Y | N | Y | Y | Y | 3871 | 1863 |
| AL159167.23-1 | C9orf102 | 28 | 66 | Y | Y | Y | N | Y | Y | 190 | 644 |
| GTF2H2 | BIRC1 | 26 | 2 | Y | Y | N | Y | Y | Y | 1374 | 8850 |
| BIRC1 | AC140134.2-2 | 25 | 2 | Y | Y | N | Y | Y | Y | 8850 | 3264 |
| BACH1 | AF124731.2 | 24 | 2 | Y | Y | N | N | Y | Y | 3428 | 19 |
| C18orf32 | RPL37P33 | 20 | 2 | Y | Y | N | N | Y | Y | 1765 | 9711 |
| RMND5A | ANAPC1 | 19 | 3 | Y | Y | N | N | Y | Y | 1371 | 1945 |
| IFNGR2 | TMEM50B | 18 | 2 | N | N | Y | N | N | N | 1463 | 3079 |
| D87018.1-3 | IGLV5-52 | 16 | 4 | N | Y | Y | N | N | Y | 8 | 29 |
| CKMT2 | ZCCHC9 | 15 | 2 | N | N | Y | N | N | N | 139 | 712 |
| AC103702.3 | HOXB5 | 14 | 1 | Y | N | Y | N | Y | N | 28 | 124 |
| AC145138.2-1 | GUSBL2 | 14 | 5 | Y | Y | N | N | Y | Y | 49 | 158 |
| MRPS5 | ZNF514 | 13 | 1 | N | N | Y | N | N | Y | 979 | 1235 |
| TSHZ2 | SLC35A1 | 11 | 2 | N | N | N | N | N | N | 2950 | 959 |
| AC010326.7-2 | ZNF587 | 11 | 3 | Y | N | Y | N | Y | N | 135 | 3298 |
| FBXO25 | BET1L | 10 | 4 | Y | Y | N | N | Y | Y | 506 | 773 |
| SLC25A6 | IL3RA | 10 | 2 | Y | Y | Y | N | Y | Y | 6782 | 122 |
| MTHFD1 | ZBTB25 | 10 | 2 | Y | Y | Y | N | Y | Y | 856 | 302 |
| DPYSL2 | PNMA2 | 10 | 3 | Y | N | Y | N | Y | N | 4132 | 3142 |
| MTO1 | EEF1A1 | 10 | 2 | N | Y | Y | N | N | Y | 662 | 527400 |
| KPNA2 | SNRNP200 | 10 | 0 | Y | Y | N | N | Y | Y | 680 | 10065 |
| ANKDD1A | SPG21 | 10 | 8 | Y | Y | Y | N | Y | Y | 281 | 2825 |
| GTF2H2 | BIRC1 | 8 | 2 | N | Y | N | Y | N | Y | 1374 | 8850 |
| AC024270.6 | TM6SF1 | 7 | 2 | Y | N | Y | N | Y | N | 1817 | 105 |
| EIF3CL | PDXDC2 | 7 | 4 | Y | N | N | Y | Y | Y | 3865 | 2617 |
| YY1 | SLC25A29 | 7 | 2 | N | N | Y | N | N | Y | 1840 | 1521 |
| GOLGA7B | CRTAC1 | 7 | 2 | N | Y | Y | N | N | Y | 387 | 1889 |
| CSAD | ZNF740 | 7 | 3 | N | Y | Y | N | N | Y | 1881 | 1069 |
| GP1BA | CHRNE | 6 | 10 | Y | Y | Y | N | Y | Y | 178 | 452 |
| FALZ | ARL17 | 6 | 2 | Y | Y | N | N | Y | Y | 8711 | 1792 |
| BTBD7 | OPTN | 6 | 3 | Y | N | N | N | Y | N | 2154 | 255 |
| YARS2 | DNM1L | 6 | 0 | Y | N | Y | N | Y | N | 510 | 3557 |
| B9D1 | EPN2 | 6 | 10 | Y | N | Y | N | Y | N | 106 | 3274 |
| DNAJC2 | PMPCB | 6 | 188 | N | Y | Y | N | N | Y | 862 | 2433 |
| FBXW2 | AL161911.17 | 5 | 4 | N | Y | Y | N | N | Y | 3984 | 114 |
| EGLN2 | CYP2F1 | 5 | 2 | Y | Y | N | N | Y | Y | 588 | 9 |
| SAV1 | GYPB | 5 | 7 | Y | Y | N | N | Y | Y | 984 | 163 |
| DNAJB4 | FUBP1 | 5 | 2 | Y | N | Y | N | Y | N | 1702 | 4211 |
| VPS45 | PLEKHO1 | 5 | 3 | Y | Y | Y | N | Y | Y | 1676 | 334 |
| LRRC37A | NSF | 5 | 0 | Y | Y | N | Y | Y | Y | 1435 | 2154 |
| HEXA | BRUNOL6 | 5 | 4 | Y | Y | Y | N | Y | N | 2233 | 544 |
| PRKAA1 | TTC33 | 4 | 2 | Y | Y | Y | N | Y | Y | 4151 | 1190 |
| ADSL | SGSM3 | 4 | 3 | Y | Y | Y | N | Y | Y | 1390 | 905 |
| RPS23 | ATG10 | 4 | 3 | Y | Y | Y | N | Y | Y | 28000 | 198 |
| EGLN2 | CYP2F1 | 4 | 2 | Y | Y | N | N | Y | Y | 588 | 9 |
| USO1 | G3BP2 | 4 | 3 | N | Y | Y | N | N | Y | 4612 | 5924 |
| USP45 | SFRS18 | 4 | 2 | N | N | Y | N | N | N | 1083 | 7585 |
| PEX13 | KIAA1841 | 4 | 10 | Y | Y | Y | N | Y | Y | 654 | 384 |
| AL133216.10-2 | PCMTD2 | 4 | 2 | N | Y | N | N | N | Y | 598 | 4820 |
| AC138894.2-2 | PDXDC2 | 4 | 376 | Y | N | Y | N | Y | Y | 26 | 2617 |
| AC073135.3-3 | LMLN | 3 | 3 | N | N | Y | N | N | N | 93 | 220 |
| ENTPD7 | COX15 | 3 | 2 | Y | Y | Y | N | N | Y | 502 | 2450 |
| CENPB | CDC25B | 3 | 3 | N | Y | Y | N | N | Y | 1088 | 1274 |
| GKAP1 | KIF27 | 3 | 3 | N | N | N | Y | Y | Y | 373 | 941 |
| SLC12A7 | NKD2 | 3 | 2 | N | Y | Y | N | N | Y | 1529 | 887 |
| ENPP3 | CRSP3 | 3 | 0 | Y | N | Y | N | Y | N | 2424 | 2947 |
| DHTKD1 | SEC61A2 | 3 | 2 | Y | Y | Y | N | Y | Y | 1228 | 776 |
| TMEM14B | MAK | 3 | 3 | Y | Y | Y | N | Y | Y | 1378 | 126 |
| RPL24P6 | AC084198.31-2 | 3 | 6 | Y | N | Y | N | Y | Y | 13085 | 67 |
| IL17D | N6AMT2 | 2 | 3 | N | N | Y | N | N | N | 191 | 320 |
| ZNF649 | ZNF577 | 1 | 2 | Y | N | Y | N | Y | Y | 617 | 669 |
| FOXO3B | Z95118.1 | 1 | 3 | Y | Y | N | N | Y | Y | 103 | 7 |
| CLSTN1 | CTNNBIP1 | 1 | 1 | Y | Y | Y | N | Y | Y | 12529 | 976 |
| AC005488.2-6 | AC005488.2-4 | 1 | 3 | N | N | Y | N | Y | Y | 258 | 202 |
| REXO4 | ADAMTS13 | 1 | 0 | N | Y | Y | N | N | Y | 428 | 277 |

Expression 1 and Expression 2 represent the total number of reads aligned uniquely to Gene 1 and Gene 2 respectively, while the Split transcript count represents the number of split reads where the fusion sequence aligns to each of these genes or to an indistinguishable family member (a measure that facilitates the identification of fusions involving genes with highly homologous family members). Only YWHAE-FAM22A fusion (highlighted in yellow) was experimentally tested and validated.

YWHAE-FAM22 is Expressed in t(10;17)-Bearing High-Grade ESS and Demonstrates Transforming Properties.

Figure 6:
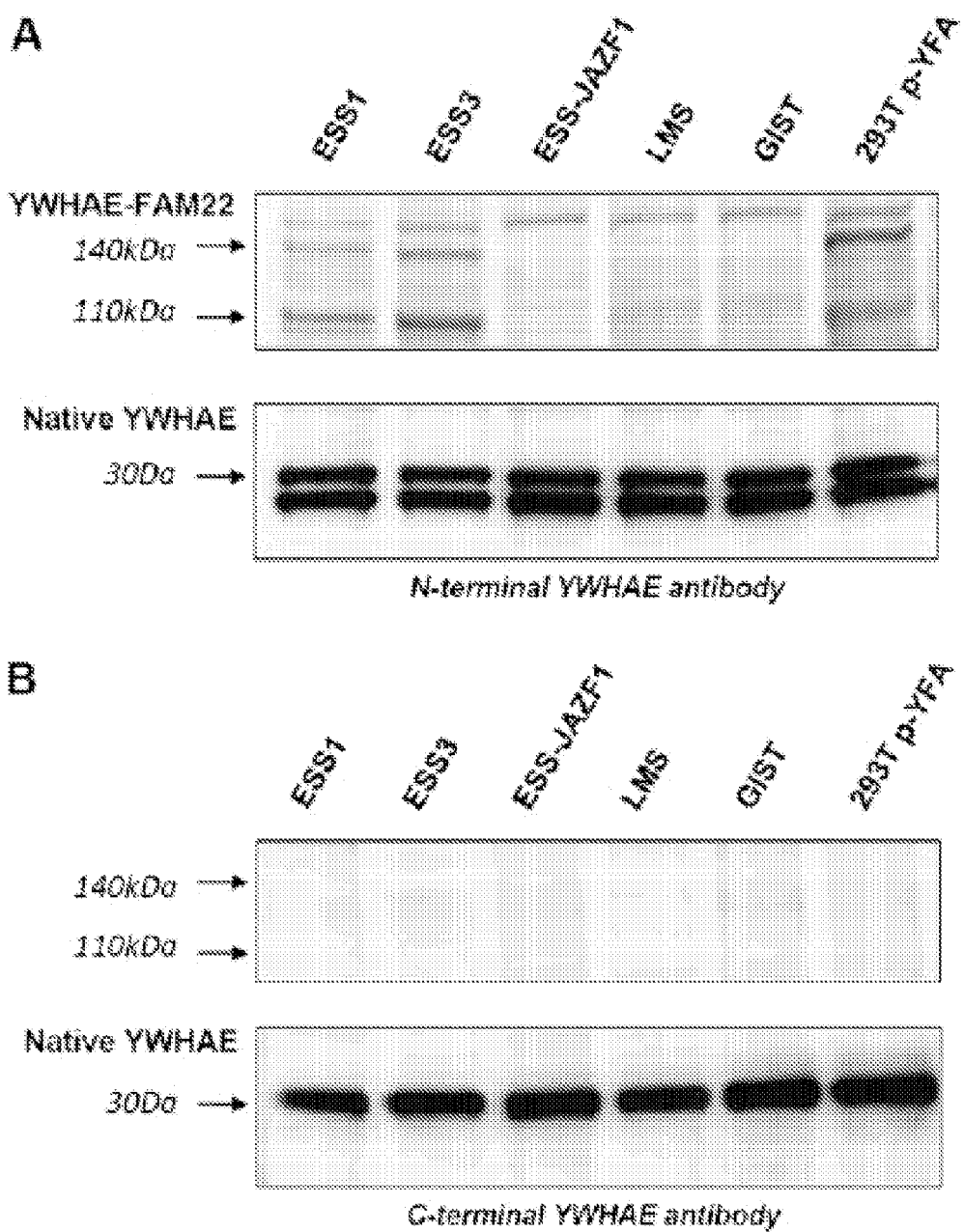
FIGS. 6A and 6B show YWHAE-FAM22 fusion protein expression. YWHAE-FAM22 is expressed in high-grade cancers with t(10;17) (ESS1 and ESS3) but not in low-grade ESS JAZF1-SUZ12 (ESS-JAZF1), leiomyosarcoma (LMS), or gastrointestinal stromal tumor (GIST). The lane marked 293 p-YFA contains 293T cells expressing FLAGtagged YWHAE-FAM22A pcDNA3 construct. YWHAE-FAM22 alternate forms (~110 kDa and ~140 kDa) were demonstrated by an N-terminal YWHAE antibody (HPA008445; Sigma; developed against a peptide containing amino acids 1 to ~0.70 of YWHAE) but not by a C-terminal YWHAE antibody (BML-SA475; Enzo Life Sciences; developed against a peptide containing amino acids 239 to ~255 of YWHAE, a region encoded by YWHAE exon 6), whereas both N-terminal and C-terminal YWHAE antibodies identified the wild-type YWHAE (~0.30 kDa). The N-terminal YWHAE antibody also identified other native 14-3-3 family proteins, represented by the lower bands (~0.27 kDa).

To identify expression of YWHAE-FAM22A and YWHAE-FAM22B, Western blotting was performed with N-terminal and C-terminal YWHAE antibodies, of which only the N-terminal antibody was expected to recognize the fusion proteins. Although both antibodies identified ~30-kDa wild-type YWHAE in all tumor samples examined, only the N-terminal YWHAE antibody identified putative YWHAE-FAM22A/B fusion proteins, which were represented in each t(10;17) ESS by bands at 110 kDa and 140 kDa (FIG. 6). The 110-kDa form corresponds to the predicted molecular mass for YWHAE-FAM22A/B, whereas the 140-kDa form presumably represents a mature form of the fusion protein, after posttranslational modifications. YWHAE-FAM22A/B expression was considerably lower than that of the native YWHAE, in keeping with the whole-transcriptome sequence data that showed eight times fewer YWAE-FAM22A reads than wild-type YWHAE reads in the breakpoint region. YWHAE-FAM22A/B oncoproteins were not detected in ESS or other sarcomas lacking t(10:17) nor were they detected in t(10:17) ESS by using antibodies to the YWHAE C-terminal region. Furthermore, endogenous ESS YWHAE-FAM22A/B fusion proteins comigrated with a FLAG-tagged YWHAE-FAM22A pcDNA3 construct expressed in HEK 293T cells (FIG. 6). These studies demonstrated equivalent YWHAE-FAM22A/B expression levels in t(10;17) ESS biopsy specimens compared with the ESS1 immortal cell line.

Figure 7:
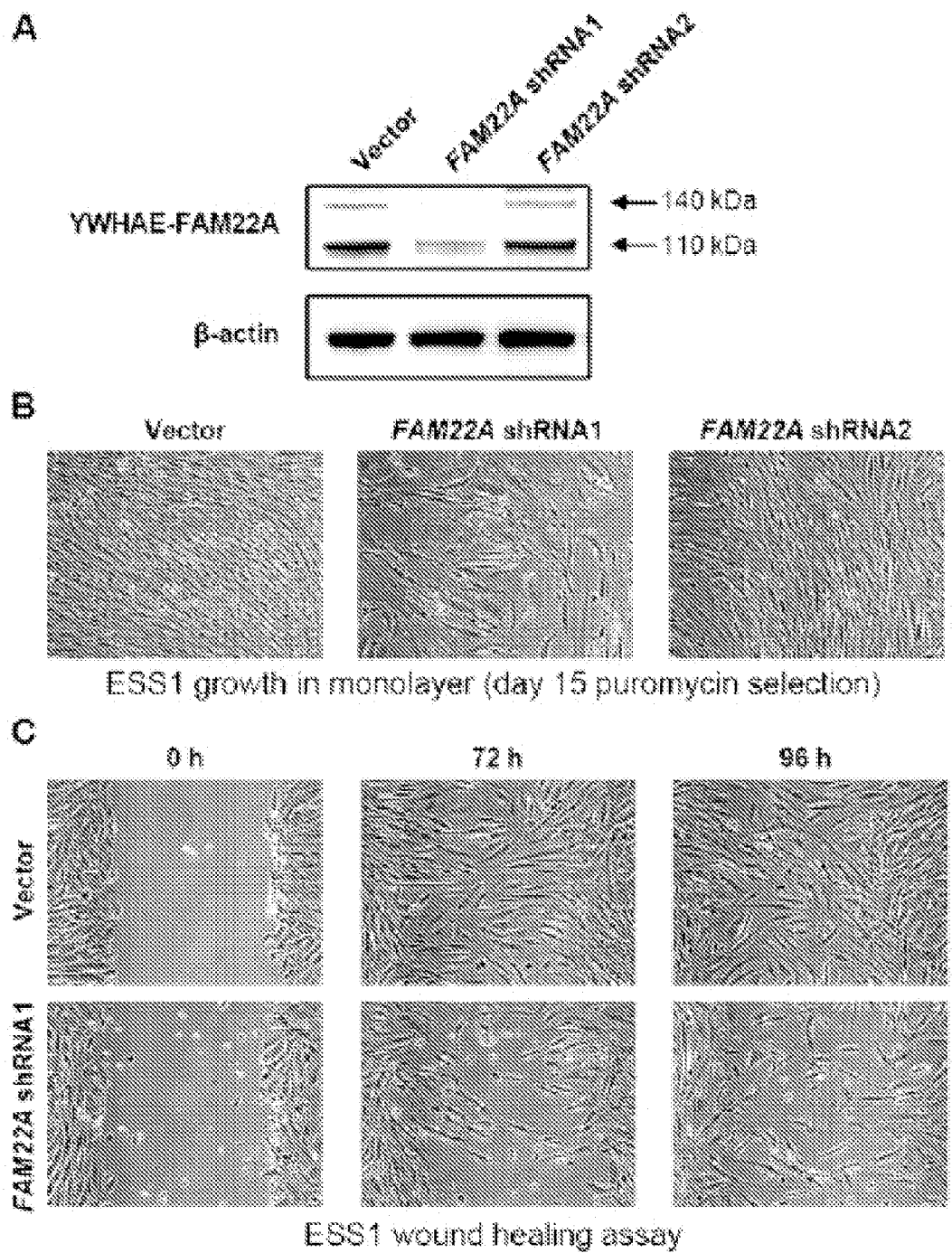
FIG. 7A is an immunoblot showing inhibition of YWHAE-FAM22A fusion protein expression in ESS1 infected with shRNA1 (targets exon 2 of FAM22A), but not in ESS1 infected with empty lentiviral vector or shRNA2 (targets exon 1 of FAM22A, which is not in the YWHAE-FAM22A fusion gene).
FIG. 7B shows representative images of ESS1 in monolayer culture showing reduced cell growth (at 15 d) in ESS1 infected with shRNA1 compared with lentiviral empty vector or shRNA2.
FIG. 7C shows results of a wound healing assay showing reduced cell migration of ESS1 infected with shRNA1 compared with lentiviral empty vector.
Figure 8:
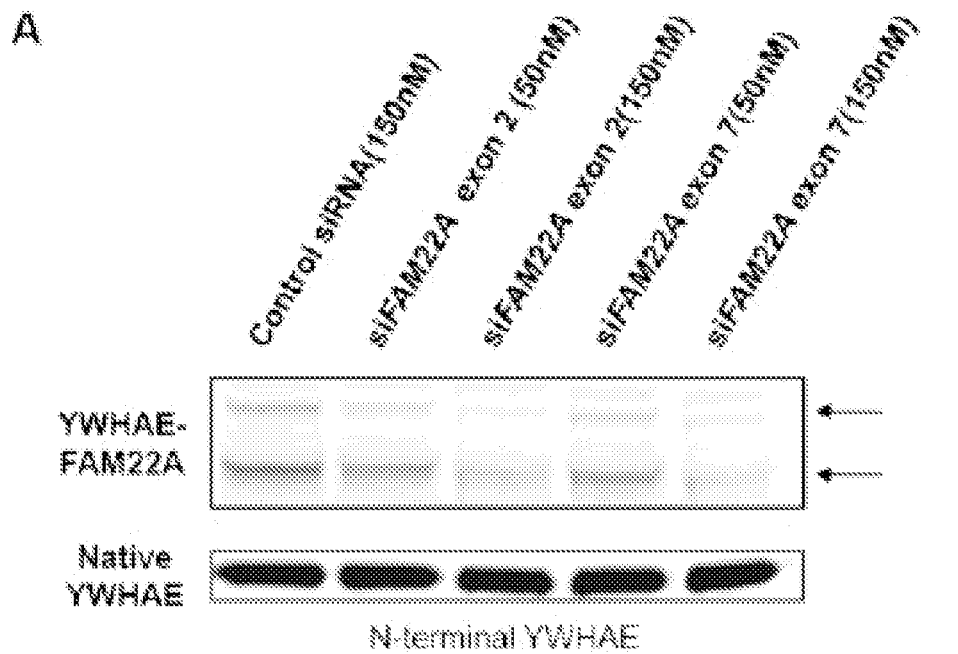
FIGS. 8A and 8B show that siRNA targeting exon 2 and exon 7 of FAM22A (siFAM22A) reduced YWHAE-FAM22A fusion protein expression (N-terminal YWHAE immunoblot (FIG. 8A) and cell viability (CellTiter Glo luminescence assay) (FIG. 8B) in ESS1 containing YWHAE-FAM22A (day 4 after Lipofectamine transfection). Error bars indicate SEs.
Figure 8:
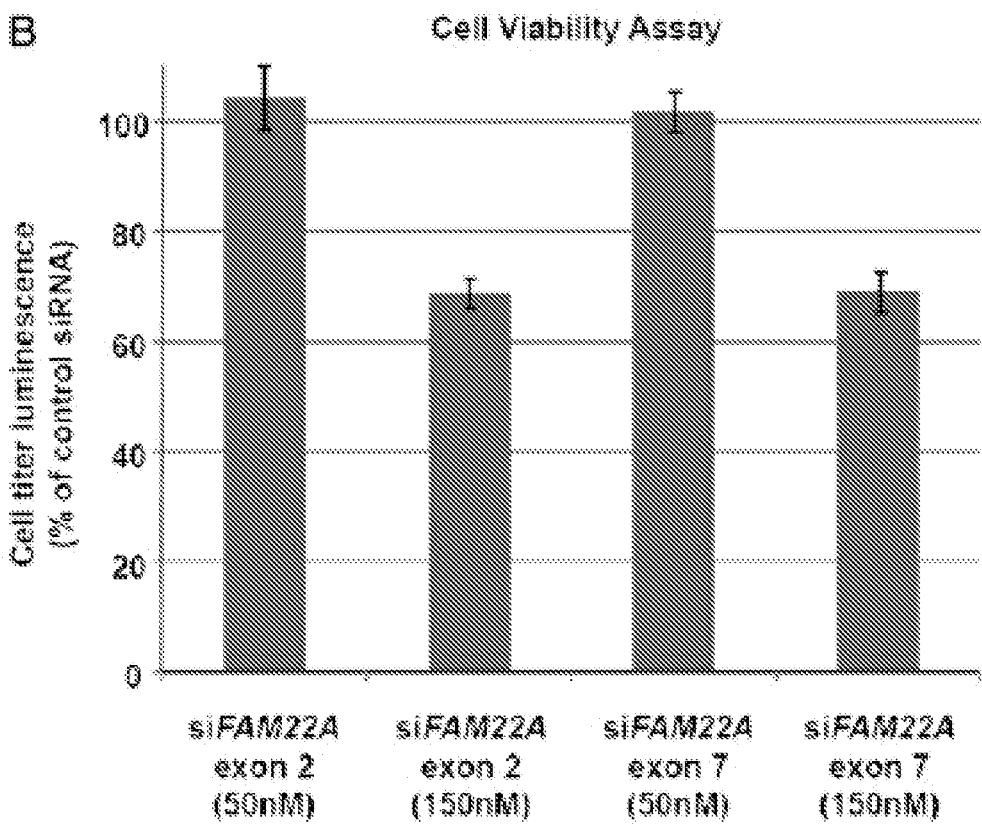

YWHAE-FAM22A oncogenic roles were evaluated in t(10;17) ESS1 cells by using shRNAs and siRNAs targeting FAM22A. FAM22A shRNA1 targets exon 2, which is contained in the fusion transcript. A control sequence, FAM22A shRNA2, targets exon 1, which is not in the fusion transcript, and is expected to inhibit wild-type FAM22A/B/D/E. The nonfusion transcript is minimal to absent in virtually all adult tissues and cancers (www.ncbi.nlm.nih.gov/sites/entrez?db=unigene), and ESS1 whole-transcriptome sequencing showed that only 3% of reads in the breakpoint region were wild-type (unrearranged) FAM22A, whereas 97% were fusion YWHAE-FAM22A, indicating that wild-type FAM22A is expressed at low levels in ESS1. In contrast to empty vector and shRNA2, gene knockdown with shRNA1 inhibited YWHAE-FAM22A expression (110- and 140-kDa forms) in ESS1, with a corresponding reduction in viability and migration (FIG. 7). Similarly, ESS1 transfection with siRNAs targeting FAM22A exons 2 or 7 inhibited YWHAE-FAM22A expression, with corresponding reduction in ESS1 cell viability (FIG. 8). YWHAE-FAM22A transforming activity was further evaluated in mouse embryonic fibroblast 3T3 cells, where YWHAE-FAM22A but not YWHAE transfection induced cell viability and migration (FIGS. 2A-2C).

YWHAE-FAM22 Maintains 14-3-3 Binding Properties and Shows Aberrant Nuclear Localization.

Figure 2:
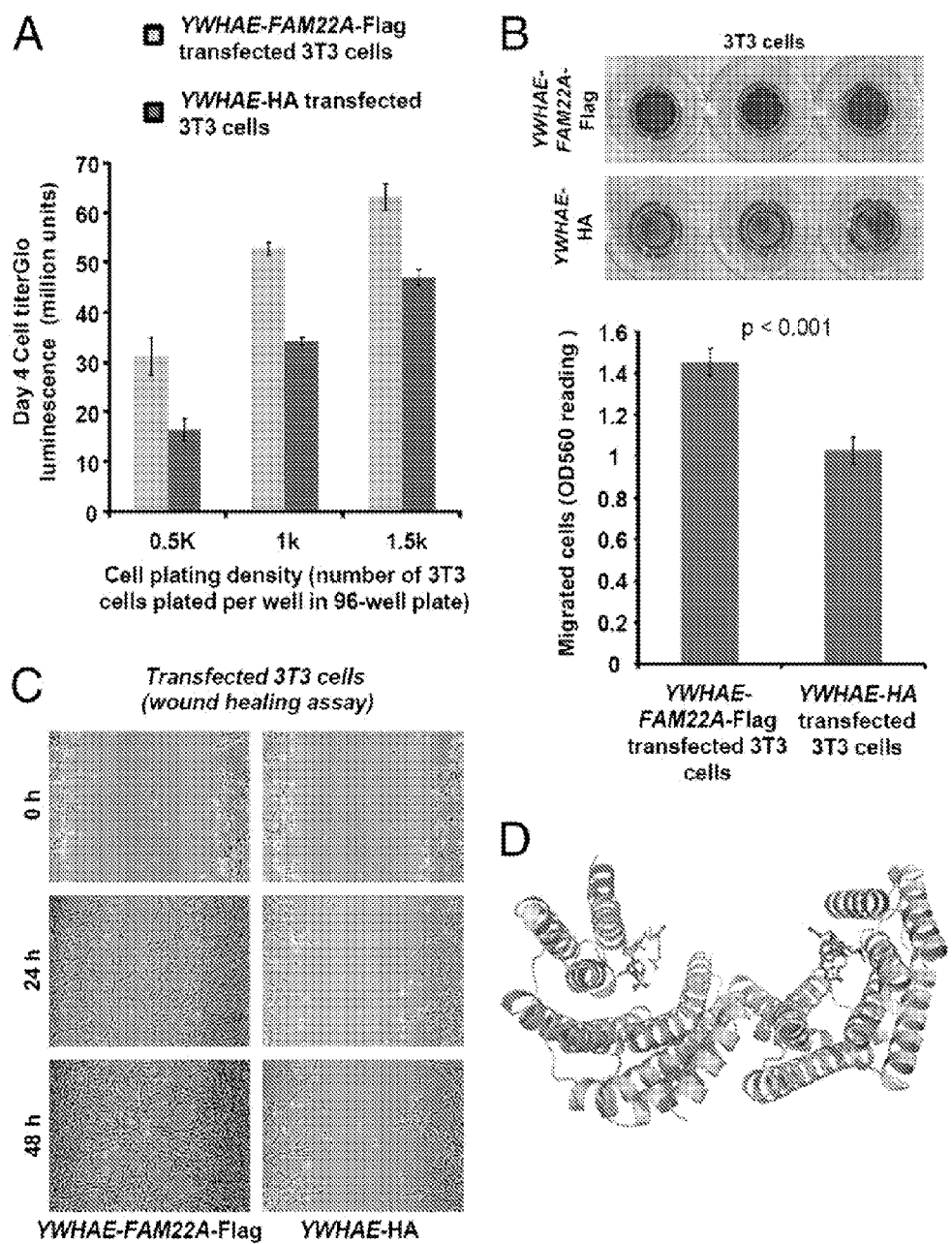
FIGS. 2A-2D show the oncogenic roles of YWHAE-FAM22A fusion oncoprotein and structural considerations.
Figure 3:
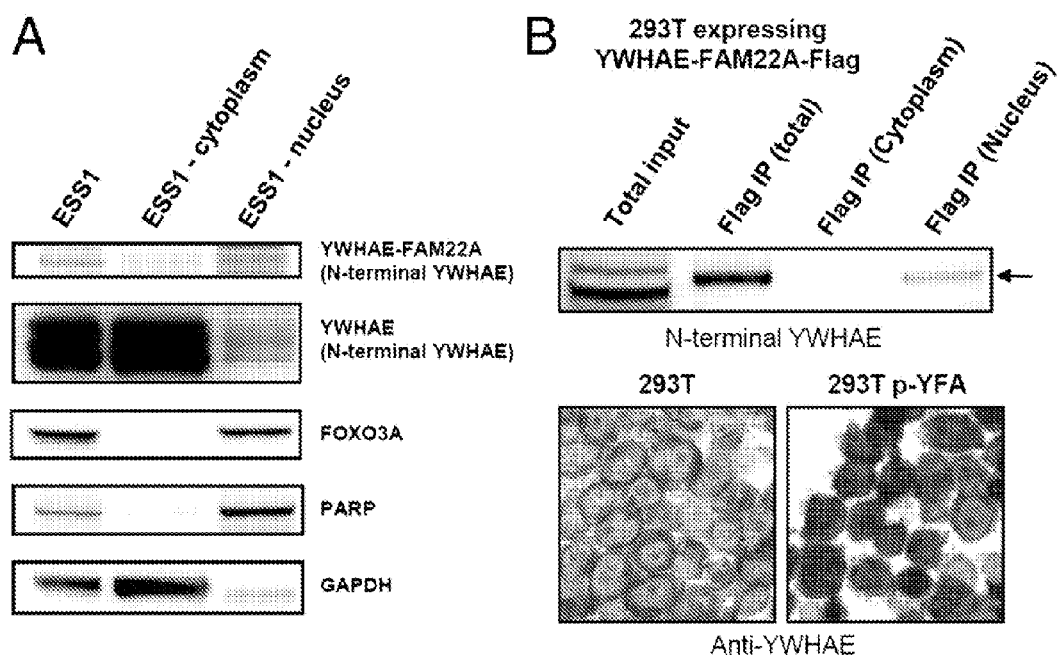

Structurally, the YwHAE-FAM22A/B oncoproteins contain an intact YWHAE protein-interaction domain (16), and loss of the YWHAE C-terminal end (encoded by YWHAE exon 6) and fusion to FAM22A/B are not predicted to functionally impair this rigid YWHAE protein-interaction domain or its ability to dimerize (FIG. 2D). Further analysis of FAM22A/B protein sequences revealed a bipartite nuclear localization sequence (Arg-805 to Arg-822) encoded by exons 7 of FAM22A and FAM22B. In contrast to native YWHAE protein, which is predominantly cytoplasmic (17), YWHAE-FAM22A/B was predicted to be predominantly nuclear (18-20). YWHAE-FAM22A/B nuclear localization was confirmed in ESS1 (FIG. 3A) and in 293T cells expressing a YWHAE-FAM22A construct (FIG. 3B).

YWHAE-FAM22 ESS Display Higher-Grade Histology and More Aggressive Clinical Course Compared with JAZF1-Rearranged ESS.

Figure 4:
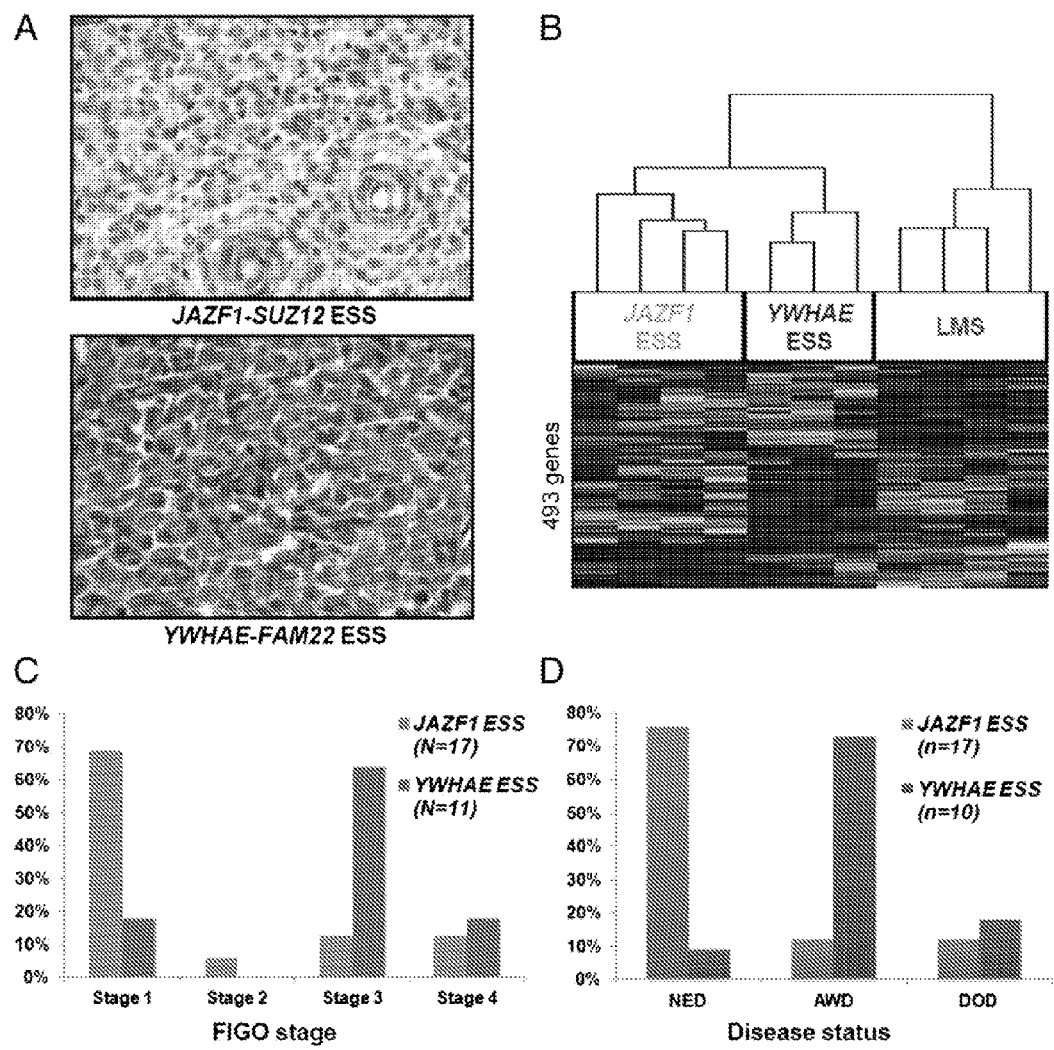
FIGS. 4A-4D show that YWHAE-FAM22 ESS is associated with distinctive histology, gene-expression profiles, and clinical behavior.

Histologically, the 12 clinical cases YWHAE-FAM22A/B ESS (Table 3) exhibited high-grade cytologic features compared with classic non-t(10;17) ESS (FIG. 4A). In contrast to JAZF1-rearranged ESS, which displayed uniform small round/oval nuclei and low proliferation rate (<5 mitotic figures per 10 high-power fields), YWHAE-FAM22A/B ESS showed enlarged nuclei with more irregular nuclear contour and high proliferation rate (>10 mitotic figures per 10 high-power fields). Gene-expression profiling by 3' mRNA sequencing demonstrated a distinctive expression profile in YWHAE-FAM22A/B ESS compared with JAZF1-rearranged ESS and uterine leiomyosarcoma (FIG. 4B). Genes involved in the regulation of cell proliferation (CCND1 and CEBPA) and tissue invasion (MMP15, FSCN1, and TIMP1) were up-regulated in YWHAE-FAM22A/B ESS compared with JAZF1-rearranged ESS (Table 4). Clinically, patients with YWHAE-FAM22A/B ESS presented with higher-stage disease and experienced more frequent disease recurrence compared with patients with JAZF1-rearranged ESS (FIGS. 4C and 4D). FISH analysis demonstrated absolute diagnostic specificity of YWHAE-FAM22A/B rearrangement for high-grade ESS (Table 5). In addition, YWHAE-FAM22A/B rearrangement and JAZF1 rearrangement were mutually exclusive, and YWHAE-FAM22A/B rearrangement was not found in low-grade ESS (n=38) or in various uterine and nonuterine mesenchymal tumors (55 tumor types, n=827) (Table 6). These findings show that. YWHAE-FAM22A/B rearrangement defines ea group of uterine sarcomas that is genetically, histologically, and clinically distinct from classic JAZF1-rearranged ESS. This evidence prompts reconsideration of the current classification of endometrial sarcomas. In the present study, we refer to this genetically unique subgroup as YWHAE-FAM22:41.8 ESS. An alternative classification consideration would be "14-3-3 ESS," which has the advantage of brevity while reflecting the expected biological contributions of YWHAE dysregulation. A biologic classification seems preferable to "high-grade ESS," which misleadingly suggest biologic continuum with the genetically distinct JAZF1 low-grade ESS.

TABLE 3

Summary of clinicopathologic features of 12 YWHAE-FAM22A/B ESS.

| Case | Age | Tumor examined | Histology | Clinical stage | Follow-up | FISH/RT-PCR |
|---|---|---|---|---|---|---|
| 1 | 67 | Primary uterine tumor | High grade ESS | FIGO stage 1C | Alive with disease | YWHAE-FAM22A |
| 2 | 45 | Primary uterine tumor | High grade ESS | FIGO stage 4B | No evidence of disease | YWHAE-FAM22A |
| 3 | 43 | Metastatic tumor (lung) | High grade ESS | not available | not available | YWHAE-FAM22B |

TABLE 3-continued

Summary of clinicopathologic features of 12 YWHAE-FAM22A/B ESS.

| Case | Age | Tumor examined | Histology | Clinical stage | Follow-up | FISH/RT-PCR |
|---|---|---|---|---|---|---|
| 4 | 47 | Metastatic tumor (lung) | High grade ESS | FIGO stage 1A | Alive with disease | YWHAE-FAM22B |
| 5 | 62 | Primary uterine tumor | High grade ESS | FIGO stage 3 | Alive with disease | YWHAE-FAM22B |
| 6 | 54 | Primary uterine tumor | High grade ESS | FIGO stage 4B | Alive with disease | YWHAE-FAM22B |
| 7 | 49 | Primary uterine tumor | High grade ESS | FIGO stage 4B | Died of disease | YWHAE-FAM22B |
| 8 | 49 | Primary uterine tumor | High grade ESS | FIGO stage 3B | not available | YWHAE-FAM22B |
| 9 | 57 | Primary uterine tumor | High grade ESS | FIGO stage 3C | Died of disease | YWHAE-FAM22B |
| 10 | 28 | Primary uterine tumor | High grade ESS | FIGO stage 3 | Alive with disease | YWHAE-FAM22B |
| 11 | 66 | Metastatic tumor (vagina) | High grade ESS | FIGO stage 3B | Alive with disease | YWHAE-FAM22B |
| 12 | 50 | Primary uterine tumor | High grade ESS | FIGO stage 3C | Alive with disease | YWHAE-FAM22B |

TABLE 4

Filtered 3' sequencing gene expression dataset of 3 YWHAE-FAM22A/B ESS (2 YWHAE-FAM22A and 1 YWHAE-FAM22B), 4 JAZF1-rearranged ESS and 4 uterine leiomyosarcomas (LMS); Genes marked $ and # are shown to be significantly upregulated and downregulated in YWHAE-FAM22A/B ESS compared to JAZF1-rearranged ESS respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | | | | | Sample code | | | | | | |
| | STT5519_ESS | STT5521_ESS | STT5520_ESS | STT5543-ESS | STT5774b_ESS | STT5775b_ESS | STT5776b_ESS | STT5837_LMS | STT5836_LMS | STT5838_LMS | STT5853_LMS |
| SORBS3 | 0.059797 | 0.009878 | 0.018274 | −0.065952 | −0.016628 | −0.026442 | −0.074921 | −0.004124 | 0.021913 | 0.082789 | −0.003926 |
| FAM176B | 0.033249 | −0.023256 | 0.01193 | −0.020513 | 0.050515 | −0.055492 | −0.043038 | 0.035408 | −0.022771 | 0.089738 | −0.052861 |
| NENF | 0.054074 | −0.044114 | 0.025917 | 0.005846 | 0.043546 | −0.075238 | −0.076567 | 0.012926 | −0.011897 | 0.032275 | 0.044347 |
| EFEMP2 | 0.074317 | 0.013268 | 0.051475 | 0.007135 | 0.042017 | −0.044807 | −0.086809 | −0.00053 | −0.020536 | 0.032228 | −0.03381 |
| H19 | −0.055839 | 0.02541 | 0.017175 | −0.045044 | 0.004234 | −0.02173 | −0.020583 | −0.048106 | 0.110246 | 0.028759 | 0.003939 |
| PLXNB2 | −0.077779 | 0.046134 | −0.011402 | −0.070334 | 0.015327 | −0.026809 | 0.015132 | −0.025349 | 0.018752 | 0.079888 | 0.022329 |
| SLC16A3 | −0.003366 | −0.006766 | −0.027092 | 0.004614 | 0.081753 | −0.031272 | −0.038811 | 0.074324 | −0.028365 | 0.034675 | −0.069291 |
| IGFBP6 | −0.033425 | 0.000504 | 0.003471 | 0.027698 | 0.061208 | −0.052393 | −0.064994 | 0.087897 | 0.012947 | −0.003846 | −0.042327 |
| FEV | −0.007776 | −0.040585 | 0.02796 | 0.054097 | 0.099795 | −0.061802 | −0.055832 | | | | 0.000858 |
| SERPING1 | −0.096042 | 0.038448 | 0.017024 | 0.013584 | 0.094589 | −0.037827 | −0.024647 | −0.004868 | −0.00528 | 0.008881 | 0.004456 |
| LRP1 | −0.115917 | 0.013242 | 0.03215 | 0.004714 | 0.063736 | 0.003168 | −0.046153 | 0.03323 | −0.002071 | −0.010507 | 0.014938 |
| PLD3 | −0.100023 | −0.00347 | −0.019902 | −0.023041 | 0.05819 | −0.004599 | −0.058881 | 0.019997 | 0.055877 | 0.020103 | 0.023838 |
| TMSB4X | −0.072788 | −0.022875 | 0.010781 | −0.054802 | 0.025333 | 0.054146 | −0.080711 | 0.030212 | 0.004144 | 0.033359 | 0.035229 |
| TNFRSF1A | −0.024952 | 0.015254 | 0.042736 | −0.000647 | 0.048048 | −0.020955 | −0.11603 | 0.031554 | −0.022929 | 0.041306 | 0.013851 |
| OLFML3 | −0.044779 | −0.005322 | 0.044298 | 0.00991 | 0.064265 | 0.019466 | −0.102038 | 0.004916 | −0.039003 | 0.010053 | 0.040632 |
| CALR | −0.096163 | 0.003893 | −0.032501 | 0.053096 | −0.009932 | −0.013189 | −0.056409 | 0.046221 | 0.005066 | 0.030924 | 0.051006 |
| FADS2 | −0.055537 | 0.019421 | −0.059798 | 0.040268 | 0.055233 | −0.076052 | −0.017312 | 0.004364 | 0.004382 | 0.0644 | 0.018269 |
| CENPB | −0.021679 | −0.063408 | −0.007057 | 0.0329 | 0.023943 | −0.013565 | −0.039215 | −0.022664 | 0.116358 | −0.001033 | −0.018455 |
| SLC44A2 | −0.049916 | −0.076067 | 0.020696 | 0.010913 | 0.034516 | 0.040931 | −0.027354 | −0.059368 | 0.035926 | 0.069635 | −0.014427 |
| LAMB2 | −0.036039 | −0.047236 | 0.044881 | −0.009938 | 0.03664 | −0.018399 | −0.030012 | −0.083109 | 0.043625 | 0.045675 | 0.056491 |
| NFIX | −0.066665 | −0.085265 | −0.006692 | 0.021837 | 0.014674 | −0.031663 | −0.006948 | 0.013051 | 0.055121 | −0.009847 | 0.074194 |
| CD97 | −0.032893 | −0.041872 | −0.014233 | 0.026608 | 0.011955 | −0.050102 | −0.028108 | −0.040984 | 0.053065 | 0.006296 | 0.102899 |
| GPX4 | −0.021626 | −0.038518 | −0.079016 | −0.019349 | 0.01403 | 0.000948 | 0.084671 | −0.023743 | 0.018025 | 0.066708 | −0.032213 |
| SMARCA4 | −0.016639 | 0.009872 | −0.053035 | −0.040387 | −0.030029 | −0.00337 | 0.090064 | −0.046043 | 0.050626 | 0.053348 | −0.030671 |
| FAM40B | −0.057048 | −0.028759 | −0.01105 | −0.004621 | −0.034589 | −0.051513 | 0.084565 | 0.017196 | 0.008798 | −0.018295 | 0.079865 |
| LOC388692 | −0.01246 | −0.049236 | −0.062156 | −0.015845 | −0.081561 | 0.001612 | 0.0669 | 0.021337 | 0.045066 | 0.0445 | 0.004647 |
| INADL | 0.016974 | −0.009705 | −0.038868 | −0.016361 | −0.082972 | −0.062361 | 0.082482 | 0.025338 | 0.031879 | 0.023348 | 0.019282 |
| SENP5 | −0.025934 | −0.018799 | −0.031251 | 0.000365 | −0.06728 | −0.049962 | 0.106789 | 0.021244 | 0.03412 | 0.00114 | 0.016316 |
| RNF168 | −0.031886 | −0.02442 | −0.032561 | 0.001333 | −0.069201 | −0.053214 | 0.095877 | 0.035832 | 0.026268 | 0.006253 | 0.028484 |
| KCNQ1OT1 | −0.035569 | −0.024904 | −0.035461 | −0.020955 | −0.070279 | −0.039187 | 0.095563 | 0.040393 | 0.019899 | 0.016376 | 0.028768 |
| NKX3-1 | −0.047877 | 0.006683 | −0.010597 | −0.002002 | −0.068665 | −0.062286 | 0.094741 | 0.033836 | 0.013288 | 0.00656 | 0.030405 |
| LOC90784 | 0.014049 | −0.021807 | −0.035046 | −0.003824 | −0.073053 | −0.034957 | 0.109765 | −0.010157 | 0.04081 | 0.003408 | 0.003031 |
| FANCD2 | −0.025952 | −0.013649 | −0.037144 | −0.008902 | −0.067062 | −0.023794 | 0.113405 | 0.005192 | 0.045105 | −0.001077 | −0.002626 |
| DSEL | −0.012821 | −0.024597 | −0.043936 | −0.013153 | −0.06349 | −0.033362 | 0.111573 | 0.01707 | 0.03734 | 0.011422 | −0.005563 |
| PAN3 | −0.025747 | −0.010211 | −0.035949 | 0.00627 | −0.0555 | −0.043061 | 0.117554 | 0.004344 | 0.030323 | −0.014673 | 0.017504 |

TABLE 4-continued

Filtered 3' sequencing gene expression dataset of 3 YWHAE-FAM22A/B ESS
(2 YWHAE-FAM22A and 1 YWHAE-FAM22B), 4 JAZF1-rearranged ESS and 4 uterine
leiomyosarcomas (LMS); Genes marked $ and # are shown to be significantly
upregulated and downregulated in YWHAE-FAM22A/B ESS compared to JAZF1-rearranged ESS
respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | Sample code | | | | | | | | | | |
| | STT5519_ESS | STT5521_ESS | STT5520_ESS | STT5543-ESS | STT5774b_ESS | STT5775b_ESS | STT5776b_ESS | STT5837_LMS | STT5836_LMS | STT5838_LMS | STT5853_LMS |
| TMED10P1 | −0.022041 | −0.018328 | −0.043225 | 0.008685 | −0.053579 | −0.034583 | 0.12249 | 0.000032 | 0.020878 | 0.003166 | 0.005507 |
| COL18A1 | 0.011312 | −0.032113 | 0.013863 | 0.016029 | 0.003139 | 0.019581 | 0.054575 | −0.026556 | −0.020393 | 0.073649 | −0.103861 |
| AGRN | −0.007534 | −0.064196 | −0.014585 | 0.027731 | −0.007612 | 0.022008 | −0.007806 | 0.037365 | −0.019268 | 0.094107 | −0.076981 |
| PLXND1 | −0.040151 | −0.030116 | −0.024362 | 0.02416 | −0.011163 | 0.02834 | 0.034757 | 0.003563 | 0.012444 | 0.084488 | −0.095784 |
| THY1 | 0.035182 | −0.028835 | −0.002034 | −0.006274 | −0.063991 | −0.025295 | −0.012615 | 0.042123 | −0.042962 | 0.10783 | −0.007643 |
| FOXS1 | 0.024104 | −0.064503 | −0.005325 | −0.045984 | −0.040829 | −0.008038 | 0.042621 | −0.009121 | 0.010106 | 0.10478 | −0.026748 |
| PGF | 0.033894 | −0.069357 | −0.010648 | −0.010914 | −0.036165 | −0.003138 | 0.025825 | −0.054098 | 0.002221 | 0.105485 | 0.008796 |
| COX4I2 | 0.005325 | −0.061333 | −0.023198 | 0.001645 | −0.071287 | 0.008745 | 0.025847 | −0.004497 | −0.014492 | 0.109047 | 0.005794 |
| ATP5D | 0.021524 | −0.05817 | −0.045972 | 0.032594 | −0.035664 | −0.068121 | 0.020994 | −0.005292 | 0.034984 | 0.087308 | 0.007856 |
| CRIP1 | 0.012317 | −0.035067 | 0.024202 | 0.025094 | −0.104521 | 0.011469 | 0.057318 | 0.013919 | −0.029391 | 0.058897 | −0.029112 |
| PPP1R14A | −0.011437 | 0.040546 | −0.008174 | 0.018046 | −0.077908 | −0.033878 | −0.018167 | −0.055988 | 0.058047 | 0.028301 | 0.07275 |
| APOE | 0.00796 | 0.017037 | 0.116499 | −0.01217 | −0.048142 | −0.053163 | −0.026127 | 0.025269 | 0.035672 | −0.018019 | −0.013277 |
| TNFRSF12A | −0.013217 | 0.040729 | 0.023507 | −0.056819 | −0.045596 | 0.010861 | −0.030686 | 0.088194 | 0.036951 | −0.001766 | −0.066428 |
| MXRA8 | −0.017502 | 0.007546 | 0.031067 | 0.00974 | 0.009263 | −0.037413 | −0.043456 | 0.106046 | 0.028118 | −0.069125 | −0.026468 |
| CREB3L1 | −0.020386 | −0.007099 | 0.038221 | −0.025746 | −0.018011 | −0.072863 | −0.027 | 0.098324 | 0.055565 | −0.023863 | −0.005975 |
| COL1A2 | −0.00309 | −0.052719 | 0.037229 | −0.027419 | −0.016961 | −0.029998 | −0.048051 | 0.09506 | 0.058155 | 0.004756 | −0.038056 |
| COL1A1 | −0.00055 | −0.049258 | 0.065753 | −0.011898 | −0.00873 | −0.035728 | −0.052192 | 0.08821 | 0.047655 | −0.022967 | −0.02764 |
| SRPX2 | 0.050878 | −0.003649 | 0.025543 | −0.022956 | −0.044629 | −0.049248 | −0.04987 | 0.103912 | 0.018444 | −0.015108 | −0.016148 |
| TCIRG1 | 0.040481 | 0.038197 | −0.006229 | −0.016383 | −0.029963 | −0.077162 | −0.034229 | 0.069094 | 0.048349 | 0.028226 | −0.054551 |
| CAPG | 0.002851 | 0.011206 | 0.01251 | 0.016549 | −0.061517 | −0.058081 | −0.015747 | 0.095269 | 0.044258 | 0.010579 | −0.05653 |
| TGFB1 | 0.003953 | −0.004578 | −0.019087 | −0.02361 | −0.06624 | −0.032472 | −0.015549 | 0.080584 | 0.069517 | 0.039028 | −0.053109 |
| CTSD | 0.040317 | −0.00223 | −0.029601 | 0.016242 | −0.03172 | −0.051523 | −0.066664 | 0.083205 | 0.059009 | 0.005628 | −0.031627 |
| SEPN1 | −0.013153 | 0.024349 | 0.012897 | 0.022947 | 0.007019 | −0.048225 | −0.069722 | 0.067045 | 0.055962 | 0.020899 | −0.074525 |
| COL7A1# | 0.035743 | 0.0031 | 0.040289 | 0.050596 | −0.019648 | −0.039844 | −0.03899 | 0.073303 | 0.032677 | −0.050309 | −0.066152 |
| ACAP3 | 0.00094 | 0.061976 | −0.002387 | 0.015675 | −0.08018 | −0.031617 | 0.011559 | 0.035799 | 0.076142 | −0.055458 | −0.022407 |
| DDAH2 | 0.047713 | 0.067199 | −0.070161 | 0.013474 | −0.02211 | 0.003872 | −0.087351 | 0.043346 | −0.015785 | 0.010285 | 0.006939 |
| P4HB | −0.007837 | 0.040766 | −0.053875 | −0.002424 | 0.024914 | −0.015301 | −0.063536 | 0.108457 | −0.008465 | −0.014924 | −0.027048 |
| FKBP2 | −0.002926 | 0.045107 | −0.019178 | −0.049744 | 0.032621 | −0.028751 | −0.101315 | 0.066147 | 0.001787 | 0.025115 | 0.016194 |
| ARF5 | 0.01108 | 0.00956 | −0.062292 | −0.018196 | −0.04209 | 0.004583 | −0.090861 | 0.061287 | 0.053923 | 0.033455 | 0.007442 |
| HNRNPUL2 | 0.000639 | −0.021647 | −0.029308 | −0.012468 | −0.04367 | −0.009243 | −0.092301 | 0.059278 | 0.0612 | 0.055196 | 0.003305 |
| PLOD3 | −0.0213 | 0.030594 | −0.065921 | 0.007522 | −0.037084 | −0.038128 | −0.068305 | 0.077133 | 0.030739 | 0.041336 | 0.020561 |
| EMILIN1 | −0.010523 | 0.00439 | −0.02214 | 0.010677 | −0.021287 | −0.062741 | −0.074439 | 0.085117 | 0.05879 | −0.01134 | 0.028595 |
| RABAC1 | −0.019451 | 0.015281 | −0.029869 | 0.008479 | −0.025506 | −0.033519 | −0.068669 | 0.045526 | 0.108958 | −0.017385 | −0.000415 |
| SRC | −0.028529 | 0.013502 | −0.034919 | −0.000225 | −0.017886 | −0.069782 | −0.062435 | 0.017129 | 0.066342 | 0.072425 | 0.032697 |
| ZYX | −0.002767 | 0.037931 | 0.00933 | −0.055467 | −0.053707 | −0.035978 | −0.067974 | 0.024461 | 0.0627 | 0.005539 | 0.065899 |
| HSPB1 | −0.028153 | 0.027785 | −0.072178 | −0.046169 | 0.004242 | −0.009025 | −0.0652 | 0.013022 | 0.07531 | 0.008722 | 0.056024 |
| ILK | −0.041556 | 0.005801 | −0.027143 | −0.071046 | −0.002648 | −0.022895 | −0.060622 | 0.028182 | 0.073998 | 0.018599 | 0.062813 |
| GOLGA2 | −0.015968 | 0.053878 | −0.048071 | −0.038201 | −0.051613 | 0.012926 | −0.046776 | 0.055397 | 0.06223 | 0.036718 | −0.045561 |
| INPPL1 | −0.021003 | 0.075209 | −0.06697 | −0.01208 | −0.042439 | −0.038505 | −0.046014 | 0.022983 | 0.060299 | 0.042648 | 0.014143 |
| ANKRD13D | 0.015213 | 0.090661 | −0.085861 | −0.011514 | −0.036925 | −0.02763 | −0.039641 | 0.017613 | 0.037027 | 0.031076 | 0.003428 |
| STIP1 | 0.00652 | 0.095834 | −0.083511 | −0.021685 | −0.041528 | −0.000302 | −0.039204 | 0.019242 | 0.029504 | 0.032668 | −0.00848 |
| IFI27 | −0.021783 | 0.076725 | −0.021318 | −0.05663 | −0.04454 | 0.002394 | −0.023084 | −0.000702 | 0.09711 | −0.001531 | −0.018276 |
| OAZ2 | −0.03411 | 0.001839 | −0.072312 | 0.001661 | −0.035996 | 0.04077 | −0.052181 | 0.006978 | 0.034048 | 0.093546 | −0.016558 |
| CLIC1 | −0.047599 | 0.015059 | −0.063013 | −0.000352 | −0.035925 | 0.027289 | −0.063721 | 0.063846 | 0.04252 | 0.055072 | −0.02892 |
| OAZ1 | −0.001077 | 0.017966 | −0.110875 | −0.043504 | 0.019698 | −0.013383 | −0.021011 | 0.023642 | 0.045979 | 0.061742 | −0.017575 |
| DUS1L | −0.001207 | 0.026681 | −0.076456 | −0.070306 | −0.051412 | −0.008686 | −0.006007 | 0.056095 | 0.047206 | 0.051313 | −0.006912 |
| MYO9B | −0.03253 | 0.000484 | −0.080555 | −0.029974 | −0.05389 | −0.010926 | −0.003608 | 0.00739 | 0.089177 | 0.036694 | 0.038422 |
| ATP6V0B | −0.013622 | −0.016659 | −0.079323 | −0.068862 | −0.055328 | −0.003415 | 0.016865 | 0.035629 | 0.044222 | 0.052813 | 0.037998 |
| UBE2S | −0.022675 | −0.034023 | −0.068842 | −0.078286 | −0.047136 | 0.042402 | 0.024117 | 0.01054 | 0.056399 | 0.029703 | 0.03158 |
| MAP7D1 | −0.015088 | −0.032084 | −0.081105 | −0.05164 | −0.023898 | 0.008349 | −0.029684 | 0.032579 | 0.054235 | 0.078865 | 0.008135 |
| TECR | −0.010306 | −0.040594 | −0.086842 | −0.037739 | −0.00355 | −0.029611 | 0.044197 | −0.01206 | 0.064649 | 0.066134 | 0.007153 |
| BAT2 | 0.017405 | −0.034367 | −0.098997 | −0.042117 | −0.024894 | −0.039233 | 0.031533 | 0.019801 | 0.049255 | 0.045196 | 0.035213 |
| SMTN | −0.031101 | 0.00673 | −0.003077 | −0.050266 | −0.050591 | −0.056341 | −0.020067 | 0.008665 | 0.077953 | 0.022861 | 0.077155 |
| EHBP1L1 | −0.014537 | 0.008336 | −0.053425 | −0.045845 | −0.049305 | −0.046929 | −0.008121 | −0.003308 | 0.063494 | 0.043723 | 0.080138 |
| TPM2 | 0.019069 | −0.009891 | −0.044762 | −0.05689 | −0.04768 | −0.049228 | −0.02183 | 0.005019 | 0.068944 | 0.039524 | 0.071292 |
| TGFB1I1 | −0.01077 | −0.010937 | −0.05655 | −0.023251 | −0.028333 | −0.056827 | −0.045286 | 0.028882 | 0.046156 | 0.041979 | 0.086767 |
| DES | −0.01262 | −0.037415 | −0.035042 | −0.054817 | −0.014897 | −0.067835 | −0.00001 | 0.014408 | 0.0856 | 0.041297 | 0.049563 |
| UBE2M | 0.018013 | −0.014597 | −0.0431 | −0.099229 | −0.02696 | −0.002684 | 0.017162 | −0.023253 | 0.055879 | 0.010564 | 0.072578 |
| ACTG2 | −0.011338 | −0.082539 | −0.076714 | | −0.018972 | −0.014451 | 0.014206 | −0.005889 | 0.059075 | 0.028126 | 0.066333 |
| TAGLN | 0.02198 | −0.049739 | −0.047005 | −0.084739 | −0.019553 | −0.036552 | 0.020983 | 0.013176 | 0.047631 | 0.024433 | 0.069044 |
| JPH2 | 0.009092 | −0.055863 | −0.041022 | −0.057461 | −0.008114 | −0.033225 | −0.011901 | −0.019994 | 0.079378 | 0.033809 | 0.070495 |
| ACTB | −0.036755 | −0.019926 | −0.053364 | −0.082022 | 0.015724 | −0.03979 | 0.008904 | 0.028003 | 0.048052 | 0.009568 | 0.076776 |
| CNN1 | 0.000282 | 0.002222 | −0.020208 | −0.068057 | 0.002252 | −0.054403 | 0.00153 | −0.043107 | 0.059156 | 0.012617 | 0.093719 |
| MYL9 | 0.045208 | −0.04253 | −0.034785 | −0.053179 | −0.033284 | −0.057786 | −0.015614 | 0.004586 | 0.062687 | 0.031093 | 0.069379 |

TABLE 4-continued

Filtered 3' sequencing gene expression dataset of 3 YWHAE-FAM22A/B ESS
(2 YWHAE-FAM22A and 1 YWHAE-FAM22B), 4 JAZF1-rearranged ESS and 4 uterine
leiomyosarcomas (LMS); Genes marked $ and # are shown to be significantly
upregulated and downregulated in YWHAE-FAM22A/B ESS compared to JAZF1-rearranged ESS
respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | | | | | Sample code | | | | | | |
| | STT5519_ESS | STT5521_ESS | STT5520_ESS | STT5543-ESS | STT5774b_ESS | STT5775b_ESS | STT5776b_ESS | STT5837_LMS | STT5836_LMS | STT5838_LMS | STT5853_LMS |
| RAB5B | 0.073022 | −0.04561 | −0.053222 | −0.045552 | −0.035001 | −0.048972 | −0.01687 | 0.024642 | 0.040068 | 0.024152 | 0.057346 |
| POLH | 0.03723 | −0.035859 | −0.068613 | −0.015304 | −0.084016 | −0.023596 | 0.019943 | 0.011787 | 0.067332 | 0.03566 | 0.027223 |
| LOC100131257 | 0.047143 | −0.051411 | −0.051016 | 0.01279 | −0.083205 | −0.032948 | −0.009438 | 0.025015 | 0.036732 | 0.0217 | 0.064319 |
| TPTE2P2 | 0.03565 | −0.053543 | −0.061031 | −0.008301 | −0.077874 | −0.02919 | −0.006285 | 0.035666 | 0.049489 | 0.032213 | 0.051635 |
| VWA3A | 0.053442 | −0.02758 | −0.042213 | −0.019506 | −0.064595 | −0.078985 | 0.015965 | 0.034481 | 0.036602 | 0.029166 | 0.049878 |
| CKM | 0.049956 | −0.0472 | −0.051087 | −0.029799 | −0.053158 | −0.056843 | −0.011969 | 0.055155 | 0.041809 | 0.049388 | 0.025722 |
| NDUFS8 | 0.071907 | −0.014733 | −0.085389 | −0.00903 | −0.043625 | −0.034215 | −0.032259 | 0.034029 | 0.055709 | 0.034287 | 0.000658 |
| CARM1 | 0.06251 | −0.005934 | −0.031975 | −0.039974 | −0.011743 | −0.069839 | 0.003849 | −0.016708 | 0.094537 | −0.022286 | 0.03172 |
| PTRF | 0.068747 | −0.047573 | −0.019415 | −0.072406 | −0.025043 | −0.035028 | 0.008024 | 0.010542 | 0.070335 | −0.027154 | 0.044604 |
| SELM | 0.045825 | 0.023145 | −0.018369 | −0.026552 | 0.018006 | −0.107376 | −0.038276 | 0.010143 | 0.056025 | −0.0016 | 0.045511 |
| HSPB7 | 0.038715 | −0.01597 | −0.076854 | −0.024481 | 0.017618 | −0.071447 | −0.013289 | −0.008033 | 0.068451 | 0.004771 | 0.06073 |
| C1QA | 0.027867 | −0.009106 | −0.042234 | −0.048826 | −0.011571 | −0.056752 | −0.052403 | 0.03184 | 0.069425 | 0.073039 | −0.004225 |
| EHD2 | 0.050461 | −0.037345 | −0.004609 | −0.071249 | −0.00558 | −0.066467 | −0.031757 | 0.028441 | 0.075348 | 0.006645 | 0.03586 |
| CDC42EP1 | 0.037986 | −0.038367 | 0.029019 | −0.062776 | −0.017698 | −0.066136 | −0.040458 | 0.015083 | 0.074027 | 0.049868 | 0.009796 |
| PDK3 | −0.02938 | −0.012759 | −0.040263 | 0.001725 | −0.086782 | −0.047882 | 0.011191 | 0.056435 | 0.068209 | 0.041058 | 0.013788 |
| KILLIN | −0.001368 | 0.037184 | −0.018825 | −0.023218 | −0.091312 | −0.069872 | 0.018115 | 0.066689 | 0.030639 | 0.02838 | 0.017165 |
| PDLIM5 | 0.004142 | −0.041464 | −0.027314 | −0.050567 | −0.074867 | −0.040075 | 0.019814 | 0.033758 | 0.080974 | 0.0294 | 0.033294 |
| LOC220906 | 0.008516 | −0.030737 | −0.040484 | −0.020704 | −0.075353 | −0.027995 | 0.055824 | 0.015319 | 0.084203 | 0.038038 | −0.029626 |
| VPS53 | 0.019727 | −0.022765 | −0.061814 | −0.016152 | −0.077315 | −0.03512 | 0.03613 | 0.024851 | 0.086561 | 0.025705 | −0.005969 |
| CYP20A1 | 0.031075 | −0.022273 | −0.050154 | −0.024711 | −0.085644 | −0.023974 | 0.037586 | 0.01647 | 0.081494 | 0.034485 | −0.017331 |
| LOC728264 | 0.019506 | −0.01658 | −0.040037 | −0.038179 | −0.054925 | −0.055633 | 0.017963 | −0.003163 | 0.092344 | 0.060204 | −0.000167 |
| PGPEP1 | 0.019668 | −0.002645 | 0.011091 | −0.018452 | −0.075644 | −0.052986 | −0.000902 | −0.003208 | 0.105083 | 0.038364 | −0.020001 |
| CCBE1 | −0.002417 | −0.012672 | −0.012807 | −0.025962 | −0.073753 | −0.018541 | 0.014207 | 0.02453 | 0.091952 | 0.054757 | −0.057162 |
| MAP2K2 | 0.032207 | 0.03955 | −0.064401 | −0.031648 | −0.051971 | −0.053757 | 0.048237 | −0.03155 | 0.03785 | 0.064321 | 0.00889 |
| SELO | 0.01761 | 0.067439 | −0.03322 | −0.043803 | −0.051404 | −0.060889 | 0.033587 | −0.025993 | 0.067947 | 0.04029 | −0.006219 |
| DAPK3 | 0.025133 | 0.020703 | −0.013765 | −0.067703 | −0.055069 | −0.072679 | −0.00264 | 0.003543 | 0.063862 | 0.048355 | 0.041567 |
| NDUFV1 | 0.066694 | 0.006248 | −0.013065 | −0.050565 | −0.068097 | −0.056277 | 0.000953 | −0.018021 | 0.061292 | 0.054274 | 0.016289 |
| ZNF358 | 0.052209 | 0.012936 | −0.017924 | −0.017565 | −0.014356 | −0.069224 | −0.008495 | −0.064191 | 0.089238 | 0.03916 | 0.010094 |
| UBQLN4 | 0.089555 | 0.017245 | −0.076522 | −0.058914 | −0.004071 | −0.024021 | −0.004469 | −0.017811 | 0.047098 | −0.017914 | 0.03462 |
| ATP6V0D1 | 0.064547 | 0.020408 | −0.093963 | −0.039152 | −0.031498 | 0.011002 | −0.001961 | 0.015039 | 0.016238 | −0.046607 | 0.059905 |
| KCTD13 | 0.121597 | −0.004512 | −0.037559 | −0.024781 | −0.05055 | −0.019621 | −0.027925 | −0.002691 | 0.034395 | −0.010581 | 0.021425 |
| ATP6AP1 | 0.129532 | −0.03464 | −0.017295 | −0.016065 | −0.031704 | −0.035536 | −0.032711 | 0.013084 | 0.009846 | 0.009931 | 0.008489 |
| ATP6V0C | 0.091949 | −0.070325 | −0.042771 | −0.006254 | −0.05105 | −0.017807 | 0.032067 | 0.028159 | 0.023895 | −0.032295 | 0.026181 |
| NDUFB10 | 0.081475 | −0.061826 | −0.070605 | −0.022882 | −0.020324 | 0.008416 | −0.007354 | 0.002628 | 0.052766 | −0.035473 | 0.041901 |
| CFL1 | 0.043681 | −0.035872 | −0.100005 | −0.033004 | 0.013546 | −0.02343 | −0.021577 | 0.019056 | 0.010281 | 0.010578 | 0.079048 |
| FKBP8 | −0.066463 | −0.057495 | −0.067013 | 0.006896 | −0.030761 | −0.009213 | 0.010725 | 0.035846 | 0.074157 | 0.044227 | 0.012836 |
| BGN | 0.024109 | −0.071914 | −0.015825 | −0.035829 | −0.0294 | −0.035763 | 0.027927 | 0.050987 | 0.049521 | 0.064071 | −0.054587 |
| MMP9 | −0.020196 | −0.041279 | −0.053242 | −0.039306 | −0.011605 | −0.026716 | −0.002024 | 0.088116 | 0.011669 | 0.079478 | −0.027405 |
| COL5A3 | −0.031788 | −0.074095 | −0.002051 | −0.005817 | −0.002742 | −0.020913 | −0.002438 | 0.056758 | 0.016406 | 0.094326 | −0.054175 |
| CSPG4 | −0.013001 | −0.077861 | −0.018568 | −0.022911 | −0.039035 | −0.026343 | 0.007484 | 0.024038 | 0.04079 | 0.103051 | −0.008739 |
| HLA-E | −0.022565 | −0.063571 | −0.028781 | −0.053026 | −0.00332 | −0.005018 | 0.007077 | 0.030318 | 0.042952 | 0.097556 | −0.041886 |
| NDUFA4L2 | −0.048661 | −0.039729 | −0.019807 | −0.022639 | −0.041276 | −0.008399 | 0.019505 | 0.038664 | 0.000058 | 0.115407 | −0.022198 |
| TAGLN2 | −0.012799 | −0.029104 | −0.042057 | −0.025709 | −0.039083 | −0.001985 | −0.037224 | 0.051827 | 0.071025 | 0.077101 | −0.047745 |
| COL6A2 | −0.01639 | −0.070688 | −0.01671 | −0.001785 | −0.030013 | −0.012156 | −0.035767 | 0.084238 | 0.054717 | 0.050976 | −0.041812 |
| ADAMTS14 | −0.037775 | −0.040764 | 0.013578 | 0.019428 | −0.057442 | −0.005362 | −0.010976 | 0.083169 | 0.04647 | 0.038929 | −0.067978 |
| SPOCD1 | −0.044388 | −0.073617 | | | −0.042176 | | −0.014591 | 0.074328 | 0.08345 | −0.021029 | |
| AEBP1 | −0.010792 | −0.015061 | −0.005414 | −0.092081 | −0.00016 | −0.054408 | 0.00382 | 0.067828 | 0.072048 | 0.019533 | −0.017686 |
| RCN3 | −0.022376 | 0.005417 | −0.00298 | −0.092105 | 0.007117 | −0.03197 | −0.010897 | 0.073631 | 0.050394 | 0.042031 | −0.048693 |
| LAPTM5 | 0.002226 | −0.027366 | −0.024914 | −0.081718 | −0.008057 | −0.02118 | −0.024436 | 0.07505 | 0.038634 | 0.068693 | −0.036134 |
| LMNA | −0.019008 | −0.048611 | −0.057604 | −0.037401 | −0.024593 | −0.006691 | −0.046272 | 0.070111 | 0.079271 | 0.027051 | 0.012211 |
| EMP3 | −0.037667 | −0.036466 | −0.055476 | −0.056946 | 0.004379 | −0.021457 | −0.035295 | 0.068855 | 0.07671 | 0.025706 | 0.015231 |
| ISG15 | 0.040184 | −0.000886 | −0.045023 | −0.013378 | −0.046076 | 0.004469 | −0.003682 | 0.023697 | 0.089088 | 0.021209 | −0.085944 |
| H2AFJ | 0.05357 | −0.017954 | 0.002111 | −0.016142 | −0.060534 | −0.0813 | −0.036493 | 0.068092 | 0.026047 | 0.038931 | 0.020466 |
| AFMID# | 0.064646 | −0.015807 | 0.003104 | 0.032999 | −0.057733 | −0.072172 | −0.065185 | 0.032039 | 0.018821 | 0.039555 | 0.032382 |
| LRRN4 | 0.05274 | −0.014181 | −0.000355 | 0.047314 | −0.054286 | −0.066232 | −0.050819 | 0.073934 | −0.012768 | 0.039152 | −0.003566 |
| FASTKD2 | 0.007454 | −0.014142 | −0.013725 | 0.040757 | | −0.059579 | −0.071246 | 0.072562 | −0.026472 | 0.074341 | −0.009434 |
| CACNA1A | −0.01151 | 0.041553 | −0.018574 | 0.023656 | −0.051353 | −0.068566 | −0.056757 | 0.058643 | −0.002789 | 0.072183 | 0.018214 |
| GPM6A | −0.021305 | −0.004272 | −0.004913 | 0.016498 | −0.057811 | −0.072356 | −0.037738 | 0.069263 | −0.001981 | 0.068318 | 0.01942 |
| C3orf14 | −0.016779 | −0.003706 | −0.024182 | 0.016362 | −0.062357 | −0.079492 | −0.019801 | 0.06059 | 0.010895 | 0.073788 | 0.036478 |
| PPAPDC2# | −0.00193 | 0.02203 | 0.014306 | 0.028436 | −0.071638 | −0.075651 | −0.057939 | 0.056554 | 0.020948 | 0.045813 | 0.02936 |
| C15orf43# | 0.025162 | 0.013516 | 0.00852 | 0.00847 | −0.066548 | −0.078711 | −0.063649 | 0.052207 | 0.032986 | 0.043663 | 0.030934 |
| CYBA | 0.040356 | 0.018431 | −0.011245 | −0.021374 | −0.065239 | −0.069087 | −0.027799 | 0.041654 | 0.02404 | 0.086234 | −0.01447 |
| CNN2 | 0.008112 | 0.007959 | 0.046487 | −0.005186 | −0.074784 | −0.085552 | −0.025361 | 0.017281 | 0.025554 | 0.063263 | 0.038552 |

TABLE 4-continued

Filtered 3' sequencing gene expression dataset of 3 YWHAE-FAM22A/B ESS
(2 YWHAE-FAM22A and 1 YWHAE-FAM22B), 4 JAZF1-rearranged ESS and 4 uterine
leiomyosarcomas (LMS); Genes marked $ and # are shown to be significantly
upregulated and downregulated in YWHAE-FAM22A/B ESS compared to JAZF1-rearranged ESS
respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | | | | | Sample code | | | | | | |
| | STT5519_ESS | STT5521_ESS | STT5520_ESS | STT5543-ESS | STT5774b_ESS | STT5775b_ESS | STT5776b_ESS | STT5837_LMS | STT5836_LMS | STT5838_LMS | STT5853_LMS |
| C14orf4 | −0.038153 | −0.030788 | −0.00609 | 0.016077 | −0.021597 | −0.033401 | −0.087472 | 0.066225 | 0.010342 | 0.066133 | 0.038904 |
| PAQR8 | −0.040889 | −0.033509 | −0.003407 | 0.031719 | −0.037434 | −0.046435 | −0.071122 | 0.059427 | 0.016759 | 0.058274 | 0.051728 |
| MAVS | −0.039328 | −0.043903 | −0.042383 | −0.006452 | −0.038723 | −0.036917 | −0.035742 | 0.078633 | 0.020158 | 0.069904 | 0.037206 |
| TMEM19 | −0.031429 | −0.052059 | −0.027324 | 0.01745 | −0.043755 | −0.040997 | −0.052175 | 0.069145 | 0.032948 | 0.06095 | 0.042789 |
| PPM1N | −0.030279 | −0.024037 | −0.018718 | 0.030877 | −0.053835 | −0.066875 | −0.037816 | 0.061119 | 0.059677 | 0.006385 | 0.058102 |
| LSP1 | −0.056907 | −0.034391 | −0.032368 | 0.003296 | −0.0381 | −0.050306 | −0.023657 | 0.088394 | 0.037702 | 0.021173 | 0.051064 |
| SHROOM1 | −0.058875 | −0.038653 | −0.000187 | 0.066022 | −0.035051 | −0.055063 | −0.036716 | 0.030582 | 0.030941 | 0.019762 | 0.071424 |
| PIAS4 | −0.049085 | −0.058809 | −0.00818 | 0.038317 | −0.023721 | −0.056601 | −0.038048 | 0.033229 | 0.023693 | 0.045371 | 0.077275 |
| C10orf57 | −0.017557 | −0.04193 | −0.039044 | 0.017272 | −0.043753 | −0.074369 | −0.019494 | 0.057816 | 0.0245 | 0.060552 | 0.054668 |
| ZNF23 | −0.019707 | −0.047241 | −0.039967 | −0.01502 | −0.047083 | −0.071379 | 0.009852 | 0.059507 | 0.032978 | 0.056498 | 0.05138 |
| GPR85 | −0.021429 | −0.031074 | −0.045769 | 0.04329 | −0.049313 | −0.081114 | 0.010445 | 0.034751 | 0.019474 | 0.044998 | 0.064705 |
| PLA2G2D | −0.022332 | −0.029189 | −0.052854 | −0.012072 | −0.075907 | −0.044783 | 0.035836 | 0.027995 | 0.027235 | 0.042315 | 0.075199 |
| NUBPL | −0.016792 | −0.028576 | 0.02022 | 0.067766 | −0.07616 | −0.043675 | −0.020862 | 0.003882 | 0.024089 | −0.0064 | 0.086216 |
| C1orf69 | −0.015804 | −0.033378 | −0.016596 | 0.06405 | −0.07003 | −0.055035 | −0.010583 | 0.010909 | 0.039082 | 0.003071 | 0.082884 |
| PTPN14 | 0.015777 | −0.049357 | −0.012225 | 0.044635 | −0.091195 | −0.01345 | −0.031649 | 0.028548 | 0.019024 | −0.00304 | 0.082465 |
| SLC4A1 | 0.002913 | −0.009932 | 0.010989 | 0.062478 | −0.056711 | −0.055473 | −0.06844 | 0.028852 | 0.001729 | 0.017281 | 0.077907 |
| PRKCSH | −0.062073 | −0.045291 | 0.011418 | 0.046751 | 0.002572 | −0.080424 | −0.004167 | 0.036143 | 0.021017 | 0.07638 | −0.004248 |
| CERCAM | −0.040032 | 0.006234 | 0.031008 | 0.039566 | −0.061133 | −0.055347 | −0.034034 | 0.074875 | 0.024652 | 0.053578 | −0.033175 |
| FXYD5 | −0.041613 | 0.021635 | 0.054891 | 0.035674 | −0.053841 | −0.054258 | −0.028148 | 0.071627 | 0.012516 | 0.043086 | −0.045259 |
| CD248 | 0.001771 | 0.006373 | 0.029663 | 0.04942 | −0.014174 | −0.050355 | −0.061649 | 0.039502 | −0.0136 | 0.088042 | −0.053966 |
| PITX1 | −0.056436 | 0.005438 | −0.055993 | 0.048554 | −0.030708 | 0.042447 | 0.046493 | −0.033801 | 0.014694 | −0.057499 | 0.063515 |
| PTK7 | −0.019312 | 0.053041 | −0.064029 | 0.032325 | −0.033619 | 0.045677 | −0.062405 | 0.02714 | 0.020974 | −0.060254 | 0.045425 |
| CRABP2 | 0.006334 | 0.002766 | −0.029211 | 0.046143 | −0.013048 | 0.040453 | −0.085078 | 0.000863 | −0.008466 | −0.052642 | 0.085986 |
| NES | 0.055172 | −0.03304 | −0.025564 | 0.02333 | −0.000431 | 0.021284 | −0.079758 | −0.067085 | 0.000949 | 0.051836 | 0.054554 |
| IGFBP5 | 0.049495 | −0.006376 | −0.110679 | 0.075644 | 0.000646 | 0.001404 | −0.000179 | −0.012499 | −0.02568 | −0.007401 | 0.031261 |
| PPP2R4 | −0.027733 | −0.061253 | −0.087813 | 0.06182 | 0.043959 | 0.02945 | −0.028063 | −0.014893 | 0.005018 | 0.049185 | 0.002283 |
| EPHB4 | −0.03882 | −0.02126 | −0.089854 | 0.025763 | 0.018591 | 0.020777 | −0.043355 | −0.01798 | 0.010852 | 0.011525 | 0.09157 |
| TRIOBP | 0.032471 | −0.001987 | 0.061052 | −0.000476 | 0.016199 | −0.061102 | −0.031404 | −0.021033 | −0.000151 | −0.059765 | 0.092358 |
| HTRA3 | −0.042608 | −0.019144 | 0.005174 | −0.008611 | −0.005252 | −0.048035 | 0.007813 | 0.053248 | −0.031832 | −0.035981 | 0.11176 |
| HMGA1 | −0.003996 | −0.032521 | −0.010897 | 0.00222 | 0.030244 | 0.030069 | 0.088635 | 0.04648 | −0.052563 | −0.035852 | −0.072345 |
| SPHK1 | −0.005127 | −0.033039 | 0.000594 | −0.010218 | −0.011469 | 0.044242 | 0.047793 | 0.064672 | 0.018304 | −0.029125 | −0.106541 |
| SH3BGRL3 | 0.003461 | −0.059289 | −0.057422 | 0.024009 | −0.018932 | 0.004944 | 0.018613 | 0.094833 | 0.025068 | −0.001634 | −0.067512 |
| SNX17 | 0.084863 | −0.037263 | −0.040309 | 0.00695 | 0.044935 | 0.005449 | −0.01847 | 0.064379 | −0.028916 | −0.060595 | −0.031726 |
| COL5A1 | 0.093095 | −0.010355 | −0.022575 | 0.01719 | 0.001129 | −0.028678 | −0.026854 | 0.067341 | 0.020878 | −0.039092 | −0.06848 |
| LGALS3BP | 0.066832 | −0.039581 | −0.012456 | 0.075906 | −0.008489 | 0.009964 | −0.011619 | 0.051146 | −0.019285 | −0.021375 | −0.08131 |
| KAT2A | 0.042153 | 0.065113 | −0.027306 | −0.073878 | 0.019754 | 0.035071 | −0.043936 | −0.04149 | 0.042159 | 0.026702 | −0.048269 |
| GSTP1 | 0.078373 | 0.020601 | −0.047605 | −0.056568 | 0.044147 | 0.050305 | −0.041367 | −0.012648 | 0.010187 | −0.061813 | 0.002057 |
| WFS1 | 0.095447 | 0.071108 | 0.016805 | −0.036149 | 0.021226 | −0.00914 | −0.022811 | −0.042186 | −0.021757 | −0.055039 | 0.014825 |
| LGALS1 | 0.07511 | 0.056662 | 0.013992 | −0.027241 | 0.02392 | −0.021842 | −0.064256 | 0.02517 | 0.014949 | −0.080533 | 0.001346 |
| MFAP4 | 0.089759 | 0.043849 | 0.010267 | 0.017181 | −0.001888 | 0.036643 | −0.083251 | −0.033221 | −0.004919 | −0.050234 | 0.001992 |
| CLIP3 | 0.026578 | 0.049827 | 0.052048 | −0.05773 | 0.039048 | 0.029565 | −0.037514 | −0.085909 | 0.018619 | −0.033794 | 0.020153 |
| FCGRT | 0.029503 | 0.033488 | 0.087813 | −0.040906 | 0.061706 | −0.002441 | −0.065352 | −0.023463 | −0.020812 | −0.041832 | 0.010866 |
| RNS-8S1 | 0.06891 | 0.000841 | −0.035532 | −0.038087 | 0.080127 | −0.005135 | −0.004674 | −0.047166 | −0.017313 | −0.055032 | 0.053183 |
| GRINA | 0.051917 | 0.001206 | 0.02968 | −0.029386 | 0.002505 | 0.060714 | −0.058342 | −0.038669 | −0.081582 | 0.042627 | 0.028407 |
| NFATC4 | 0.013267 | −0.04094 | 0.039599 | −0.032066 | −0.003891 | 0.086785 | −0.085478 | −0.01064 | 0.006956 | 0.04321 | −0.031335 |
| CLTA | 0.031155 | −0.056525 | −0.02126 | −0.062153 | 0.041195 | 0.078825 | −0.064489 | −0.009008 | 0.00751 | −0.018482 | 0.035824 |
| CLEC11A | 0.051865 | −0.02857 | 0.061307 | −0.041066 | 0.07035 | 0.051123 | −0.030037 | −0.009186 | −0.035633 | −0.033101 | −0.049462 |
| VWF | 0.108897 | −0.024999 | 0.048738 | −0.010415 | −0.016499 | 0.017259 | 0.008287 | −0.069874 | −0.005637 | −0.040542 | 0.012183 |
| DPP6 | 0.089362 | −0.081233 | 0.036583 | 0.036162 | 0.025756 | 0.010694 | −0.021354 | −0.006062 | −0.047681 | −0.037855 | 0.010255 |
| FAM50A | 0.076495 | 0.061743 | −0.03559 | −0.040981 | −0.058785 | 0.011833 | 0.011634 | 0.012511 | 0.027232 | 0.007413 | −0.070842 |
| GMPPA | 0.058171 | 0.097579 | −0.037583 | −0.018912 | −0.013729 | −0.004895 | −0.006633 | 0.020413 | 0.012968 | −0.011285 | −0.08175 |
| PTBP1 | 0.099278 | 0.046426 | −0.043869 | −0.048318 | 0.005758 | −0.002759 | 0.034579 | −0.062307 | −0.027095 | −0.00227 | 0.013564 |
| PHPT1 | 0.046537 | 0.0 0192 | −0.094074 | −0.041064 | −0.018825 | 0.022702 | 0.036281 | −0.043939 | −0.016944 | 0.07095 | 0.008305 |
| SOX4 | 0.078473 | 0.012879 | −0.056332 | 0.009347 | −0.071828 | −0.003441 | 0.014124 | −0.041975 | 0.05417 | 0.040496 | −0.031954 |
| BOP1 | 0.092566 | 0.009934 | −0.08307 | −0.01528 | −0.059899 | −0.01222 | 0.044118 | −0.010885 | 0.005365 | 0.025877 | −0.003252 |
| MBD3 | 0.057751 | 0.021609 | −0.093019 | −0.024549 | −0.01835 | −0.025043 | 0.033418 | −0.027034 | 0.048194 | 0.052612 | −0.036784 |
| SSR4 | 0.116653 | 0.013962 | −0.05294 | −0.020422 | −0.020742 | 0.01218 | 0.021163 | 0.007781 | −0.049201 | 0.014605 | −0.039608 |
| LEPREL4 | 0.109761 | −0.034521 | −0.064729 | −0.030521 | −0.007744 | 0.007843 | 0.011412 | 0.022566 | 0.0161 | 0.005617 | −0.053853 |
| KRT8 | 0.108755 | 0.03639 | −0.019527 | 0.01423 | −0.057146 | 0.01017 | −0.016076 | −0.038669 | 0.04193 | −0.027711 | −0.030421 |
| HBA2 | 0.12565 | 0.028501 | −0.016526 | 0.016206 | −0.057809 | −0.016035 | −0.01944 | −0.029603 | −0.011906 | 0.012873 | −0.003958 |
| HBA1 | 0.112095 | 0.015887 | −0.003883 | 0.043328 | −0.053636 | 0.030117 | −0.005791 | −0.040668 | −0.027883 | −0.001733 | −0.036751 |
| C4orf48 | 0.050314 | 0.004294 | −0.043962 | 0.009193 | −0.014571 | 0.030787 | 0.090627 | −0.029177 | −0.052734 | 0.025716 | −0.063861 |
| RNF187 | 0.052957 | −0.020389 | −0.036833 | 0.021261 | 0.044408 | 0.021605 | 0.05137 | −0.032314 | −0.105054 | 0.000262 | 0.01119 |
| TIMM13 | 0.099462 | −0.016634 | −0.043377 | 0.016585 | −0.008372 | −0.022765 | 0.030999 | −0.047482 | −0.061373 | 0.026666 | 0.041288 |

TABLE 4-continued

Filtered 3' sequencing gene expression dataset of 3 YWHAE-FAM22A/B ESS
(2 YWHAE-FAM22A and 1 YWHAE-FAM22B), 4 JAZF1-rearranged ESS and 4 uterine
leiomyosarcomas (LMS); Genes marked $ and # are shown to be significantly
upregulated and downregulated in YWHAE-FAM22A/B ESS compared to JAZF1-rearranged ESS
respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | | | | | Sample code | | | | | | |
| | STT5519_ESS | STT5521_ESS | STT5520_ESS | STT5543-ESS | STT5774b_ESS | STT5775b_ESS | STT5776b_ESS | STT5837_LMS | STT5836_LMS | STT5838_LMS | STT5853_LMS |
| GPAA1 | 0.099388 | −0.004971 | −0.005412 | 0.055181 | 0.002602 | 0.018272 | 0.020473 | −0.067864 | −0.06102 | −0.007908 | −0.01357 |
| COL4A2 | 0.033891 | −0.084062 | −0.021622 | −0.04982 | 0.011832 | 0.024716 | 0.021395 | −0.070799 | 0.034873 | 0.014035 | 0.059275 |
| CAPNS1 | 0.024731 | −0.073482 | −0.013074 | −0.109416 | −0.00483 | 0.051382 | 0.022132 | 0.022947 | 0.020424 | 0.002538 | 0.007413 |
| NDUFA3 | 0.022953 | −0.051092 | −0.025295 | −0.100277 | 0.016821 | 0.070968 | 0.036216 | −0.033103 | −0.010561 | 0.01319 | 0.021623 |
| SOX12 | 0.039237 | −0.035554 | −0.071822 | −0.084439 | −0.002272 | 0.044965 | 0.046171 | −0.033108 | 0.024891 | −0.005465 | 0.036277 |
| PXDN | 0.055742 | −0.054427 | −0.064461 | −0.07018 | 0.001541 | 0.043748 | 0.049538 | 0.006314 | 0.023375 | 0.01375 | −0.044909 |
| NDUFS6 | 0.078196 | −0.0583 | −0.085106 | −0.05082 | 0.006793 | 0.025816 | 0.030743 | −0.025662 | 0.012631 | 0.014717 | 0.016758 |
| NDUFA13 | 0.068512 | −0.077239 | −0.054317 | −0.027073 | −0.008731 | 0.050243 | 0.02796 | −0.052734 | 0.04066 | 0.011041 | −0.005563 |
| NDUFB7 | 0.047843 | −0.049855 | −0.067453 | −0.078353 | 0.004045 | −0.002391 | 0.026631 | −0.029315 | 0.047644 | 0.053521 | 0.011129 |
| PFDN5 | 0.06054 | −0.084885 | −0.002056 | −0.031126 | 0.068301 | 0.045871 | 0.031713 | −0.030604 | −0.030643 | −0.020657 | −0.019792 |
| MYL6B | 0.011618 | −0.052093 | −0.030343 | −0.048316 | 0.002747 | 0.074794 | 0.090954 | −0.030183 | −0.035097 | 0.002368 | −0.013632 |
| HOXD9 | 0.043893 | −0.056688 | −0.019474 | −0.045277 | 0.024864 | 0.07654 | 0.056293 | −0.066834 | −0.000004 | −0.02383 | −0.007934 |
| PABPN1 | −0.037588 | −0.07734 | −0.022393 | −0.038561 | −0.028389 | 0.07467 | 0.036421 | 0.026452 | 0.04213 | 0.023013 | −0.047089 |
| EMX2OS | −0.001889 | −0.027209 | −0.066877 | −0.035046 | −0.059883 | 0.090867 | 0.02461 | 0.012172 | 0.046114 | 0.005247 | −0.033421 |
| CDC37 | 0.015981 | −0.063723 | −0.039139 | −0.053305 | −0.011243 | 0.102453 | 0.012713 | −0.032251 | 0.018447 | 0.031135 | −0.022104 |
| ERGIC3 | 0.004476 | −0.080202 | −0.005951 | −0.03842 | 0.041113 | 0.093333 | 0.006186 | 0.01134 | 0.005492 | −0.013867 | −0.059649 |
| NUCKS1 | −0.000505 | −0.060033 | 0.017573 | −0.062046 | 0.017882 | 0.060998 | 0.061061 | −0.026778 | −0.007824 | 0.043222 | −0.064298 |
| NDUFS5 | 0.058557 | −0.0209 | −0.078594 | −0.031123 | 0.036038 | 0.069705 | −0.005427 | −0.039954 | −0.050837 | 0.028387 | 0.011292 |
| CRIP2 | 0.069322 | −0.043563 | −0.031062 | −0.014691 | 0.020375 | 0.008478 | 0.005087 | −0.061425 | 0.001074 | 0.089942 | −0.045296 |
| EDF1 | 0.081088 | −0.067571 | −0.045229 | −0.039431 | 0.030803 | 0.008401 | 0.021366 | −0.052441 | −0.021338 | 0.050453 | 0.018552 |
| POLR2L | 0.042244 | −0.026443 | −0.086038 | 0.002587 | −0.00731 | 0.083229 | −0.019698 | 0.037543 | −0.035474 | 0.020544 | −0.044283 |
| NRBP1 | 0.046993 | −0.008195 | −0.077052 | −0.069543 | 0.037799 | 0.047663 | 0.001367 | 0.053143 | −0.002341 | −0.023074 | −0.046894 |
| DYNC1H1 | 0.071374 | −0.005695 | −0.041937 | −0.074709 | 0.025046 | 0.045673 | 0.043205 | 0.016226 | −0.063024 | −0.031829 | −0.004154 |
| CIRBP | 0.053785 | −0.026835 | 0.018776 | −0.047043 | 0.033492 | −0.013356 | 0.076075 | −0.089286 | 0.022397 | −0.023093 | 0.006281 |
| RHOT2 | 0.01037 | 0.049472 | −0.010643 | −0.029959 | −0.02771 | 0.047763 | 0.064382 | 0.01567 | 0.022942 | −0.083765 | −0.061351 |
| DMWD | −0.001264 | 0.006474 | −0.044293 | −0.089669 | −0.032473 | 0.015878 | 0.060256 | −0.010871 | 0.083525 | −0.01261 | −0.008688 |
| CDK10 | 0.01051 | 0.035535 | −0.062564 | −0.061859 | 0.00115 | 0.052851 | 0.075309 | −0.014289 | 0.026418 | −0.033295 | −0.05217 |
| MIF | 0.042633 | 0.015549 | −0.063422 | −0.099843 | 0.003226 | 0.045903 | 0.051107 | −0.008326 | 0.006491 | 0.011849 | −0.035787 |
| PPP1R12C | 0.008009 | 0.063001 | 0.000513 | −0.079601 | −0.023439 | 0.017337 | 0.010024 | −0.064998 | 0.056603 | −0.036174 | 0.047487 |
| AMH | 0.009967 | 0.04726 | 0.009691 | −0.092835 | −0.003749 | 0.011085 | 0.062749 | −0.06621 | 0.049308 | −0.010045 | −0.016634 |
| SNRNP70 | 0.020476 | 0.055505 | 0.014213 | −0.050418 | 0.024775 | 0.062112 | 0.047358 | −0.063814 | −0.010171 | −0.06944 | −0.018874 |
| RAB11FIP3 | 0.020417 | 0.023153 | 0.014803 | −0.03973 | 0.021595 | 0.014033 | 0.082296 | −0.04165 | −0.008697 | −0.099048 | 0.022472 |
| PTOV1 | 0.028338 | 0.041963 | −0.0131 | −0.097633 | 0.016601 | 0.045313 | 0.027867 | −0.040202 | −0.002819 | −0.059744 | 0.041783 |
| RPL28 | 0.049572 | −0.026972 | 0.021548 | −0.095025 | 0.023795 | 0.053657 | 0.053939 | −0.033721 | 0.004898 | −0.036012 | −0.028617 |
| RPS9 | 0.03769 | 0.014788 | 0.006453 | −0.099085 | 0.040535 | 0.080235 | −0.010298 | −0.04513 | −0.007431 | −0.020362 | −0.010971 |
| COMP | −0.051152 | 0.012708 | 0.053744 | −0.025863 | −0.079691 | 0.073084 | 0.030157 | −0.041778 | −0.00987 | 0.039152 | |
| ISLR2 | −0.028037 | 0.000836 | 0.05007 | −0.026045 | −0.031495 | 0.070305 | 0.084523 | −0.02323 | −0.058723 | −0.035664 | 0.001224 |
| RPS26 | −0.00774 | −0.070657 | 0.068893 | 0.01003 | −0.013671 | 0.050984 | 0.014095 | −0.010777 | −0.078447 | −0.014574 | 0.054276 |
| C9orf16 | 0.006893 | −0.118558 | −0.027189 | 0.026392 | 0.003643 | 0.054717 | 0.042003 | −0.01156 | −0.024781 | −0.013084 | 0.032906 |
| PPDPF | −0.018669 | −0.081958 | −0.007497 | 0.063036 | −0.039268 | 0.057014 | 0.055646 | −0.000372 | −0.040052 | −0.029549 | 0.029162 |
| EPHX1 | −0.048022 | 0.025008 | −0.042328 | 0.007873 | 0.033263 | 0.055148 | 0.057959 | 0.01364 | −0.09807 | −0.01471 | −0.000243 |
| ELFN1$ | −0.069822 | −0.014421 | −0.002011 | −0.017988 | 0.046067 | 0.067854 | 0.068908 | 0.021158 | −0.049327 | −0.034526 | −0.036757 |
| FSCN1$ | −0.085028 | −0.006492 | −0.015518 | −0.032294 | 0.040058 | 0.070627 | 0.037402 | 0.051862 | −0.027198 | −0.031142 | −0.036954 |
| MDGA1 | −0.050432 | −0.025187 | 0.015039 | 0.001396 | 0.020606 | 0.07572 | 0.078781 | 0.000959 | −0.023839 | −0.034888 | −0.06896 |
| CHST8$ | −0.039268 | −0.035661 | 0.012645 | −0.000647 | 0.056102 | 0.059063 | 0.065535 | | | −0.05983 | −0.069485 |
| QARS$ | −0.048774 | −0.019753 | −0.000835 | −0.060107 | 0.059892 | 0.08285 | 0.042287 | −0.00764 | −0.036903 | −0.047056 | 0.00748 |
| CEBPA$ | −0.053093 | −0.02801 | 0.003349 | −0.034417 | 0.066534 | 0.07119 | 0.066609 | −0.013577 | −0.041606 | −0.033821 | −0.023073 |
| TMEM132E$ | −0.068297 | −0.062909 | −0.025288 | −0.05679 | 0.03962 | 0.057796 | 0.070111 | | | | |
| MMP15$ | −0.020629 | −0.023335 | 0.012252 | −0.01783 | 0.051878 | 0.068682 | 0.080744 | −0.051328 | −0.05136 | −0.03872 | −0.013209 |
| AP2M1$ | −0.067238 | −0.018474 | 0.011177 | −0.034652 | 0.063051 | 0.079377 | 0.043712 | −0.040676 | 0.010353 | −0.035607 | −0.030134 |
| MDK | 0.016224 | 0.008116 | −0.001568 | 0.002566 | 0.043633 | 0.080574 | 0.02811 | −0.057702 | −0.046113 | −0.084014 | 0.016547 |
| ANKRD19$ | 0.002499 | −0.029404 | 0.007381 | −0.01469 | 0.055032 | 0.074756 | 0.062964 | −0.040149 | −0.034947 | −0.074588 | −0.013896 |
| CKB$ | −0.032179 | −0.017447 | 0.000819 | −0.005388 | 0.032181 | 0.061784 | 0.064087 | 0.003747 | −0.046192 | −0.096494 | 0.02289 |
| NME3$ | −0.012932 | −0.011164 | −0.025351 | −0.016082 | 0.022626 | 0.074683 | 0.070759 | 0.001938 | −0.039036 | −0.091825 | 0.007968 |
| COX5B | −0.039286 | −0.020205 | 0.000016 | −0.022405 | 0.043441 | 0.098402 | 0.023968 | −0.040552 | −0.068241 | 0.031226 | −0.020921 |
| TUBB2C$ | −0.059367 | 0.003366 | −0.060633 | −0.02482 | 0.054477 | 0.093467 | 0.02159 | −0.010199 | −0.035893 | 0.012287 | −0.027768 |
| METRN | −0.048167 | −0.058235 | −0.050741 | 0.018727 | 0.010773 | 0.103778 | 0.029904 | 0.014076 | −0.022653 | −0.001685 | −0.034371 |
| UQCR11 | 0.010812 | −0.030711 | −0.048358 | −0.016397 | 0.030606 | 0.042255 | 0.088844 | −0.073854 | −0.038866 | −0.007677 | 0.031709 |
| ITPKB | 0.01246 | −0.039062 | −0.016008 | −0.037592 | 0.021119 | 0.033242 | 0.063053 | −0.080842 | −0.035373 | −0.005981 | 0.074917 |
| RPS15$ | −0.028088 | −0.040939 | 0.019281 | −0.030995 | 0.066746 | 0.035241 | 0.073871 | −0.077312 | −0.034364 | 0.014242 | −0.000484 |
| GNB2L1 | 0.006644 | −0.070029 | 0.025683 | −0.03253 | 0.052305 | 0.060079 | 0.052052 | −0.039716 | −0.068549 | −0.010322 | 0.014451 |
| EEF2 | 0.035893 | −0.019586 | 0.01714 | −0.050045 | 0.072941 | 0.022838 | 0.03352 | −0.060376 | −0.053487 | −0.04417 | 0.049187 |
| RPL36 | 0.045189 | −0.026776 | 0.022336 | −0.064297 | 0.068935 | −0.001189 | 0.04843 | −0.067196 | −0.044591 | −0.00992 | 0.034921 |
| RPL18 | 0.038156 | −0.020448 | 0.049188 | −0.078734 | 0.03988 | 0.033145 | 0.008577 | −0.055364 | −0.008781 | −0.057146 | 0.051471 |

TABLE 4-continued

Filtered 3' sequencing gene expression dataset of 3 YWHAE-FAM22A/B ESS
(2 YWHAE-FAM22A and 1 YWHAE-FAM22B), 4 JAZF1-rearranged ESS and 4 uterine
leiomyosarcomas (LMS); Genes marked $ and # are shown to be significantly
upregulated and downregulated in YWHAE-FAM22A/B ESS compared to JAZF1-rearranged ESS
respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | | | | | Sample code | | | | | | |
| | STT5519_ESS | STT5521_ESS | STT5520_ESS | STT5543-ESS | STT5774b_ESS | STT5775b_ESS | STT5776b_ESS | STT5837_LMS | STT5836_LMS | STT5838_LMS | STT5853_LMS |
| UBA52 | 0.011001 | −0.06303 | −0.008295 | −0.039576 | 0.050488 | 0.053406 | 0.039683 | −0.057999 | 0.006077 | −0.061692 | 0.048999 |
| COX6B1 | 0.012373 | −0.027317 | −0.009084 | −0.08783 | 0.029689 | 0.071433 | 0.046826 | −0.032278 | −0.021927 | −0.048701 | 0.039309 |
| SEPW1$ | −0.007902 | −0.022676 | −0.038083 | −0.077415 | 0.044643 | 0.058774 | 0.049169 | −0.050868 | −0.009189 | −0.030903 | 0.052919 |
| FBL | 0.011847 | −0.031948 | 0.017039 | −0.062684 | 0.072049 | 0.053692 | 0.021084 | −0.057343 | −0.031378 | −0.046924 | 0.044031 |
| RPLP1 | −0.010941 | −0.042832 | −0.006592 | −0.062216 | 0.076227 | 0.056127 | 0.012107 | −0.037859 | −0.031046 | 0.059382 | |
| MYL6$ | −0.001799 | −0.029208 | −0.010295 | −0.064121 | 0.066408 | 0.055153 | 0.026052 | −0.049898 | −0.022911 | −0.050367 | 0.059636 |
| COX4I1$ | −0.013158 | −0.026221 | 0.000062 | −0.073203 | 0.051986 | 0.07295 | 0.040616 | −0.014331 | −0.060955 | −0.036731 | 0.033899 |
| RPS10$ | 0.002603 | −0.061214 | −0.01396 | −0.058033 | 0.057874 | 0.07227 | 0.035696 | −0.031587 | −0.047711 | −0.022299 | 0.03712 |
| ROMO1$ | 0.000111 | −0.026908 | −0.026995 | −0.063833 | 0.063833 | 0.088708 | 0.026554 | −0.031721 | −0.054508 | −0.011864 | 0.008622 |
| RPL4 | −0.016389 | −0.006778 | 0.056867 | −0.016445 | 0.070445 | 0.040377 | 0.038586 | −0.043267 | −0.071072 | −0.056123 | 0.018403 |
| RPL37A | −0.012661 | −0.006457 | 0.028543 | −0.005708 | 0.067536 | 0.056932 | 0.037115 | −0.058372 | −0.086617 | −0.028396 | 0.019157 |
| RPS8 | −0.038372 | −0.01258 | 0.044361 | −0.006462 | 0.07592 | 0.048341 | 0.018483 | −0.044717 | −0.080468 | −0.027776 | 0.031361 |
| RPL5 | −0.041306 | −0.01442 | 0.049293 | 0.001127 | 0.072507 | 0.040534 | 0.029397 | −0.054852 | −0.072996 | −0.02903 | 0.031982 |
| RPS4X | −0.011388 | −0.017082 | 0.058504 | 0.014481 | 0.066147 | 0.056517 | 0.015148 | −0.040763 | −0.079696 | −0.049157 | 0.005467 |
| RPL12 | −0.016258 | 0.013968 | 0.060789 | 0.025335 | 0.0628 | 0.024139 | 0.032193 | −0.061943 | −0.085718 | −0.027034 | 0.00612 |
| RPL7A | 0.002015 | 0.019488 | 0.045042 | 0.006342 | 0.068745 | 0.029252 | 0.029795 | −0.053796 | −0.089532 | −0.046624 | 0.017505 |
| RPS28 | 0.000829 | −0.017981 | 0.059331 | 0.021799 | 0.066231 | 0.021758 | 0.043487 | −0.066805 | −0.060909 | −0.053538 | 0.014241 |
| RPS19 | −0.01627 | 0.004334 | 0.031987 | −0.044418 | 0.051734 | 0.080074 | 0.039189 | −0.070921 | −0.056584 | −0.012878 | −0.003355 |
| RPL14 | −0.047322 | 0.001036 | 0.042627 | −0.03174 | 0.069912 | 0.062355 | 0.032145 | −0.038557 | −0.075346 | −0.01623 | 0.003329 |
| RPL19 | −0.044036 | −0.004775 | 0.041728 | −0.032493 | 0.065771 | 0.074984 | 0.022054 | −0.043945 | −0.069079 | −0.018784 | 0.007927 |
| SSR2 | −0.051893 | 0.008227 | 0.010438 | −0.0074 | 0.091003 | 0.048904 | 0.030051 | −0.059333 | −0.059484 | −0.022623 | 0.015507 |
| FTL | −0.040418 | 0.02324 | 0.046415 | −0.044821 | 0.084391 | 0.067121 | −0.013119 | −0.037577 | −0.036024 | −0.036995 | −0.00989 |
| RPL11 | −0.045627 | −0.00845 | 0.053353 | −0.011698 | 0.07989 | 0.067488 | 0.011725 | −0.019155 | −0.05416 | −0.048373 | −0.021471 |
| EEF1G | 0.006691 | −0.006993 | 0.037359 | −0.038991 | 0.100915 | 0.046985 | 0.017182 | −0.046783 | −0.048639 | −0.04113 | −0.019229 |
| SLC25A6 | −0.00871 | −0.021236 | 0.026419 | 0.008007 | 0.047553 | 0.076911 | 0.024754 | 0.036643 | −0.104144 | −0.006728 | 0.000421 |
| RPS11 | −0.025565 | −0.009639 | 0.0599 | −0.057346 | 0.059219 | 0.033101 | 0.027122 | −0.058852 | −0.029636 | −0.047837 | 0.052488 |
| RPS16 | −0.032842 | 0.006271 | 0.019851 | −0.044538 | 0.073978 | 0.0407 | 0.023904 | −0.046316 | −0.052531 | −0.051335 | 0.059801 |
| RPS5 | 0.024543 | 0.019057 | 0.041498 | −0.050147 | 0.062705 | 0.035646 | 0.035497 | −0.065561 | −0.055935 | −0.052369 | 0.021864 |
| GLTSCR2 | −0.000356 | 0.028526 | 0.053641 | −0.079196 | 0.067614 | 0.039113 | 0.016586 | −0.050657 | −0.019472 | −0.054647 | 0.006399 |
| RPS18 | −0.033774 | −0.024912 | 0.024762 | −0.060379 | 0.049494 | 0.063453 | −0.039447 | −0.032727 | −0.050245 | 0.018864 | 0.065641 |
| PIK3R1 | −0.04091 | −0.00876 | 0.036847 | −0.032897 | 0.097768 | 0.034334 | −0.030598 | −0.055594 | −0.04032 | −0.001392 | 0.041594 |
| FAU | −0.043814 | −0.013144 | 0.018366 | −0.060303 | 0.082796 | 0.038111 | −0.018158 | −0.025317 | −0.042869 | −0.021112 | 0.068443 |
| RPS3 | −0.031539 | −0.017711 | 0.066054 | −0.0456 | 0.081799 | 0.043545 | −0.010903 | −0.035583 | −0.066128 | 0.005885 | 0.013477 |
| RPLP2 | 0.012285 | −0.020227 | 0.012363 | −0.040467 | 0.085547 | 0.053262 | −0.011986 | −0.045866 | −0.057608 | −0.042109 | 0.049673 |
| RPL27A | −0.004616 | −0.016177 | 0.014554 | −0.041499 | 0.089512 | 0.073616 | −0.026676 | −0.021308 | −0.067092 | −0.027123 | 0.016159 |
| RPS2 | −0.076057 | −0.013095 | 0.026145 | −0.041661 | 0.05017 | 0.070365 | 0.033093 | −0.002571 | −0.068421 | −0.016523 | 0.020311 |
| RPL15 | −0.072712 | −0.011628 | 0.030178 | −0.004565 | 0.069047 | 0.056676 | −0.012165 | −0.019745 | −0.079438 | 0.005999 | 0.033086 |
| RPS24 | 0.003513 | 0.002953 | 0.036513 | −0.005668 | 0.062752 | 0.001695 | 0.068575 | −0.046949 | −0.06747 | −0.06681 | 0.032599 |
| SRRM2 | −0.079763 | 0.006021 | 0.025255 | −0.00865 | 0.050756 | 0.042795 | 0.033753 | −0.006677 | −0.043656 | −0.073731 | 0.047622 |
| LOC404266 | | | | | 0.037659 | 0.01685 | 0.098762 | | −0.086961 | | −0.057395 |
| H1FX | −0.065508 | −0.063956 | 0.009728 | 0.024471 | 0.048738 | 0.048539 | 0.070866 | −0.05634 | −0.010961 | −0.000974 | −0.013732 |
| RNASEK | −0.003495 | −0.054669 | −0.050941 | −0.0007 | −0.004544 | 0.011885 | −0.010341 | 0.007263 | −0.069379 | 0.056228 | 0.091756 |
| KDM6B | −0.060514 | 0.001105 | −0.0097 | −0.013307 | −0.036954 | 0.024749 | 0.025377 | −0.022592 | −0.06641 | 0.063395 | 0.082561 |
| SERF2 | −0.09308 | −0.028009 | −0.025765 | −0.02724 | 0.052805 | 0.021341 | 0.00347 | 0.067081 | 0.035698 | 0.000577 | −0.049273 |
| GNAI2 | −0.088531 | −0.058851 | −0.023766 | −0.029188 | 0.016712 | 0.032717 | −0.011014 | 0.07415 | 0.028417 | 0.033608 | −0.026231 |
| S100A11 | −0.090543 | −0.039576 | −0.032343 | 0.023918 | 0.028135 | 0.044856 | −0.04627 | 0.052559 | 0.010018 | 0.045185 | −0.032877 |
| CST3 | −0.055032 | −0.08132 | −0.009021 | 0.01649 | 0.004803 | 0.032859 | −0.015388 | 0.095609 | −0.0396 | −0.003984 | 0.015905 |
| COL6A1 | −0.069779 | −0.063088 | −0.024438 | 0.015019 | 0.024943 | 0.024161 | −0.022869 | 0.095093 | −0.032144 | 0.026083 | −0.01246 |
| FOXP4$ | −0.008059 | −0.061332 | −0.071757 | −0.041369 | 0.02723 | 0.035316 | 0.04645 | 0.00548 | 0.000058 | −0.049506 | 0.070697 |
| MAPKAPK2 | −0.05859 | −0.003595 | −0.076834 | −0.022338 | 0.016595 | −0.016445 | −0.011089 | 0.069557 | −0.036782 | 0.067586 | 0.032193 |
| EIF5A | −0.060294 | −0.033486 | −0.066135 | −0.034717 | −0.012491 | 0.012254 | 0.003992 | 0.034099 | −0.025174 | 0.086092 | 0.049459 |
| GNB2$ | −0.091733 | −0.04987 | −0.055687 | −0.038417 | −0.001269 | 0.030069 | 0.009392 | 0.049407 | 0.02588 | 0.012215 | 0.050787 |
| PTMS | −0.092155 | −0.019997 | −0.07792 | −0.011353 | −0.004888 | 0.050627 | −0.021819 | 0.02933 | 0.018599 | 0.037829 | 0.038976 |
| GAPDH$ | −0.070979 | −0.070644 | −0.062876 | −0.023314 | 0.009056 | 0.041773 | 0.02077 | 0.048178 | −0.011496 | 0.054821 | 0.008363 |
| EIF4A1 | −0.048745 | −0.021661 | −0.070264 | −0.067521 | 0.00079 | 0.060356 | −0.001531 | 0.050274 | −0.032199 | 0.042334 | 0.031125 |
| BCYRN1$ | −0.022577 | −0.052181 | −0.090681 | −0.042753 | 0.031596 | 0.019523 | 0.047645 | 0.066994 | 0.006929 | 0.00797 | −0.027922 |
| ALDOA$ | −0.055463 | −0.022221 | −0.094021 | −0.059792 | 0.008313 | 0.033223 | 0.041551 | 0.051918 | 0.01466 | 0.022737 | −0.000831 |
| PFN1 | −0.004153 | −0.063736 | −0.085149 | −0.057557 | −0.015657 | 0.009314 | 0.007251 | 0.029754 | 0.018942 | 0.033981 | 0.069904 |
| RALY | −0.018768 | −0.08998 | −0.079905 | −0.040564 | 0.01216 | 0.023154 | −0.007811 | 0.040406 | 0.043125 | 0.021733 | 0.033522 |
| TUBB$ | −0.009644 | −0.078529 | −0.067406 | −0.073258 | 0.035844 | 0.056806 | 0.008046 | 0.025901 | 0.003334 | 0.008989 | 0.028339 |
| MIDN$ | −0.072614 | −0.026722 | −0.062457 | −0.036645 | 0.029949 | 0.019687 | 0.090841 | −0.021605 | −0.000088 | 0.030199 | 0.012896 |
| BSG | −0.079026 | −0.051983 | −0.020591 | −0.023936 | 0.065276 | −0.013637 | 0.083124 | −0.022668 | 0.010048 | 0.015487 | 0.012525 |
| MRPS21$ | −0.089706 | −0.048083 | −0.017406 | −0.038892 | 0.055643 | 0.064821 | 0.003249 | −0.011306 | −0.023674 | 0.036037 | 0.029022 |
| CALM3 | −0.076628 | −0.034812 | 0.011408 | −0.065789 | 0.069671 | 0.062071 | 0.003938 | −0.014872 | −0.021751 | −0.003175 | 0.036656 |

TABLE 4-continued

Filtered 3' sequencing gene expression dataset of 3 YWHAE-FAM22A/B ESS
(2 YWHAE-FAM22A and 1 YWHAE-FAM22B), 4 JAZF1-rearranged ESS and 4 uterine
leiomyosarcomas (LMS); Genes marked $ and # are shown to be significantly
upregulated and downregulated in YWHAE-FAM22A/B ESS compared to JAZF1-rearranged ESS
respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | | | | | Sample code | | | | | | |
| | STT5519_ESS | STT5521_ESS | STT5520_ESS | STT5543-ESS | STT5774b_ESS | STT5775b_ESS | STT5776b_ESS | STT5837_LMS | STT5836_LMS | STT5838_LMS | STT5853_LMS |
| RPL29 | −0.112685 | −0.03681 | 0.004895 | −0.027467 | 0.027024 | 0.049433 | 0.040839 | −0.027472 | −0.006489 | 0.035887 | 0.023553 |
| FAM20C$ | −0.073279 | −0.031559 | −0.012932 | −0.058144 | 0.058913 | 0.044207 | 0.039228 | 0.041886 | −0.029534 | 0.02804 | −0.044963 |
| GUK1 | −0.009693 | −0.05822 | −0.061248 | −0.024706 | 0.002744 | 0.038447 | 0.036136 | 0.022694 | −0.057101 | 0.087743 | −0.014185 |
| TIMP1$ | −0.01103 | −0.08466 | −0.046989 | −0.058199 | 0.040801 | 0.027618 | 0.050347 | 0.04493 | −0.04304 | 0.022828 | 0.008599 |
| TPI1$ | −0.014242 | −0.061763 | −0.065641 | −0.037993 | 0.045221 | 0.064705 | 0.042254 | 0.009472 | −0.055697 | 0.036058 | −0.005797 |
| LSMD1$ | −0.022042 | −0.078965 | −0.032465 | −0.018289 | 0.054373 | 0.070804 | 0.050198 | −0.030522 | −0.048709 | 0.019644 | 0.004806 |
| CCND1$ | −0.051348 | −0.084964 | −0.045745 | −0.03034 | 0.040859 | 0.047299 | 0.054694 | −0.004065 | −0.028674 | 0.021065 | 0.035543 |
| SPTBN1 | −0.022102 | −0.08351 | −0.009123 | −0.036312 | 0.064821 | 0.044363 | 0.015304 | −0.036505 | −0.047749 | 0.036947 | 0.045459 |
| RPL35 | 0.022079 | −0.068549 | −0.02841 | −0.070487 | 0.03249 | 0.045095 | 0.028467 | −0.050986 | −0.016396 | 0.067088 | 0.00904 |
| C12orf57$ | −0.028884 | −0.049578 | −0.014856 | −0.055952 | 0.047335 | 0.03716 | 0.02375 | −0.037167 | −0.040502 | 0.091984 | 0.000606 |
| TBX2 | −0.01034 | −0.073855 | −0.016424 | −0.077411 | 0.05548 | −0.009304 | 0.046227 | −0.003231 | −0.023373 | 0.066984 | 0.011991 |
| SOD3 | 0.013577 | −0.084261 | −0.015594 | −0.084598 | 0.044872 | −0.03423 | 0.00156 | 0.05 | 0.033899 | 0.00393 | 0.027855 |
| ACTN4 | −0.035039 | −0.055338 | 0.00523 | −0.093696 | −0.018603 | 0.014718 | 0.01493 | 0.020965 | 0.087851 | −0.003236 | 0.016209 |
| FLNB | −0.020123 | −0.018631 | −0.024207 | −0.061688 | 0.023478 | 0.026716 | −0.020765 | −0.018099 | 0.0962 | −0.062307 | 0.044817 |
| TRIM28 | −0.08812 | 0.04033 | −0.053186 | −0.066223 | −0.011958 | 0.042967 | 0.011588 | 0.014015 | 0.031419 | −0.010767 | 0.047787 |
| SLC4A2 | −0.027173 | 0.07888 | −0.084222 | −0.057904 | −0.031732 | 0.008886 | 0.011636 | 0.026367 | 0.037435 | −0.023628 | 0.032087 |
| EIF3B | −0.034251 | 0.061592 | −0.044774 | −0.110025 | −0.013446 | −0.000202 | 0.018424 | 0.025079 | 0.024118 | 0.001888 | 0.038743 |
| KDELR1 | −0.006466 | 0.01062 | −0.02103 | −0.110642 | 0.013823 | 0.038496 | −0.053316 | 0.064984 | 0.02006 | −0.013212 | 0.012583 |
| FOSB | −0.001671 | 0.100432 | 0.01034 | −0.095754 | 0.021914 | −0.01835 | −0.022952 | −0.010893 | −0.020476 | 0.015049 | 0.02897 |
| CACNB3 | −0.006471 | 0.10514 | 0.032421 | 0.015093 | 0.00009 | 0.027269 | −0.021248 | −0.087292 | −0.018675 | −0.022016 | 0.016995 |
| SPSB3 | −0.015623 | 0.116962 | −0.010641 | −0.014906 | 0.003076 | 0.032568 | 0.004147 | −0.03133 | −0.009858 | −0.074681 | 0.017591 |
| CPSF3L | −0.000588 | 0.111476 | 0.005749 | −0.035772 | 0.013707 | 0.039593 | 0.004136 | −0.028559 | −0.027374 | −0.071921 | 0.007898 |
| TSPYL2 | −0.029583 | 0.12125 | 0.021609 | −0.006251 | 0.011512 | 0.00459 | −0.033826 | −0.012286 | 0.013424 | −0.067779 | 0.002621 |
| NUMA1 | −0.059885 | 0.101871 | −0.003767 | 0.01716 | 0.007256 | 0.021371 | −0.049497 | −0.023614 | 0.025748 | −0.05423 | 0.030317 |
| RGS12 | 0.039494 | 0.12855 | −0.015214 | 0.016595 | −0.045559 | −0.028371 | −0.007463 | −0.005726 | −0.019711 | −0.007899 | −0.017341 |
| TMEM120B | −0.004058 | 0.112827 | −0.042763 | 0.048673 | −0.037323 | −0.020861 | −0.032607 | −0.0102 | −0.026246 | −0.003014 | 0.040927 |
| NR2F6 | −0.040956 | 0.122629 | −0.054259 | −0.008144 | 0.015057 | 0.001995 | −0.011595 | −0.039729 | −0.000067 | −0.001555 | 0.025318 |
| AKNA | −0.044853 | 0.131556 | −0.010093 | −0.007163 | −0.008636 | −0.038137 | −0.018849 | −0.000942 | −0.017257 | 0.019024 | 0.017193 |
| CAD | −0.033675 | 0.107677 | −0.062898 | 0.000618 | −0.0113 | 0.01761 | 0.000423 | 0.052424 | −0.010562 | −0.022732 | −0.04258 |
| TMEM214 | 0.009892 | 0.109627 | −0.019546 | −0.000267 | 0.027958 | 0.017899 | 0.009116 | 0.016918 | −0.029672 | −0.064041 | −0.057977 |
| TSKU | −0.015901 | 0.07638 | −0.018121 | 0.051546 | 0.015521 | −0.020767 | −0.077722 | 0.026519 | −0.060582 | −0.003487 | 0.046278 |
| NAB2 | −0.080626 | 0.066823 | −0.02002 | 0.002656 | 0.033831 | 0.043336 | −0.041688 | 0.000095 | −0.05148 | −0.016193 | 0.057148 |
| NISCH | −0.08417 | 0.098175 | −0.006354 | −0.02863 | 0.014456 | 0.045286 | 0.012959 | −0.029022 | 0.01707 | −0.005694 | −0.033701 |
| U2AF2 | −0.115997 | 0.057403 | −0.04642 | 0.014905 | −0.012775 | 0.044482 | 0.002829 | 0.020667 | 0.023178 | −0.008032 | −0.002529 |
| MXD4 | −0.084513 | 0.048798 | −0.051664 | −0.027492 | −0.004867 | 0.083675 | −0.0184 | 0.020965 | −0.01504 | 0.03253 | −0.016616 |
| AUP1 | −0.051959 | 0.078841 | −0.035843 | −0.046816 | 0.000389 | 0.016995 | −0.009909 | 0.053855 | 0.007131 | 0.040248 | −0.070442 |
| TMED9 | −0.071575 | 0.027233 | −0.055067 | 0.036768 | 0.030981 | 0.026725 | −0.051262 | 0.075069 | −0.028618 | 0.018885 | −0.030834 |
| CTSA | −0.089829 | 0.035824 | −0.016838 | 0.035085 | −0.008524 | 0.036795 | −0.015787 | 0.073604 | 0.013691 | −0.017236 | −0.06231 |
| SEC61A1 | −0.031634 | 0.023904 | −0.055246 | 0.036141 | 0.000503 | 0.044145 | −0.033207 | 0.033666 | 0.024233 | 0.042043 | −0.099206 |
| MVP | −0.085514 | 0.019431 | −0.017381 | −0.038056 | 0.008944 | −0.011229 | −0.021193 | 0.078609 | 0.069433 | −0.001447 | −0.034844 |
| TMSB10 | −0.026675 | 0.009737 | −0.063662 | −0.005504 | −0.052325 | 0.069715 | 0.05919 | 0.036475 | −0.040559 | 0.033352 | −0.047258 |
| ADAMTS10 | −0.042156 | 0.046903 | 0.002419 | −0.009516 | −0.031613 | 0.026682 | 0.024834 | −0.06229 | 0.101486 | −0.015175 | −0.038745 |
| FAM113A | 0.054511 | 0.04022 | 0.044171 | −0.013249 | −0.001153 | 0.026881 | 0.014441 | −0.043531 | −0.02293 | 0.037261 | −0.104187 |
| IGFBP2 | 0.043129 | 0.013755 | 0.043155 | −0.004216 | 0.00579 | 0.074182 | −0.005418 | −0.022926 | −0.03663 | 0.012147 | −0.103933 |
| GP1BB | 0.064057 | 0.056532 | 0.014911 | −0.022611 | 0.021644 | 0.012556 | 0.019629 | −0.077843 | 0.009043 | 0.016695 | −0.082753 |
| ATHL1 | 0.058005 | 0.06356 | 0.051361 | 0.013741 | 0.001216 | −0.024604 | −0.017502 | −0.005606 | −0.033215 | 0.033512 | −0.094395 |
| EEF1A2 | 0.026998 | 0.015702 | 0.062168 | 0.054365 | −0.016733 | 0.005048 | 0.029611 | | −0.024183 | | −0.112914 |
| DPP7# | 0.059126 | 0.059706 | 0.052737 | 0.056367 | −0.004302 | −0.009565 | −0.001068 | −0.029615 | −0.022648 | −0.018463 | −0.08632 |
| CPZ | 0.032134 | 0.056398 | 0.061638 | 0.059764 | 0.022847 | −0.016148 | 0.002698 | −0.030305 | −0.01338 | −0.031582 | −0.088562 |
| RASSF7 | 0.052528 | 0.044697 | 0.047523 | 0.018721 | −0.003447 | 0.017498 | 0.0599 | −0.040484 | −0.022605 | −0.05757 | −0.074673 |
| C1QL1 | 0.019423 | 0.021569 | 0.043947 | 0.050987 | 0.013149 | 0.024943 | 0.008428 | −0.004242 | 0.024885 | −0.072524 | −0.100875 |
| WBP1 | 0.003734 | 0.030443 | −0.018809 | −0.020725 | 0.052095 | 0.077879 | 0.025181 | −0.010417 | −0.043434 | −0.002746 | −0.095774 |
| GPC1 | −0.000705 | 0.026913 | 0.016693 | 0.032024 | 0.005509 | 0.053607 | 0.037912 | 0.011206 | −0.038127 | −0.008947 | −0.11951 |
| MMP17 | −0.003341 | 0.026227 | 0.005274 | 0.00919 | 0.024024 | 0.048413 | 0.05765 | 0.025633 | −0.018785 | −0.079452 | −0.089074 |
| OBSL1 | −0.004724 | 0.018212 | 0.018152 | −0.003727 | 0.030723 | 0.085028 | 0.059467 | −0.055948 | −0.030561 | −0.062623 | −0.043809 |
| EMID2 | 0.019471 | 0.01786 | 0.060221 | 0.026046 | 0.040304 | 0.056326 | 0.026739 | −0.040305 | −0.070044 | −0.04999 | −0.052609 |
| LMF1 | 0.021086 | −0.002298 | 0.019283 | 0.016993 | 0.042498 | 0.044555 | 0.066795 | | −0.059846 | −0.05293 | −0.081031 |
| NTNG2 | −0.004604 | −0.027888 | 0.027232 | 0.008193 | 0.037094 | 0.066171 | 0.070334 | −0.040827 | −0.063469 | −0.065635 | |
| FGFR3 | 0.007385 | 0.028298 | 0.032045 | 0.033483 | 0.02719 | 0.041408 | 0.054049 | −0.014083 | −0.021639 | −0.084006 | −0.078942 |
| BAI1 | 0.00266 | 0.02665 | 0.022013 | 0.025945 | 0.026968 | 0.048367 | 0.057155 | −0.037398 | −0.04353 | | −0.103974 |
| SOX8 | −0.007901 | 0.014771 | 0.026043 | 0.026561 | 0.060982 | 0.042895 | 0.051162 | −0.063715 | | −0.073497 | −0.054867 |
| KIF1A | 0.001612 | 0.033211 | 0.032139 | 0.034307 | 0.032799 | 0.050712 | 0.058894 | −0.04366 | −0.045731 | −0.070594 | −0.05385 |
| ECEL1 | −0.006993 | −0.02362 | 0.029198 | 0.044981 | 0.026551 | 0.050737 | 0.049423 | | | −0.090677 | −0.069897 |
| HAGHL | 0.007178 | 0.005335 | 0.011137 | 0.01447 | −0.006824 | 0.051122 | 0.082929 | −0.043055 | 0.024724 | −0.085167 | −0.051414 |

TABLE 4-continued

Filtered 3' sequencing gene expression dataset of 3 YWHAE-FAM22A/B ESS
(2 YWHAE-FAM22A and 1 YWHAE-FAM22B), 4 JAZF1-rearranged ESS and 4 uterine
leiomyosarcomas (LMS); Genes marked $ and # are shown to be significantly
upregulated and downregulated in YWHAE-FAM22A/B ESS compared to JAZF1-rearranged ESS
respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | | | | | Sample code | | | | | | |
| | STT5519_ESS | STT5521_ESS | STT5520_ESS | STT5543-ESS | STT5774b_ESS | STT5775b_ESS | STT5776b_ESS | STT5837_LMS | STT5836_LMS | STT5838_LMS | STT5853_LMS |
| SLC25A29 | 0.011776 | 0.016704 | −0.007721 | −0.033107 | −0.002465 | 0.078957 | 0.088233 | −0.025097 | −0.042875 | −0.028667 | −0.058512 |
| LTBP4# | 0.019236 | 0.066143 | 0.070047 | 0.031384 | −0.026616 | −0.060797 | −0.045206 | −0.01838 | 0.011616 | −0.048939 | 0.048578 |
| BTBD2 | −0.005384 | 0.057351 | 0.023007 | 0.093921 | −0.007403 | −0.083807 | −0.012108 | −0.0014 | −0.000766 | −0.042147 | 0.025293 |
| TMEM132A | −0.014602 | 0.04126 | 0.063091 | 0.069509 | −0.056187 | −0.032695 | −0.001738 | −0.034918 | −0.05007 | 0.002577 | 0.060191 |
| C10orf116 | −0.013898 | 0.027647 | 0.07189 | 0.092143 | −0.040855 | −0.018875 | 0.008702 | −0.068829 | −0.023555 | 0.002411 | 0.017236 |
| BMP1# | 0.053006 | 0.088706 | 0.02398 | 0.015987 | −0.026397 | −0.05959 | −0.066142 | −0.000239 | 0.024804 | 0.020062 | −0.034103 |
| MAP1LC3A# | 0.056674 | 0.012933 | 0.074347 | 0.05924 | −0.006663 | −0.063652 | −0.040892 | −0.043472 | −0.008189 | 0.039763 | −0.024292 |
| PODXL2 | 0.019636 | 0.009176 | 0.062625 | 0.093529 | −0.017248 | −0.051196 | −0.019306 | −0.020947 | −0.041987 | 0.051046 | −0.032778 |
| AMN# | 0.041533 | 0.048098 | 0.077435 | 0.076346 | −0.03885 | −0.033302 | −0.007622 | −0.026063 | | −0.030761 | −0.046337 |
| SEMA6B# | 0.039827 | 0.036421 | 0.063141 | 0.09563 | −0.046745 | −0.030824 | −0.010896 | −0.039689 | 0.003707 | −0.019335 | −0.032421 |
| CALY# | 0.036646 | 0.037142 | 0.084463 | 0.081888 | −0.033437 | −0.017402 | −0.029605 | −0.045155 | −0.028738 | | −0.024252 |
| SPINT1# | 0.041196 | 0.04696 | 0.061495 | 0.076009 | −0.067195 | −0.035619 | −0.047897 | 0.00991 | −0.022865 | −0.012329 | |
| GCGR# | 0.041008 | 0.062137 | 0.059836 | 0.047377 | −0.085892 | −0.026405 | −0.053574 | | | | |
| ECM1 | −0.002382 | 0.084621 | 0.044664 | 0.083265 | −0.013476 | −0.018564 | −0.032906 | −0.015373 | −0.001267 | −0.011003 | −0.065193 |
| IFITM1# | 0.011676 | 0.066801 | 0.042544 | 0.089706 | −0.010816 | −0.048772 | −0.044228 | −0.032424 | 0.015142 | 0.010489 | −0.044879 |
| LY6E | 0.024702 | 0.049562 | 0.04419 | 0.083282 | 0.001452 | −0.019376 | −0.068503 | 0.004697 | −0.003866 | 0.001977 | −0.072429 |
| MZT2B# | 0.063394 | 0.040425 | 0.023325 | 0.080566 | −0.02313 | −0.012738 | −0.041183 | −0.065564 | 0.006263 | 0.026185 | −0.046986 |
| RARRES2# | 0.012912 | 0.041136 | 0.064012 | 0.046658 | −0.059067 | −0.049364 | −0.014429 | −0.069137 | 0.041369 | 0.039082 | −0.005132 |
| MMP2 | 0.006212 | 0.029102 | 0.066127 | 0.024273 | 0.046519 | 0.004148 | −0.039784 | 0.037434 | −0.012867 | −0.099058 | −0.036353 |
| ISLR | 0.024912 | 0.034929 | 0.065805 | 0.033256 | 0.044915 | −0.008237 | −0.017183 | 0.010498 | −0.043231 | −0.103228 | −0.004466 |
| HTRA1 | −0.029809 | −0.0205 | 0.025668 | 0.012807 | 0.067906 | 0.056931 | −0.042121 | 0.03517 | −0.008296 | −0.095451 | −0.011722 |
| IFITM3 | −0.036797 | 0.047354 | 0.044832 | 0.080272 | 0.044228 | −0.029378 | −0.081745 | −0.012587 | 0.006714 | −0.001631 | −0.023555 |
| ASS1 | −0.013377 | 0.059631 | 0.040231 | 0.035861 | 0.022082 | 0.013186 | −0.112287 | 0.004034 | 0.027707 | −0.035762 | −0.018452 |
| SEMA3B | −0.030186 | 0.068094 | 0.066948 | 0.037715 | 0.024645 | 0.001501 | −0.057048 | 0.016007 | 0.015859 | −0.040366 | −0.069704 |
| ADAMTSL4 | −0.019876 | 0.104185 | 0.047605 | 0.035463 | 0.029562 | −0.055139 | −0.04819 | −0.004185 | 0.004104 | −0.014921 | −0.032334 |
| NBL1 | −0.046132 | 0.035405 | 0.006867 | 0.100647 | 0.04167 | −0.003004 | −0.047172 | −0.009784 | −0.013339 | −0.06289 | 0.023543 |
| ITM2B | −0.016962 | 0.043076 | 0.03645 | 0.112195 | 0.001892 | −0.010601 | −0.059387 | −0.00792 | −0.049245 | −0.01009 | 0.004513 |
| FBLN1 | −0.035932 | 0.05587 | 0.087056 | 0.045262 | 0.054232 | −0.016244 | −0.030864 | −0.003746 | −0.036077 | −0.040117 | −0.034494 |
| PHLDB1 | −0.050132 | 0.058767 | 0.049353 | 0.079966 | 0.041396 | −0.032159 | −0.012172 | −0.001798 | −0.064723 | −0.020235 | −0.004197 |
| COL3A1 | −0.025593 | −0.018997 | 0.054795 | 0.087217 | 0.011496 | −0.024787 | −0.08184 | 0.040681 | 0.021119 | −0.012071 | −0.031561 |
| TSPAN4 | 0.016146 | −0.025511 | 0.101925 | 0.070223 | −0.002095 | −0.019239 | −0.067923 | −0.004897 | −0.004008 | −0.03181 | 0.006401 |
| TMEM119 | −0.023416 | 0.02713 | 0.009928 | 0.074504 | 0.040341 | 0.02667 | −0.051501 | 0.054891 | −0.032795 | −0.049668 | −0.061906 |
| MRC2 | −0.033092 | 0.012677 | 0.02902 | 0.031408 | 0.053161 | 0.047617 | −0.081174 | 0.055154 | −0.049512 | −0.025415 | −0.037496 |
| IFITM2 | −0.011216 | −0.007388 | 0.063234 | 0.042392 | 0.074193 | 0.022289 | −0.045007 | 0.025091 | −0.057811 | −0.021408 | −0.062284 |
| PCOLCE | −0.03314 | 0.001445 | 0.034681 | 0.021606 | 0.040465 | 0.025633 | −0.059822 | 0.065605 | −0.014391 | 0.01324 | −0.094777 |
| PLOD1 | 0.044203 | 0.043214 | 0.013245 | 0.037819 | 0.014729 | 0.004141 | −0.087427 | 0.042192 | 0.011887 | −0.022188 | −0.081203 |
| HSPB6 | 0.013493 | −0.021657 | 0.022173 | −0.028463 | 0.093566 | −0.029346 | −0.027916 | −0.058827 | −0.002277 | −0.029174 | 0.075149 |
| C19orf56 | −0.048486 | 0.021386 | 0.007554 | 0.011278 | 0.111747 | −0.009865 | −0.022847 | −0.051092 | −0.006797 | −0.043288 | 0.041019 |
| ABL1 | −0.072789 | −0.000532 | 0.059016 | 0.037625 | 0.043461 | 0.017894 | −0.034552 | −0.018777 | −0.029997 | −0.055033 | 0.066569 |
| EEF1A1 | −0.030069 | −0.01458 | 0.05963 | 0.028261 | 0.030948 | 0.003903 | −0.048818 | −0.006135 | −0.039743 | −0.060684 | 0.090473 |
| CDC42EP4 | −0.018065 | 0.004749 | 0.024598 | 0.026016 | 0.053578 | 0.050002 | −0.031444 | −0.033871 | −0.033505 | −0.092239 | 0.059533 |
| RPL26 | −0.022369 | −0.023692 | 0.100335 | 0.039285 | 0.045518 | 0.020782 | −0.008362 | −0.022552 | −0.066956 | −0.043722 | 0.012772 |
| CHCHD10 | −0.029824 | 0.026594 | 0.056257 | 0.023011 | 0.086731 | 0.003728 | −0.037999 | −0.016245 | −0.084659 | −0.017365 | 0.017566 |
| CD81 | −0.035628 | 0.018035 | 0.061008 | 0.037107 | 0.069646 | 0.031955 | −0.047636 | −0.056748 | −0.054877 | −0.021888 | 0.027697 |
| FTH1 | −0.028243 | 0.016048 | 0.055453 | 0.033826 | 0.086966 | 0.005719 | 0.002635 | −0.044255 | −0.036046 | −0.077179 | 0.01486 |
| VWA1 | 0.026505 | −0.04176 | 0.050636 | 0.060954 | 0.057749 | 0.011123 | −0.037536 | −0.058587 | −0.042083 | −0.041047 | 0.042787 |
| RPS25 | −0.069841 | −0.014072 | 0.053188 | −0.006269 | 0.085035 | −0.006695 | −0.029553 | −0.011309 | −0.057396 | 0.009561 | 0.051981 |
| DCHS1 | 0.00015 | 0.036004 | 0.001989 | 0.0428 | 0.035732 | 0.010731 | −0.04148 | −0.050276 | 0.003125 | −0.091162 | 0.072248 |
| PSD | 0.040071 | 0.03039 | −0.020637 | 0.02704 | 0.018496 | 0.01486 | −0.01861 | −0.041875 | −0.035154 | −0.085253 | 0.086367 |
| SFRP1 | 0.008535 | 0.04835 | −0.003922 | 0.071481 | 0.015535 | −0.016026 | −0.014177 | | −0.072868 | −0.069446 | 0.062812 |
| MMP11 | 0.005486 | 0.078499 | 0.008836 | 0.063918 | 0.041389 | −0.014806 | −0.018089 | −0.037626 | −0.066648 | −0.051624 | 0.03426 |
| TBX1 | 0.039112 | 0.099958 | 0.043474 | 0.03136 | 0.020951 | −0.017925 | −0.00933 | −0.028694 | −0.037142 | −0.066346 | −0.021582 |
| SNED1 | −0.004265 | 0.086462 | 0.042613 | 0.04766 | 0.038901 | 0.018944 | 0.000477 | −0.039359 | −0.035822 | −0.045909 | −0.0626 |
| SERPINF1 | | 0.04849 | 0.053975 | −0.013889 | 0.074365 | 0.032749 | −0.036186 | 0.007012 | −0.070178 | −0.061609 | −0.013151 |
| SAT2 | 0.046598 | 0.058946 | 0.054384 | 0.016623 | 0.020769 | 0.036659 | −0.006958 | −0.047 | −0.085025 | −0.046377 | −0.044441 |
| KRT19 | 0.08804 | 0.072417 | 0.044586 | 0.023113 | | | −0.028529 | −0.024335 | −0.031167 | −0.045158 | −0.048769 |
| PTH1R | 0.027273 | 0.048457 | 0.035574 | 0.004628 | 0.05182 | 0.071586 | −0.03727 | −0.043059 | −0.066146 | −0.045271 | −0.02135 |
| CACNA1G | 0.005892 | 0.048789 | 0.015325 | 0.025182 | 0.041902 | 0.066201 | 0.000441 | 0.005037 | −0.065217 | −0.082422 | −0.042635 |
| ANGPTL4 | 0.062565 | −0.008966 | 0.093269 | 0.048635 | −0.004323 | 0.019516 | −0.036674 | −0.061426 | −0.036813 | −0.015708 | −0.011255 |
| RPS27 | 0.00404 | 0.030714 | 0.085214 | 0.072535 | 0.032565 | −0.023207 | −0.014098 | −0.045881 | −0.038726 | −0.057627 | 0.010318 |
| IGFBP4 | 0.003956 | 0.049615 | 0.031091 | 0.085416 | 0.053591 | −0.033291 | −0.032252 | −0.047524 | −0.032966 | −0.051644 | 0.023227 |
| PTGDS | 0.009783 | 0.004564 | 0.073692 | 0.069126 | 0.042062 | 0.009275 | −0.034069 | −0.090389 | −0.009871 | −0.02652 | −0.000117 |
| RBP1 | 0.018348 | 0.049521 | 0.066169 | 0.061858 | 0.055548 | −0.00137 | −0.045467 | −0.038811 | −0.053989 | −0.03065 | −0.028344 |
| CRLF1 | 0.030842 | 0.017853 | 0.056271 | 0.050882 | 0.056146 | 0.029376 | 0.005894 | −0.078554 | −0.046178 | −0.038245 | −0.038356 |

TABLE 4-continued

Filtered 3' sequencing gene expression dataset of 3 YWHAE-FAM22A/B ESS
(2 YWHAE-FAM22A and 1 YWHAE-FAM22B), 4 JAZF1-rearranged ESS and 4 uterine
leiomyosarcomas (LMS); Genes marked $ and # are shown to be significantly
upregulated and downregulated in YWHAE-FAM22A/B ESS compared to JAZF1-rearranged ESS
respectively by SAM analysis (*Numbering for YWHAE-FAM22 ESS corresponds to that in Table 3).

| | Tumor | | | | | | | | | | |
|---|---|---|---|---|---|---|---|---|---|---|---|
| | JAZF1-ESS-1 | JAZF1-ESS-2 | JAZF1-ESS-3 | JAZF1-ESS-4 | YWHAE-FAM22A-ESS-1* | YWHAE-FAM22A-ESS-2* | YWHAE-FAM22B-ESS-9* | LMS-1 | LMS-2 | LMS-3 | LMS-4 |
| | | | | | Sample code | | | | | | |
| | STT55 19_ESS | STT55 21_ESS | STT55 20_ESS | STT5543-ESS | STT577 4b_ESS | STT577 5b_ESS | STT577 6b_ESS | STT58 37_LMS | STT5836_LMS | STT58 38_LMS | STT5853_LMS |
| NPDC1 | 0.016359 | 0.050609 | 0.055156 | 0.044605 | 0.04041 | 0.033512 | −0.011126 | −0.095109 | −0.025962 | −0.034981 | −0.02507 |
| TMEM59L | 0.035245 | 0.027255 | 0.071597 | 0.062193 | 0.035157 | 0.023163 | −0.020722 | −0.050958 | −0.042913 | −0.063139 | −0.026581 |
| LAMC3 | 0.000685 | 0.009951 | 0.082964 | 0.075159 | 0.025804 | −0.003694 | −0.029783 | | −0.077873 | 0.00755 | −0.044646 |
| PCSK1N | 0.026409 | 0.020207 | 0.059495 | 0.076881 | −0.000782 | 0.006883 | −0.037242 | −0.072629 | −0.060985 | −0.004245 | 0.036182 |
| GABARAP | 0.053294 | 0.01325 | 0.050356 | 0.039338 | 0.011941 | −0.006516 | 0.037251 | −0.052314 | −0.086336 | −0.048421 | 0.033247 |
| NPW | 0.041469 | 0.035391 | 0.060216 | 0.058683 | −0.016375 | 0.034371 | 0.024491 | −0.033738 | −0.073476 | −0.05237 | −0.030683 |
| RAMP1 | 0.033963 | 0.033888 | 0.028154 | 0.044487 | 0.036322 | −0.020792 | −0.02024 | −0.114807 | 0.007372 | −0.020936 | 0.037472 |
| SHC2 | 0.061167 | 0.046148 | 0.058129 | 0.017879 | −0.024096 | −0.019536 | 0.034242 | −0.096547 | −0.034818 | 0.00559 | 0.006566 |
| PRDX2 | 0.005661 | 0.015533 | 0.015424 | 0.050532 | −0.017145 | 0.016709 | 0.039847 | −0.123283 | −0.017082 | 0.008714 | 0.038991 |
| NGFR | −0.033262 | 0.006737 | 0.006113 | 0.049982 | 0.033394 | 0.051332 | 0.045643 | −0.094842 | −0.058632 | 0.018571 | −0.003737 |
| CTXN1 | 0.012659 | 0.008398 | −0.001684 | 0.012879 | −0.004593 | 0.022663 | 0.052676 | −0.100538 | 0.028213 | −0.06956 | 0.053489 |

TABLE 5

Specificity of YWHAE-FAM22A/B genetic rearrangement by
FISH assays in uterine and extrauterine mesenchymal tumors
(n = 827 cases, representing 55 tumor types)

| FISH screen for YWHAE-FAM22A and YWHAE-FAM22B | No. of cases screened | No. of positive cases |
|---|---|---|
| Uterine lesions | | |
| Classic ESS | 38 | 0 |
| Uterine adenosarcoma/carcinosarcoma | 16 | 0 |
| Uterine leiomyosarcoma | 105 | 0 |
| Uterine leiomyoma | 66 | 0 |
| Polypoid endometriosis | 7 | 0 |
| Soft-tissue tumors | | |
| Leiomyosarcoma | 206 | 0 |
| Undifferentiated pleomorphic sarcoma | 59 | 0 |
| Gastrointestinal stromal tumor | 51 | 0 |
| Desmoid type fibromatosis | 22 | 0 |
| Angiosarcoma | 21 | 0 |
| Solitary fibrous tumor | 13 | 0 |
| Dedifferentiated liposarcoma | 12 | 0 |
| Embryonal rhabdomyosarcoma | 12 | 0 |
| Synovial sarcoma | 12 | 0 |
| Dermatofibrosarcoma protuberans | 10 | 0 |
| Myxoid liposarcoma | 10 | 0 |
| Malignant peripheral nerve sheath tumor | 7 | 0 |
| Myxofibrosarcoma | 6 | 0 |
| Other benign and malignant mesenchymal tumors | 154 | 0 |
| Total | 827 | 0 |

In the work reported herein, the inventors have identified an oncogenic mechanism for 14-3-3 proteins Ian the form of a transforming YWHAE-FAM22A/B fusion oncoprotein. The translocation-mediated YWHAE-FAM22A/B, fusions define a previously unrecognized group of uterine sarcoma, which is clinically more aggressive and histologically higher grade than JAZF1-rarranged ESS. YWHAE-FAM22A/B oncogenic fusion results in nuclear accumulation of the functionally intact YWHAE protein-interaction domain. Known cytoplasmic YWHAE protein-protein interactions are thereby likely redirected to the nuclear compartment. Disruption of YWHAE interaction in the nuclear compartment therefore would appear to be a rational therapeutic approach. This unique genetic fusion provides a compelling opportunity to characterize 14-3-3 functions in cancer development and progression.

REFERENCES

1. Aitken A (2006) *14-3-3 proteins: A historic overview.* Semin Cancer Biol. 16:162-172.
2. Mackintosh C a(2004) *Dynamic interactions between 14-3-3 proteins and phosphoproteins regulate diverse cellular processes.* Biochem J 381:329-342,
3. Hermeking H (2003) *The 14-3-3 cancer connection.* Nat Rev Cancer 3:931-943.
4. Morrison D K (2009) *The 14-3-3 proteins: Integrators of diverse signaling cues that impact cell fate and cancer development.* Trends Cell Biol 19:16-23,
5. Lodygin D Herineking H(2006) *Epigenetic silencing of 14-3-3σ in cancer.* Semin Cancer Biol 16:214-224.
6. Chan T A, et al. (1999) *14-3-3σ is required to prevent mitotic catastrophe after DNA damage.* Nature 401:616-620.
7. Wilker E W, et al. (2007) *14-3-3σ controls mitotic translation to facilitate cytokinesis.* Nature 446:329-332.
8. Neal C L, et al. (2009) *14-3-3ζ overexpression defines high risk for breast cancer recurrence and promotes cancer cell survival.* Cancer Res 69:3425-3432.
9. Li Z, et al, (2008) *Down-regulation of 14-3-3ζ suppresses anchorage-independent growth of lung cancer cells through anoikis activation.* Proc Natl Acad Sci USA 105:162-167.
10. Lu J, et al. (2009) *14-3-3ζ cooperates with ErbB2 to promote ductal carcinoma in situ progression to invasive breast cancer by inducing epithelial-mesenchymal transition.* Cancer Cell 16:195-207
11. Koontz J I, et, al. (2001) *Frequent fusion of the JAZF1 and JJAZ1 genes in endometrial stromal tumors.* Proc Natl Acad Sci USA 98:6348-6353.
12. Micci F, et al. (2006) *Consistent rearrangement of chromosomal band 6p21 with generation of fusion genes*

- *JAZF1/PHF1 and EPC1/PHF1 in endometrial stromal sarcoma. Cancer Res* 66:107-112.
13. McPherson A, et al. (2011) *deFuse: An algorithm for gene fusion discovery in tumor RNA-Seq data. PLOS Comput Biol* 7:e1001138.
14. French C A, et al. (2003) *BRD-NUT fusion oncogene: A novel mechanism in aggressive carcinoma, Cancer Res* 63:304-307.
15. French C A, et al. (2008) *BRD-NUT oncoproteins: A family of closely related nuclear proteins that block epithelial differentiation and maintain the growth of carcinoma cells. Oncogene* 27:2237-2242.
16. Gardino A K, Sinerdon S J, Yaffe M B (2006) *Structural determinants of 14-3-3 binding specificities and regulation of subcellular localization of 14-3-3-ligand complexes: A comparison of the X-ray crystal structures of all human 14-3-3 isoforms, Semin Cancer Biol* 16:173-182.
17. Brunet A, et al. (2002) *14-3-3 transits to the nucleus and participates to dynamic nucleocytoplasmic transport. J Cell Biol* 156:817-828.
18. Brameier M, Krings A, MacCallum R M (2007) *NucPred-predicting nuclear localization of proteins. Bioinformatics* 23:1159-1160.
19. Briesemeister S, Rahnenführer J, Kohlbacher O (2010) *Going from where to why—interpretable prediction of protein subcellular localization. Bioinformatics* 26:1232-1238,
20. Nakai K, Horton P (1999) *PSORT: A program for detecting sorting signals in proteins and predicting their subcellular localization. Trends Biochem Sci* 24:34-36.
21. Fletcher J A, et al. (1991) *Diagnostic relevance of clonal cytogenetic aberrations m soft-tissue tumors. N Engl J Med* 324:436-442.
22. Shah S P, et al. (2009) *Mutation of FOXL2 in granulosa-cell tumors of the ovary. N Engl J Med* 360:2719-2729.
23. Shah S P, et al. (2009) *Mutational evolution in a lobular breast tumour profiled at single nucleotide resolution. Nature* 461:809-813.
24. Wiegand K C, et al. (2010) *ARID1A mutations endometriosis-associated ovarian carcinomas. N Engl Med* 363:1532-1543.
25. Rubin B P, et al. (2001) *KIT activation is a ubiquitous feature of gastrointestinal stromal tumors. Cancer Res* 61:8118-8121.
26. Shaw R J, et al. (2001) *The Nf2 tumor suppressor, merlin, functions in Rac-dependent signaling. Dev Cell* 1:63-72.
27. Beck A H, et al. (2010) *3'-end sequencing Thr expression quantification (3SEQ) from archival tumor samples. PLoS ONE* 5:e8768.
28. Li R, et al. (2009) *SOAP2: An improved ultrafast tool for short read alignment. Bioinformatics* 25:1966-1967.

Sequences:

```
(Nucleotide sequence of nucleic acid encoding YWHAE-FAM22A)
                                                    SEQ ID NO: 1
ATGGATGATCGAGAGGATCTGGTGTACCAGGCGAAGCTGGCCGAGCAGGCTGAGCG

ATACGACGAAATGGTGGAGTCAATGAAGAAAGTAGCAGGGATGGATGTGGAGCTGA

CAGTTGAAGAAAGAAACCTCCTATCTGTTGCATATAAGAATGTGATTGGAGCTAGA

AGAGCCTCCTGGAGAATAATCAGCAGCATTGAACAGAAAGAAGAAAACAAGGGAGG

AGAAGACAAGCTAAAAATGATTCGGGAATATCGGCAAATGGTTGAGACTGAGCTAA

AGTTAATCTGTTGTGACATTCTGGATGTACTGGACAAACACCTCATTCCAGCAGCT

AACACTGGCGAGTCCAAGGTTTTCTATTATAAAATGAAAGGGGACTACCACAGGTA

TCTGGCAGAATTTGCCACAGGAAACGACAGGAAGGAGGCTGCGGAGAACAGCCTAG

TGGCTTATAAAGCTGCTAGTGATATTGCAATGACAGAACTTCCACCAACGCATCCT

ATTCGCTTAGGTCTTGCTCTCAATTTTTCCGTATTCTACTACGAAATTCTTAATTC

CCCTGACCGTGCCTGCAGGTTGGCAAAAGCAGCTTTTGATGATGCAATTGCAGAAC

TGGATACGCTGAGTGAAGAAAGCTATAAGGACTCTACACTTATCATGCAGTTGTTA

CGTGATAATCTGACACTATGGACTTCAGACATGCAGGGTGACGCATACCCAGCGCT

GGGACCGGGCGTGACCGCGAACCCTGGCACCTCCCTGTCTGTGTTCACGGCTCTGC

CCTTCACCACACCCGCTCCCGGCCCAGCACACGGGCCGCTCCTTGTGACTGCAGGG

GCTCCTCCAGGCGGCCCTCTGGTGCTGTCTACCCTCCCCAGCACACCTCTGGTGAC

AGAACAGGATGGCTGCGGCCCGAGTGGGGCCGGGGCTTCCAACGTCTTTGTCCAGA

TGAGGACAGAGGTGGGGCCTGTGAAGGCCGCTCAGGCGCAGACCTTGGTCCTAACT

CAGGCCCCCTCGTCTGGCAGGCTCCAGGCGCCCTCTGCGGAGGTGTTGTGTGTCC

ACCTCCCCTACTCCTGGCAGCTGCTCCTGTGGTGCCTGTTATGGCTGCCCAGGTGG

TTGGGGGCACCCAGGCCTGTGAGGGAGGCTGGTCCCAGGGCCTTCCTCTTCCACCA

CCACCACCACCGGCTGCCCAGCTGCCCCCCATTGTGTCCCAAGGGAATGCTGGGCC

ATGGCCACAAGGGGCTCACGGAGAGGGCAGCCTGGCTTCCTCCCAGGCCAAGGCCC
```

-continued

```
CGCCAGATGACTCCTGTAACCCCAGGAGTGTCTATGAGAACTTCCGACTCTGGCAG

CACTACAAGCCCCTGGCCCGGAGGCACCTTCCCCAGAGTCCTGACACCGAAGCGCT

TTCGTGCTTCCTCATCCCAGTTCTCCGATCCCTGGCCCGGCGGAAGCCCACCATGA

CCCTGGAGGAGGGACTGTGGCGGGCCATGCGGGAATGGCAGCACACGAGCAACTTT

GACCGGATGATCTTCTACGAGATGGCGGAAAAGTTCCTGGAGTTTGAGGCTGAGGA

GGAGATGCAGATTCAGAAATCGCAATGGATGAAGGGGCCCCAGTGCCTGCCTCCTC

CAGCCACACCGAGGCTTGAACCTCGAGGACCCCCGGCCCCTGAGGTGGTCAAGCAG

CCAGTGTACCTTCCCAGCAAGGCCGGCCCCAAGGCCCCGACTGCCTGCCTGCCACC

ACCCAGGCCCCAGAGGCCAGTGACCAAGGCCCGCCGGCCACCACCCCGGCCCCACC

GGCGAGCAGAGACCAAGGCCCGCCTGCCACCACCCAGGCCCCAGAGACCAGCAGAG

ACCAAGGTCCCTGAGGAGATCCCCCCAGAAGTGGTGCAGGAGTATGTGGACATCAT

GGAGGAGCTGCTGGGGCCTTCCCTCGGGGCCACGGGGGAGCCCGAGAAACAACGGG

AAGAGGGCGAAGTGAAGCAGCCACAGGAAGAGGACTGGACGCCCCAGACCCGGGC

CTCCTGAGCTACACTGACAAGCTGTGTTCCCAGAAAGACTTCGTCACCAAGGTGGA

GGCCGTCATTCATCCCCAATTCCTGGAAGAATTGCTTTCCCCAGATCCACAGATGG

ATTTCTTGGCCCTAAGCCAGGAGCTGGAGCAGGAGGAAGGACTCACCCTTGCCCAG

CTAGTGGAGAAGCGCCTCCTACCCTTGAAGGAGAAACAGCATGCGAGGGCAGCCCC

TAGTCGTGGCACAGCCCGGTTGGACTCAAGTTCTTCTAAGTTTGCAGCTGGCCAAG

GAGCAGAGAGAGACGTCCCTGTCCCCAACAAGGGGTTGGCATGGAAACCTGCCCA

CCCCAGACGACTGCCCGGGACTCTCAGGGACGAGGCAGAGCACACACTGGCATGGC

CAGGTCCAAAGACTCTGTTGTGCTTTTGGGATGTCAGGATTCCCCTGGGCTGAGGG

CTGCCCGGCCAACCTCTCCTCCCCAGGACCACAGACCCACCTGCCCTGGCGTGGGT

ACCAAGGATGCCTTGGATCTCCCTGGAGGGTCTCCTGTCAGGGAGTCACATGGGCT

GGCTCAGGGGTCAAGTGAGGAGGAGGAACTCCCCAGCCTGGCCTTCCTCTTGGGTT

CCCAGCACAAGCTTCTGCCCTGGTGGCTACCCCAGAGCCCTGTCCCTGCCTCGGGC

CTTCTCAGCCCAGAAAAGTGGGGACCCCAGGGAACTCATCAGTTCCCATCTGCTGA

GAGAAGAGGCCTCAACCTAGCACCTTCTCCTGCCAACAAGGCCAAGAAGCGACCTC

TCTTTGGAAGCCTGTCCCCTGCTGAAAAGACACCCCACCCAGGGCCTGGGCTCAGG

GTCTCTGGGGAGCAATCCCTGACTTGGGGGCTGGGTGGCCCCTCACAGTCTCAAAA

GAGAAAGGGTGACCCCTTGGTCTCCAGGAAGGAGAAGAAGCAGCGTTGTAGCCAGT

AG (Nucleotide sequence of nucleic acid encoding YWHAE-FAM22B)
                                        SEQ ID NO: 2
ATGGATGATCGAGAGGATCTGGTGTACCAGGCGAAGCTGGCCGAGCAGGCTGAGCG

ATACGACGAAATGGTGGAGTCAATGAAGAAAGTAGCAGGGATGGATGTGGAGCTGA

CAGTTGAAGAAAGAAACCTCCTATCTGTTGCATATAAGAATGTGATTGGAGCTAGA

AGAGCCTCCTGGAGAATAATCAGCAGCATTGAACAGAAAGAAGAAAACAAGGGAGG

AGAAGACAAGCTAAAAATGATTCGGGAATATCGGCAAATGGTTGAGACTGAGCTAA

AGTTAATCTGTTGTGACATTCTGGATGTACTGGACAAACACCTCATTCCAGCAGCT

AACACTGGCGAGTCCAAGGTTTTCTATTATAAAATGAAAGGGGACTACCACAGGTA

TCTGGCAGAATTTGCCACAGGAAACGACAGGAAGGAGGCTGCGGAGAACAGCCTAG
```

-continued

```
TGGCTTATAAAGCTGCTAGTGATATTGCAATGACAGAACTTCCACCAACGCATCCT
ATTCGCTTAGGTCTTGCTCTCAATTTTTCCGTATTCTACTACGAAATTCTTAATTC
CCCTGACCGTGCCTGCAGGTTGGCAAAAGCAGCTTTTGATGATGCAATTGCAGAAC
TGGATACGCTGAGTGAAGAAAGCTATAAGGACTCTACACTTATCATGCAGTTGTTA
CGTGATAATCTGACACTATGGACTTCAGACATGCAGGGTGACGCATACCCAGTGCT
GGGACCGGGCGTGACCGCGAACCCTGGCACCTCCCTGTCTGTGTTCACGGCTCTGC
CCTTCACCACACCCGCTCCCGGCCCAGCACACGGGCCGCTCCTTGTGACTGCAGGG
GCTCCTCCAGGCGGCCCTCTGGTGCTGTCTACCTTCCCCAGCACACCTCTGGTGAC
AGAACAGGATGGCTGCGGCCCGAGTGGGGCCGGGGCTTCCAACGTCTTTGTCCAGA
TGAGGACAGAGGTGGGGCCTGTGAAGGCCGCTCAGGCGCAGACCTTGGTCCTAACT
CAGGCCCCCCTCGTCTGGCAGGCTCCAGGCGCCCTCTGCGGAGGTGTTGTGTGTCC
ACCTCCCCTACTCCTGGCAGCTGCTCCTGTGGTGCCTGTTATGGCTGCCCAGGTGG
TTGGGGGCACCCAGGCCTGTGAGGGAGGCTGGTCCCAGGGCCTTCCTCTTCCACCA
CCACCACCACCGGCTGCCCAGCTGCCCCCCATTGTGTCCCAAGGGAATGCTGGGCC
ATGGCCACAAGGGGCTCATGGAGAGAGCAGCCTGGCTTCCTCCCAGGCCAAGGCCC
CGCCAGATGACTCCTGTAACCCCAGGAGTGTCTATGAGAACTTCCGACTCTGGCAG
CACTACAAGCCCCTGGCCCGGAGGCACCTTCCCCAGAGTCCTGACACCGAAGCGCT
TTCGTGCTTCCTCATCCCAGTTCTCCGATCGCTGGCCCGGCGGAAGCCCACCATGA
CCCTGGAGGAGGGACTGTGGCGGGCCATGCGGGAATGGCAGCACACGAGCAACTTT
GACCGGATGATCTTCTACGAGATGGCGGAAAAGTTCCTGGAGTTTGAGGCTGAGGA
GGAGATGCAGATTCAGAAATCGCAATGGATGAAGGGGCCCCAGTGCCTGCCTCCTC
CAGCCACACCGAGGCTTGAACCTCGAGGACCCCCGGCCCCTGAGGTGGTCAAGCAG
CCAGTGTACCTTCCCAGCAAGGCCGGCCCCAAGGCCCCGACTGCCTGCCTGCCACC
ACCCAGGCCCCAGAGGCCAGTGACCAAGGCCCGCCGGCCACCACCCCGGCCCCACC
GGCGAGCAGAGACCAAGGCCCGCCTGCCACCACCCAGGCCCCAGAGACCAGCAGAG
ACCAAGGTCCCTGAGGAGATCCCCCCAGAAGTGGTGCAGGAGTATGTGGACATCAT
GGAGGAGCTGCTGGGGCCTTCCCTCGGGGCCACGGGGGAGCCCGAGAAACAACGGG
AAGAGGGCAAAGTGAAGCAGCCACAGGAAGAGGACTGGACGCCCCCAGACCCGGGC
CTCCTGAGCTACATTGACAAGCTGTGTTCCCAGAAAGACTTCGTCACCAAGGTGGA
GGCCGTCATTCATCCCCAATTCCTGGAAGAATTGCTTTCCCCAGATCCACAGATGG
ATTTCTTGGCCCTAAGCCAGGACCTGGAGCAGGAGGAAGGACTCACCCTTGCCCAG
CTAGTGGAGAAGCGCCTCCCACCCTTGAAGGAGAAACAGCATGCGAGGGCAGCCCC
TAGTCGTGGCACAGCCCGGTTGGACTCAAGTTCTTCTAAGTTTGCAGCTGGCCAAG
GAGCAGAGAGAGACGTCCCTGACCCCCAACAAGGGGTTGGCATGGAAACCTGCCCA
CCCCAGATGACTGCCCGGGACTCTCAGGGACGAGGCAGAGCACACACTGGCATGGC
CAGGTCCGAAGACTCTGTTGTGCTTTTGGGATGTCAGGATTCCCCTGGGCTGAGGG
CTGCCTGGCCAACCTCTCCTCCCCAGGACCACAGACCCACCTGCCCTGGCGTGGGT
ACCAAGGATGCCTTGGATCTCCCTGGAGGGTCTCCTGTCAGGGAGTCACATGGGCT
GGCTCAGGGGTCAAGTGAGGAGGAGGAACTCCCCAGCCTGGCCTTCCTCTTGGGTT
CCCAGCACAAGCTTCTGCCCTGGTGGCTACCCCAGAGCCCTGTCCCTGCCTCGGGC
CTTCTCAGCCCAGAAAAGTGGGGACCCCAGGGAACTCATCAGTCCCCATCTGCTGA
```

-continued

```
GAGAAGAGGCCTCAACCTAGCACCTTCTCCTGCCAACAAGGCCAAGAAGCGACCTC

TCTTTGGAAGCCTGTCCCCTGCTGAAAAGACACCCTACCCAGGGCCTGGGCTCAGG

GTCTCTGGGGAGCAATCCCTGACTTGGGGGCTGGGTGGCCCCTCACAGTCTCAAAA

GAGAAAGGGTGACCCCTTGGTCTCCAGGAAGGAGAAGAAGCAGCATTGTAGCCAGT

AG
```

(Amino acid sequence of YWHAE-FAM22A fusion protein)

SEQ ID NO: 3

```
MDDREDLVYQAKLAEQAERYDEMVESMKKVAGMDVELTVEERNLLSVAYKNVIGAR

RASWRIISSIEQKEENKGGEDKLKMIREYRQMVETELKLICCDILDVLDKHLIPAA

NTGESKVFYYKMKGDYHRYLAEFATGNDRKEAAENSLVAYKAASDIAMTELPPTHP

IRLGLALNESVFYYEILNSPDRACRLAKAAFDDAIAELDTLSEESYKDSTLIMQLL

RDNLTLWTSDMQGDAYPALGPGVTANPGTSLSVFTALPFTTPAPGPAHGPLLVTAG

APPGGPLVLSTLPSTPLVTEQDGCGPSGAGASNVFVQMRTEVGPVKAAQAQTLVLT

QaAPLVWQAPGALCGGVVCPPPLLLAAAPVVPVMAAQVVGGTQACEGGWSQGLPLP

PPPPPAAQLPPIVSQGNAGPWPQGAHGEGSLASSQAKAPPDDSCNPRSVYENFRLW

QHYKPLARRHLPQSPDTEALSCFLIPVLRSLARRKPTMTLEEGLWRAMREWQHTSN

FDRMIFYEMAEKFLEFEAEEEMQIQKSQWMKGPQCLPPPATPRLEPRGPPAPEVVK

QPVYLPSKAGPKAPTACLPPPRPQRPVTKARRPPPRPHRRAETKARLPPPRPQRPA

ETKVPEEIPPEVVQEYVDIMEELLGPSLGATGEPEKQREEGEVKQPQEEDWTPPDP

GLLSYTDKLCSQKDFVTKVEAVIHPQFLEELLSPDPQMDFLALSQELEQEEGLTLA

QLVEKRLLPLKEKQHARAAPSRGTARLDSSSSKFAAGQGAERDVPVPQQGVGMETC

PPQTTARDSQGRGRAHTGMARSKDSVVLLGCQDSPGLRAARPTSPPQDHRPTCPGV

GTKDALDLPGGSPVRESHGLAQGSSEEEELPSLAFLLGSQHKLLPWWLPQSPVPAS

GLLSPEKWGPQGTHQFPSAERRGLNLAPSPANKAKKRPLFGSLSPAEKTPHPGPGL

RVSGEQSLTWGLGGPSQSQKRKGDPLVSRKEKKQRCSQ
```

(Amino acid sequence of YWHAE-FAM22B fusion protein)

SEQ ID NO: 4

```
MDDREDLVYQAKLAEQAERYDEMVESMKKVAGMDVELTVEERNLLSVAYKNVIGAR

RASWRIISSIEQKEENKGGEDKLKMIREYRQMVETELKLICCDILDVLDKHLIPAA

NTGESKVFYYKMKGDYHRYLAEFATGNDRKEAAENSLVAYKAASDIAMTELPPTHP

IRLGLALNFSVFYYEILNSPDRACRLAKAAFDDAIAELDTLSEESYKDSTLIMQLL

RDNLTLWTSDMQGDAYPVLGPGVTANPGTSLSVFTALPFTTPAPGPAHGPLLVTAG

APPGGPLVLSTFPSTPLVTEQDGCGPSGAGASNVFVQMRTEVGPVKAAQAQTLVLT

QAPLVWQAPGALCGGVVCPPPLLLAAAPVVPVMAAQVVGGTQACEGGWSQGLPLPP

PPPPAAQLPPIVSQGNAGPWPQGAHGESSLASSQAKAPPDDSCNPRSVYENFRLWQ

HYKPLARRHLPQSPDTEALSCFLIPVLRSLARRKPTMTLEEGLWRAMREWQHTSNF

DRMIFYEMAEKFLEFEAEEEMQIQKSQWMKGPQCLPPPATPRLEPRGPPAPEVVKQ

PVYLPSKAGPKAPTACLPPPRPQRPVTKARRPPPRPHRRAETKARLPPPRPQRPAE

TKVPEEIPPEVVQEYVDIMEELLGPSLGATGEPEKQREEGKVKQPQEEDWTPPDPG

LLSYIDKLCSQKDFVTKVEAVIHPQFLEELLSPDPQMDFLALSQDLEQEEGLTLAQ

LVEKRLPPLKEKQHARAAPSRGTARLDSSSSKFAAGQGAERDVPDPQQGVGMETCP

PQMTARDSQGRGRAHTGMARSEDSVVLLGCQDSPGLRAAWPTSPPQDHRPTCPGVG
```

-continued

TKDALDLPGGSPVRESHGLAQGSSEEEELPSLAFLLGSQHKLLPWWLPQSPVPASG

LLSPEKWGPQGTHQSPSAERRGLNLAPSPANKAKKRPLFGSLSPAEKTPYPGPGLR

VSGEQSLTWGLGGPSQSQKRKGDPLVSRKEKKQHCSQ

SEQ ID NO: 6:
TGTTACGTGATAATCTGACACTATGGACTTCAGACATGCAGGGTGACGCAT

SEQ ID NO: 7:
TGTTACGTGATAATCTGACACTATGGACTTCAGACATGCAGGGTGACGCAT

SEQ ID NO: 8:
GTTACGTGATAATCTGACACTATGGACTTCAGACATGCAGGGTGACGCATA

SEQ ID NO: 9:
GTTACGTGATAATCTGACACTATGGACTTCAGACATGCAGGGTGACGCATA

SEQ ID NO: 10:
GTTACGTGATAATCTGACACTATGGACTTCAGACATGCAGGGTGACGCATA

SEQ ID NO: 11:
TTACGTGATAATCTGACACTATGGACTTCAGACATGCAGGGTGACGCATAC

SEQ ID NO: 12:
TTACGTGATAATCTGACACTATGGACTTCAGACATGCAGGGTGACGCATAC

SEQ ID NO: 13:
TACGTGATAATCTGACACTATGGACTTCAGACATGCAGGGTGACGCATACC

SEQ ID NO: 14:
TACGTGATAATCTGACACTATGGACTTCAGACATGCAGGGTGACGCATACC

SEQ ID NO: 15:
ACGTGATAATCTGACACTATGGACTTCAGACATGCAGGGTGACGCATACCC

SEQ ID NO: 16:
CGTGATAATCTGACACTATGGACTTCAGACATGCAAGGTGACGCATACCCA

SEQ ID NO: 17:
GTGATAATCTGACACTATGGACTTCAGACATGCAGGGTGACGCATACCCAG

SEQ ID NO: 18:
GTGATAATCTGACACTATGGACTTCAGACATGCAGGGTGACGCATACCCAG

SEQ ID NO: 19:
GTGATAATCTGACACTATGGACTTCAGACATGCAGGGTGACGCATACCCAG

SEQ ID NO: 20:
GTGATAATCTGACACTATGGACTTCAGACATGCAGGGTGACGCATACCCAG

SEQ ID NO: 21:
GTGATAATCTGACACTATGGACTTCAGACATGCAGGGTGACGCATACCCAG

SEQ ID NO: 22:
GTGATAATCTGACACTATGGACTTCAGACATGCAGGGTGACGCATACCCAG

SEQ ID NO: 23:
GTGATAATCTGACACTATGGACTTCAGACATGCAGGGTGACGCATACCCAG

SEQ ID NO: 24:
TGATAATCTGACACTATGGACTTCAGACATGCAGGGTGACGCATACCCAGC

SEQ ID NO: 25:
TGATAATCTGACACTATGGACTTCAGACATGCAGGGTGACGCATACCCAGC

SEQ ID NO: 26:
TGATAATCTGACACTATGGACTTCAGACATGCAGGGTGACGCATACCCAGC

SEQ ID NO: 27:
TGATAATCTGACACTATGGACTTCAGACATGCAGGGTGACGCATACCCAGC

SEQ ID NO: 28:
TGATAATCTGACACTATGGACTTCAGACATGCAGGGTGACGCATACCCAGC

SEQ ID NO: 29:
GATAATCTGACACTATGGACTTCAGACATGCAGGGTGACGCATACCCAGCG

SEQ ID NO: 30:
GATAATCTGACACTATGGACTTCAGACATGCAGGGTGACGCATACCCAGCG

SEQ ID NO: 31:
ATAATCTGACACTATGGACTTCAGACATGCAGGGTGACGCATACCCAGCGC

SEQ ID NO: 32:
ATAATCTGACACTATGGACTTCAGACATGCAGGGTGACGCATACCCAGCGC

SEQ ID NO: 33:
TAATCTGACACTATGGACTTCAGACATGCAGGGTGACGCATACCCAGCGCT

SEQ ID NO: 34:
AATCTGACACTATGGACTTCAGACATGCAGGGTGACGCATAGCCAGCGCTG

SEQ ID NO: 35:
AATCTGACACTATGGACTTCAGACATGCAGGGTGACGCATACCCAGCGCTG

SEQ ID NO: 36:
ATCTGGCACTATGGACTTCAGACATGCAGGGTGACGCATACCCAGCGCTGG

SEQ ID NO: 37:
ATCTGACACTATGGACTTCAGACATGCAGGGTGACGCATACCCAGCGCTGG

SEQ ID NO: 38:
ATCTGACACTATGGACTTCAGACATGCAGGGTGACGCATACCCAGCGCTGG

SEQ ID NO: 39:
TCTGACACTATGGACTTCAGACATGCAGGGTGACGCATACCCAGCGCTGGG

SEQ ID NO: 40:
GACACTATGGACTTCAGACATGCAGGGTGACGCATACCCAGCGCTGGGACC

SEQ ID NO: 41:
GACACTATGGACTTCAGACATGCAGGGTGACGCATACCCAGCGCTGGGACC

SEQ ID NO: 42:
GACACTATGGACTTCAGACATGCAGGGTGACGCATACCCAGCGCTGGGACC

SEQ ID NO: 43:
ACACTATGGACTTCAGACATGCAGGGTGACGCATACCCAGCGCTGGGACCG

SEQ ID NO: 44:
CACTATGGACTTCAGACATGCAGGGTGACGCATACCCAGCGCTGGGACCGG

SEQ ID NO: 45:
CACTATGGACTTCAGACATGCAGGGTGACGCATACCCAGCGCTGGGACCGG

SEQ ID NO: 46:
ACTATGGACTTCAGACATGCAGGGTGACGCATACCCAGCGCTGGGACCGGG

SEQ ID NO: 47:
ACTATGGACTTCAGACATGCAGGGTGACGCATACCCAGCGCTGGGACCGGG

SEQ ID NO: 48:
ACTATGGACTTCAGACATGCAGGGTGACGCATACCCAGCGCTGGGACCGGG

SEQ ID NO: 49:
ACTATGGACTTCAGACATGCAGGGTGACGCATACCCAGCGCTGGGACCGGG

SEQ ID NO: 50:
CTATGGACTTCAGACATGCAGGGTGACGCATACCCAGCGCTGGGACCGGGC

SEQ ID NO: 51:
CTATGGACTTCAGACATGCAGGGTGACGCATACCCAGCGCTGGGACCGGGC

SEQ ID NO: 52:
CTATGGACTTCAGACATGCAGGGTGACGCATACCCAGCGCTGGGACCGGGC

SEQ ID NO: 53:
CTATGGACTTCAGACATGCAGGGTGACGCATACCCAGCGCTGGGACCGGGC

SEQ ID NO: 54:
TATGGACTTCAGACATGCAGGGTGACGCATACCCAGCGCTGGGACCGGGCG

SEQ ID NO: 55:
ATGGACTTCAGACATGCAGGGTGACGCATACCCAGCGCTGGGACCGGGCGT

SEQ ID NO: 56:
TGGACTTCAGACATGCAGGGTGACGCATACCCAGCGCTGGGACCGGGCGTG

SEQ ID NO: 57:
GGACTTCAGACATGCAGGGTGACGCATACCCAGCGCTGGGACCGGGCGTGA

-continued

SEQ ID NO: 58:
GGACTTCAGACATGCAGGGTGACGCATACCCAGCGCTGGGACCGGGCGTGA

SEQ ID NO: 59:
ACTTCAGACATGCAGGGTGACGCATACCCAGCGCTGGGACCGGGCGTGACC

SEQ ID NO: 60:
ACTTCAGACATGCAGGGTGACGCATACCCAGCGCTGGGACCGGGCGTGACC

SEQ ID NO: 61:
ACTTCAGACATGCAGGGTGACGCATACCCAGCGCTGGGACCGGGCGTGACC

SEQ ID NO: 62:
CTTCAGACATGCACGGTGACGCATACCCAGCGCTGGGACCGGGCGTGACCG

SEQ ID NO: 63:
CAGACATGCAGGGTGACGCATACCCAGCGCTGGGACCGGGCGTGACCGCGA

SEQ ID NO: 64:
CAGACATGCAGGGTGACGCATACCCAGCGCTGGGACCGGGCGTGACCGCGA

SEQ ID NO: 65:
AGACATGCAGGGTGACGCATACCCAGCGCTGGGACCGGGCGTGACCGCGAA

SEQ ID NO: 66:
AGACATGCAGGGTGACGCATACCCAGCGCTGGGACCGGGCGTGACCGCGAA

SEQ ID NO: 67:
AGACATGCAGGGTGACGCATACCCAGCGCTGGGACCGGGCGTGACCGCGAA

SEQ ID NO: 68:
GACATGCAGGGTGACGCATACCCAGCGCTGGGACCGGGCGTGACCGCGAAC

SEQ ID NO: 69:
ATGCAGGGTGACGCATACCCAGCGCTGGGACCGGGCGTGACCGCGAACCCT

SEQ ID NO: 70:
ATGCAGGGTGACGCATACCCAGCGCTGGGACCGGGCGTGACCGCGAACCCT

SEQ ID NO: 71:
ATGCAGGGTGACGCATACCCAGCGCTGGGACCGGGCGTGACCGCGAACCCT

SEQ ID NO: 72:
ATGCAGGGTGACGCATACCCAGCGCTGGGACCGGGCGTGACCGCGAACCCT

SEQ ID NO: 73:
TGCAGGGTGACGCATACCCAGCGCTGGGACCGGGCGTGACCGCGAACCCTG

SEQ ID NO: 74:
TGCAGGGTGACGCATACCCAGCGCTGGGACCGGGCGTGACCGCGAACCCTG

SEQ ID NO: 75:
TGCAGGGTGACGCATACCCAGCGCTGGGACCGGGCGTGACCGCGAACCCTG

SEQ ID NO: 76:
CAGGGTGACGCATACCCAGCGCTGGGACCGGGCGTGACCGCGAACCCTGGC

SEQ ID NO: 77:
AGGGTGACGCATACCCAGCGCTGGGACCGGGCGTGACCGCGAACCCTGGCA

SEQ ID NO: 78:
AGGGTGACGCATACCCAGCGCTGGGACCGGGCGTGACCGCGAACCCTGGCA

SEQ ID NO: 79:
AGGGTGACCCATACCCAGCGCTGGGACCGGGCGCGACCGCGAACCCTGGCA

SEQ ID NO: 80:
GGGTGACGCATACCCAGCGCTGGGACCGGGCGTGACCGCGAACCCTGGCAC

SEQ ID NO: 81:
GTGACGCATACCCAGCGCTGGGACCGGGCGTGACCGCGAACCCTGGCACCT

SEQ ID NO: 81:
5'-AGAGGCTGAGAGAGTCGGAGACA CTA-3'

SEQ ID NO: 82:
5'-TATGGATGATCGAGAGGATCTGGTG-3'

SEQ ID NO: 83:
5'-CAGAACTGGATACGCTGAGT GAAGAA-3'

-continued

SEQ ID NO: 84:
5'-CTCATAGACACTCCTGG GGTTACAGG-3'

SEQ ID NO: 85:
5'-TCTTGCTGGGCCTTAGCTTTG-3'

SEQ ID NO: 86:
5'-TATGTTCCAGGAACCTGTTTA-3'

SEQ ID NO: 87:
5'-AAGUUCAGGUCGAUAUGUGCA-3'

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. An assay for selecting a treatment regimen for a subject with endometrial stromal sarcoma, the assay comprising a step of detecting in a biological sample taken from the subject the presence of a YWHAE-FAM22 fusion protein or a nucleic acid encoding the same, wherein if at least one of the fusion protein or the nucleic acid is detected, then selecting, and administering, a treatment regimen comprising an effective amount of an anti-cancer agent to the subject.

2. The assay of claim 1, wherein the nucleic acid comprises the nucleotide sequence of SEQ ID NO: 1 or SEQ ID NO: 2 or the fusion protein comprises the amino acid sequence of SEQ ID NO: 3 or SEQ ID NO: 4.

3. The assay of claim 1, wherein the sample is selected from the group consisting of blood, urine, plasma, tissue, cell, and any combinations thereof.

4. The assay of claim 1, wherein method comprises contacting the sample with a first reagent that binds with the nucleic acid or the fusion protein.

5. The assay of claim 4, wherein the first reagent is selected from the group consisting of a nucleic acid, an antibody, a small molecule, a polypeptide, a peptide, a lipid, an oligo- or poly-saccharide, and any combinations thereof.

6. The assay of claim 4, wherein the first reagent further comprises a label to produce a signal so as to detect presence of the nucleic acid or the fusion protein in the sample.

7. The assay of any of 4, wherein the first reagent is covalently or non-covalently linked to a solid support.

8. The assay of claim 4, wherein the method further comprises contacting the sample with a second reagent, wherein the second reagent binds with the first reagent, the nucleic acid, or the fusion protein.

9. The assay of claim 8, wherein the first reagent is selected from the group consisting of a nucleic acid, an antibody, a small molecule, a polypeptide, a peptide, a lipid, an oligo- or poly-saccharide, and any combinations thereof.

10. The assay of claim 8, wherein the second reagent is covalently or non-covalently linked to a solid support.

11. The assay of claim 8, wherein the second reagent further comprises a label to produce a signal so as to detect presence of the first reagent bound to the nucleic acid or the fusion protein in the isolated sample.

12. The assay of claim 1, wherein the assay comprises subjecting the biological from the subject to:
   (i) at least one protein detection assay adapted to determine the presence of a YWHAE-FAM22 fusion protein; or,
   (ii) at least one nucleic acid sequence detection assay adapted to determine the presence of a nucleic acid encoding the YWHAE-FAM22 fusion protein.

* * * * *